United States Patent
Navia et al.

(10) Patent No.: US 10,010,416 B2
(45) Date of Patent: Jul. 3, 2018

(54) APPARATUS AND METHOD FOR REPLACING A DISEASED CARDIAC VALVE

(71) Applicant: The Cleveland Clinic Foundation, Cleveland, OH (US)

(72) Inventors: Jose L. Navia, Shaker Heights, OH (US); Ji-Feng Chen, Lakewood, OH (US); Shengqiang Gao, Beachwood, OH (US); Brian L. Davis, Moreland Hills, OH (US); Samantha Stucke, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 14/230,216

(22) Filed: Mar. 31, 2014

(65) Prior Publication Data

US 2014/0214156 A1 Jul. 31, 2014

Related U.S. Application Data

(60) Division of application No. 12/828,991, filed on Jul. 1, 2010, now Pat. No. 8,685,086, which is a
(Continued)

(51) Int. Cl.
*A61F 2/24* (2006.01)

(52) U.S. Cl.
CPC ............ *A61F 2/243* (2013.01); *A61F 2/2415* (2013.01); *A61F 2/2418* (2013.01); *A61F 2/2433* (2013.01);
(Continued)

(58) Field of Classification Search
CPC .................. A61F 2/2436; A61F 2/2418; A61F 2210/0061; A61F 2220/0016; A61L 27/3625; A61L 27/3683
See application file for complete search history.

(56) References Cited

U.S. PATENT DOCUMENTS 6,534,004 B2 * 3/2003 Chen .................. A61L 27/3683
422/1
7,156,880 B2 * 1/2007 Evans ..................... A61L 27/12
623/23.51
(Continued)

FOREIGN PATENT DOCUMENTS

WO 2008/070797 A2 6/2008
WO 2009/045338 A1 4/2009
(Continued)

OTHER PUBLICATIONS

Communication Pursuant to Article 94(3) EPC, EP Application No. 10719493.8, dated Feb. 25, 2015.
(Continued)

*Primary Examiner* — Brian Pellegrino
(74) *Attorney, Agent, or Firm* — Kurt T. Mulville, Esq.; VLP Law Group, LLP

(57) ABSTRACT

An apparatus for replacing a diseased cardiac valve is movable from a radially collapsed configuration to a radially expanded configuration. The apparatus comprises an expandable support member and a prosthetic valve secured therein. The main body portion extends between first and second end portions and includes an outer circumferential surface, a circumferential axis extending about the circumferential surface, and a plurality of wing members spaced apart from one another by an expandable region. Each of the wing members includes first and second end portions and a flexible middle portion extending between the end portions. The second end portion is integrally formed with the uyimain body portion. The first end portion is adjacent the circumferential axis and substantially flush with the outer circumferential surface in the radially collapsed configuration. The first end portion extends substantially radial to the
(Continued)

outer circumferential surface in the radially expanded configuration.

5 Claims, 53 Drawing Sheets

Related U.S. Application Data continuation-in-part of application No. 12/769,593, filed on Apr. 28, 2010, and a continuation-in-part of application No. 11/357,485, filed on Feb. 18, 2006.

(60) Provisional application No. 61/222,518, filed on Jul. 2, 2009.

(52) U.S. Cl.
CPC ....... *A61F 2/2436* (2013.01); *A61F 2220/005* (2013.01); *A61F 2220/0008* (2013.01); *A61F 2220/0016* (2013.01); *A61F 2220/0058* (2013.01); *A61F 2220/0075* (2013.01); *A61F 2230/005* (2013.01)

(56) References Cited

U.S. PATENT DOCUMENTS

| | | | |
|---|---|---|---|
| 2003/0023303 A1 | 1/2003 | Palmaz et al. | |
| 2004/0093060 A1* | 5/2004 | Seguin | A61F 2/2418 623/1.11 |
| 2005/0182486 A1* | 8/2005 | Gabbay | A61F 2/2409 623/2.11 |
| 2007/0179600 A1* | 8/2007 | Vardi | A61F 2/07 623/1.44 |
| 2008/0071361 A1 | 3/2008 | Tuval et al. | |
| 2011/0264186 A1* | 10/2011 | Berglung | A61F 2/86 623/1.15 |

FOREIGN PATENT DOCUMENTS

| | | |
|---|---|---|
| WO | 2009/108615 A1 | 9/2009 |
| WO | 2009/132187 A1 | 10/2009 |

OTHER PUBLICATIONS

European Search Report, EP Application 10794766.5, dated Jan. 5, 2018.

* cited by examiner

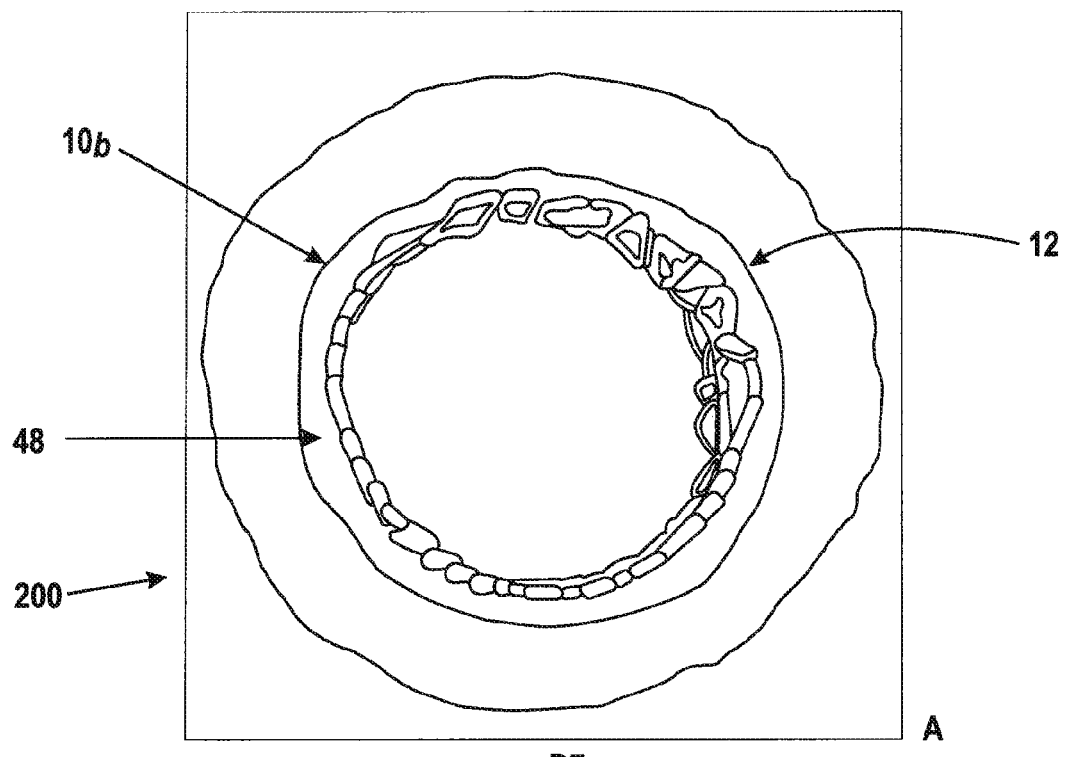
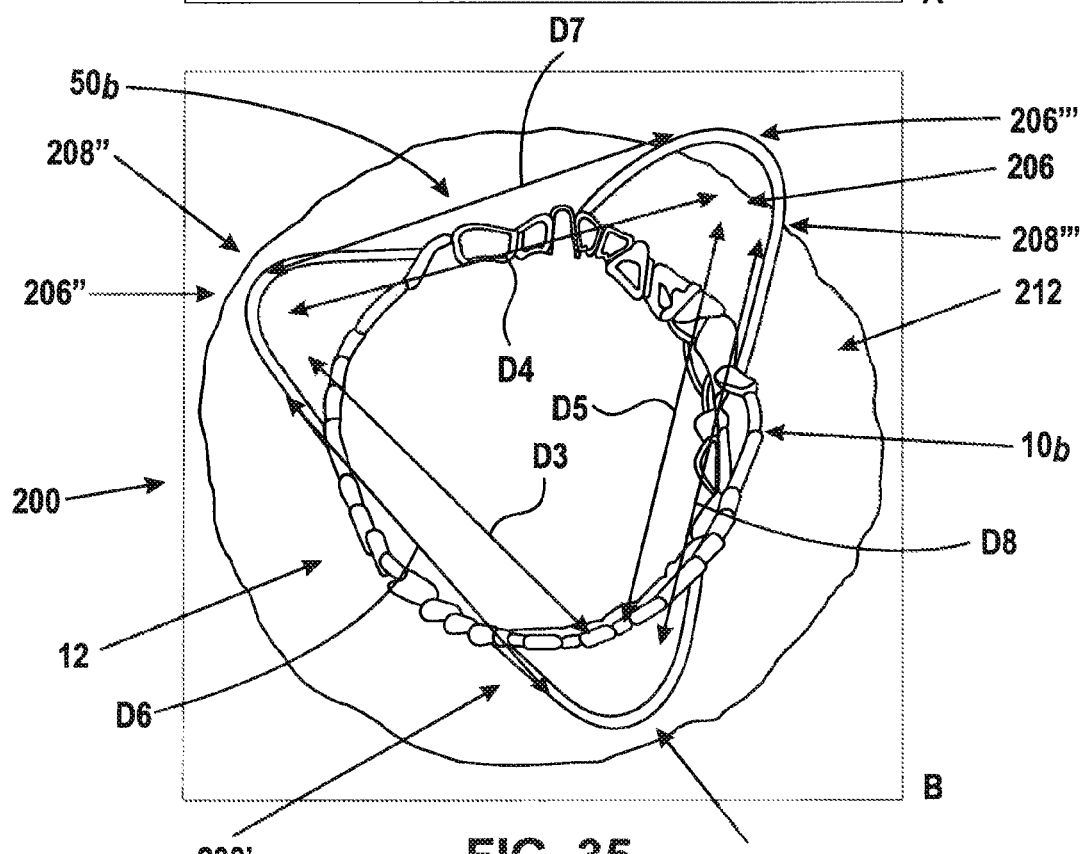
FIG. 35

APPARATUS AND METHOD FOR REPLACING A DISEASED CARDIAC VALVE

RELATED APPLICATIONS

This application claims priority from U.S. patent application Ser. No. 12/828,991 filed Jul. 1, 2010, issued as U.S. Pat. No. 8,685,086 on Apr. 1, 2014, which is a continuation in part of patent application Ser. No. 11/357,485 filed Feb. 18, 2006 and a continuation in part of patent application Ser. No. 12/769,593 filed Apr. 28, 2010, and provisional patent application Ser. No. 61/222,518, filed on Jul. 2, 2009, the subject matter of which are incorporated herein by reference.

TECHNICAL FIELD

The present invention relates generally to cardiac valve repair and replacement, and more particularly to an apparatus and method for the correction of cardiac valve disorders.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak (i.e., valve insufficiency). The leaflets and chords may become calcified and thickened, rendering them stenotic and obstructing forward blood flow. Finally, each of the valves relies on insertion of the chordae inside the ventricle. If the corresponding ventricle changes shape, the valve support may become non-functional and the valve may leak.

Mitral and tricuspid valve replacement and repair are traditionally performed with a suture technique. During valve replacement, sutures are spaced around the annulus and then attached to a prosthetic valve. The valve is lowered into position and, when the sutures are tied, the valve is fastened to the annulus. The surgeon may remove all or part of the valve leaflets before inserting the prosthetic valve.

In valve repair, a diseased valve is left in situ and surgical procedures are performed to restore its function. Frequently, an annuloplasty ring is used to reduce the size of the annulus. The ring serves to reduce the diameter of the annulus and allow the leaflets to oppose each other normally. Sutures are used to attach a prosthetic ring to the annulus and to assist in plicating the annulus.

In general, the annuloplasty rings and replacement valves must be sutured to the valve annulus during a time consuming and tedious procedure. If the ring is severely malpositioned, then the stitches must be removed and the ring repositioned relative to the valve annulus. In other cases, a less than optimum annuloplasty may be tolerated by the surgeon rather than lengthening the time of the surgery to re-stitch the ring. Moreover, during heart surgery, a premium is placed on reducing the amount of time used to replace and repair valves as the heart is frequently arrested and without perfusion.

SUMMARY OF THE INVENTION

According to one aspect of the present invention, an apparatus for replacing a diseased cardiac valve comprises an expandable support member and a prosthetic valve secured within a main body portion of the expandable support member. The apparatus is movable from a radially collapsed configuration to a radially expanded configuration. The expandable support member has a first end portion and a second end portion. The main body portion extends between the first and second end portions. The main body portion also includes an outer circumferential surface, a circumferential axis extending about the outer circumferential surface, and a plurality of wing members spaced apart from one another by an expandable region. Each of the wing members includes a first end portion, a second end portion, and a flexible middle portion extending between the first and second end portions. The second end portion of each of the wing members is integrally formed with the main body portion. The first end portion of each of the wing members is adjacent the circumferential axis and substantially flush with the outer circumferential surface when the apparatus is in the radially collapsed configuration. The first end portion of each of the wing members extends substantially radial to the outer circumferential surface when the apparatus is in the radially expanded configuration.

According to another aspect of the present invention, a method is provided for replacing a diseased cardiac valve. One step of the method includes providing an apparatus comprising an expandable support member having a prosthetic valve secured within a main body portion of the expandable support member. The main body portion also includes an outer circumferential surface, a circumferential axis extending about the outer circumferential surface, and a plurality of wing members spaced apart from one another by an expandable region. Each of the wing members includes a first end portion, a second end portion, and a flexible middle portion extending between the first and second end portions. The second end portion of each of the wing members is integrally formed with the main body portion. The expandable support member is placed, in a radially collapsed configuration, about an inflatable member and then loaded into a delivery catheter. Next, the delivery catheter is advanced to the diseased cardiac valve. The apparatus is then deployed, in a radially expanded configuration, so that the first end portion of each of the wing members extends substantially radial to the outer circumferential surface. Deployment of the apparatus causes the first end portion of each of the wing members to contact cardiac tissue and thereby secure the apparatus in place of the diseased cardiac valve.

According to another aspect of the present invention, a method is provided for replacing a diseased cardiac valve. One step of the method includes providing an apparatus comprising an expandable support member having a prosthetic valve secured within a main body portion of the expandable support member. The main body portion also includes an outer circumferential surface, a circumferential axis extending about the outer circumferential surface, and a plurality of wing members spaced apart from one another by an expandable region. Each of the wing members includes a first end portion, a second end portion, and a flexible middle portion extending between the first and second end portions. The second end portion of each of the wing members is integrally formed with the main body portion. The expandable support member is placed in a radially collapsed configuration and then advanced to the diseased cardiac valve. The apparatus is then deployed, in a radially expanded configuration, so that the first end portion of each of the wing members extends substantially radial to the outer circumferential surface. Deployment of the apparatus causes the first end portion of each of the wing members to contact cardiac tissue and thereby secure the apparatus in place of the diseased cardiac valve.

According to another aspect of the present invention, an apparatus for replacing an indwelling bioprosthetic valve has at least two commissural portions spaced apart by a first distance. The apparatus is movable from a radially collapsed configuration to a radially expanded configuration. The apparatus comprises an expandable support member having a first end portion, a second end portion, and a main body portion extending between the first and second end portions. The main body portion includes an outer circumferential surface and a circumferential axis extending about said outer circumferential surface. The apparatus also comprises a prosthetic valve secured within the main body portion of the expandable support member. The second end portion includes at least two flexible arch members spaced apart by a second distance that is about equal to the first distance. Each of the at least two arch members is substantially co-planar with the outer circumferential surface when the apparatus is in the radially collapsed configuration, and substantially radial to the outer circumferential surface when the apparatus is in the radially expanded configuration. The main body portion includes a plurality of wing members spaced apart from one another by an expandable region. Each of the wing members includes a first end portion, a second end portion, and a flexible middle portion extending between the first and second end portions. The second end portion of each of the wing members is integrally formed with the main body portion. The first end portion of each of the wing members is adjacent the circumferential axis and substantially flush with the outer circumferential surface when the apparatus is in the radially collapsed configuration. The first end portion of each of the wing members extends substantially radial to the outer circumferential surface when the apparatus is in the radially expanded configuration.

According to another aspect of the present invention, a method is provided for replacing an indwelling bioprosthetic valve in a subject. The indwelling bioprosthetic valve has at least two commissural portions spaced apart by a first distance. One step of the method includes providing an apparatus comprising an expandable support member and a prosthetic valve secured within a main body portion of the expandable support member. The main body portion includes an outer circumferential surface, a circumferential axis extending about the circumferential surface, and a plurality of wing members spaced apart from one another by an expandable region. Each of the wing members includes a first end portion, a second end portion, and a flexible middle portion extending between the first and second end portions. The second end portion of each of the wing members is integrally formed with the main body portion. The apparatus is loaded into a delivery catheter and then advancing the delivery catheter to the indwelling bioprosthetic valve. Next, the apparatus is deployed, in a radially expanded configuration, so that each of the at least two arch members engages each of the at least two commissural portions and the first end portion of each of the wing members extends substantially radial to the outer circumferential surface to displace a valve portion of the indwelling bioprosthetic valve.

According to another aspect of the present invention, an apparatus for replacing an indwelling bioprosthetic valve has at least two commissural portions spaced apart by a first distance. The apparatus is movable from a radially collapsed configuration to a radially expanded configuration. The apparatus comprises a cork-shaped expandable support member having a first end portion, a second end portion, and a main body portion extending between the first and second end portions. The first end portion has a flared configuration and includes a diameter that is greater than a diameter of the second end portion. The main body portion includes an outer circumferential surface and a circumferential axis extending about said outer circumferential surface. The apparatus also comprises a prosthetic valve secured within the first end portion of the expandable support member. The main body portion includes a plurality of wing members spaced apart from one another by an expandable region. Each of the wing members includes a first end portion, a second end portion, and a flexible middle portion extending between the first and second end portions. The second end portion of each of the wing members is integrally formed with the main body portion. The first end portion of each of the wing members is adjacent the circumferential axis and substantially flush with the outer circumferential surface when the apparatus is in the radially collapsed configuration. The first end portion of each of the wing members extends substantially radial to the outer circumferential surface when the apparatus is in the radially expanded configuration.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 35A-B are perspective views showing a first end portion (FIG. 34A) and a second end portion (FIG. 34B) of the apparatus in FIGS. 34A-B;

DETAILED DESCRIPTION

Figure 1A:
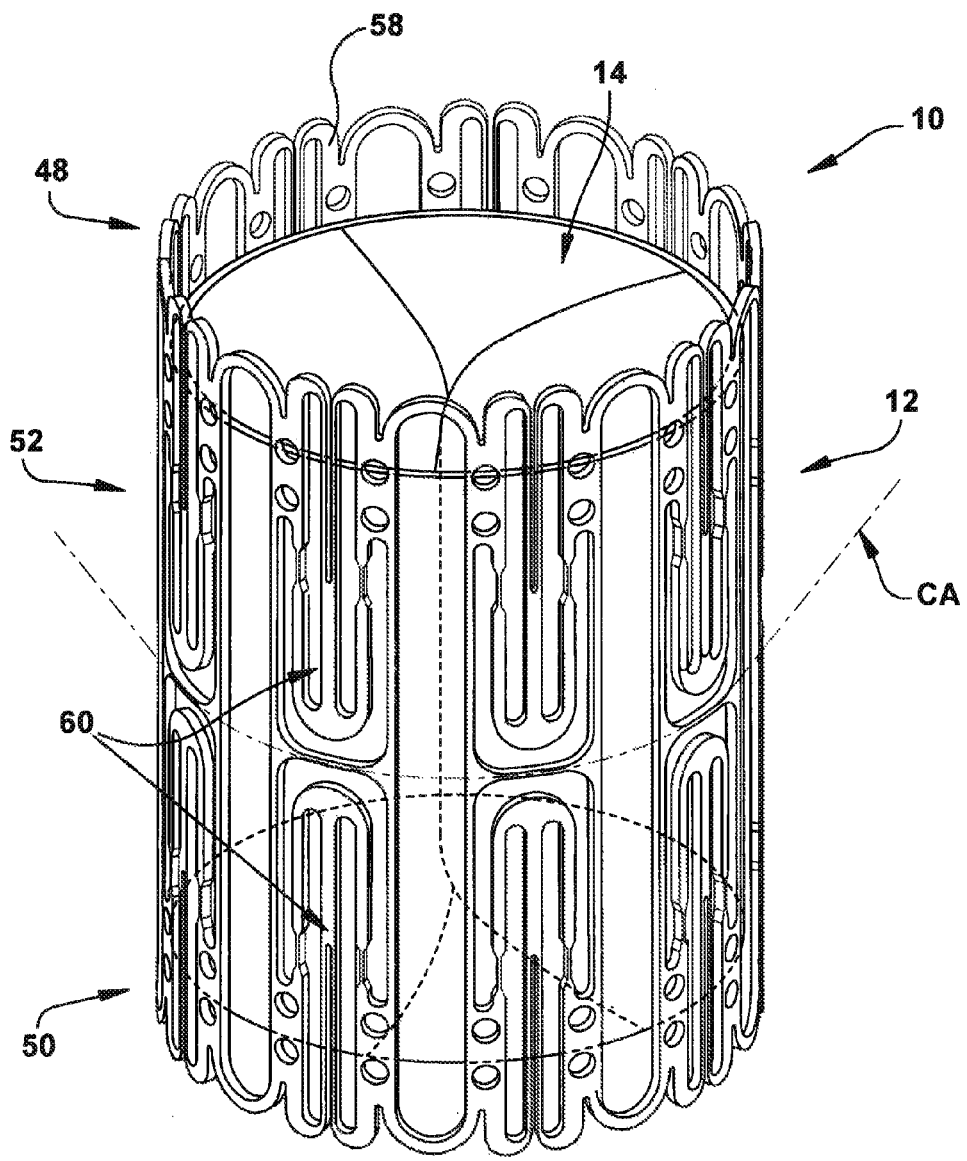
FIG. 1A is a perspective view showing an apparatus for replacing a diseased cardiac valve, in a radially collapsed configuration, constructed in accordance with one aspect of the present invention.
Figure 1B:
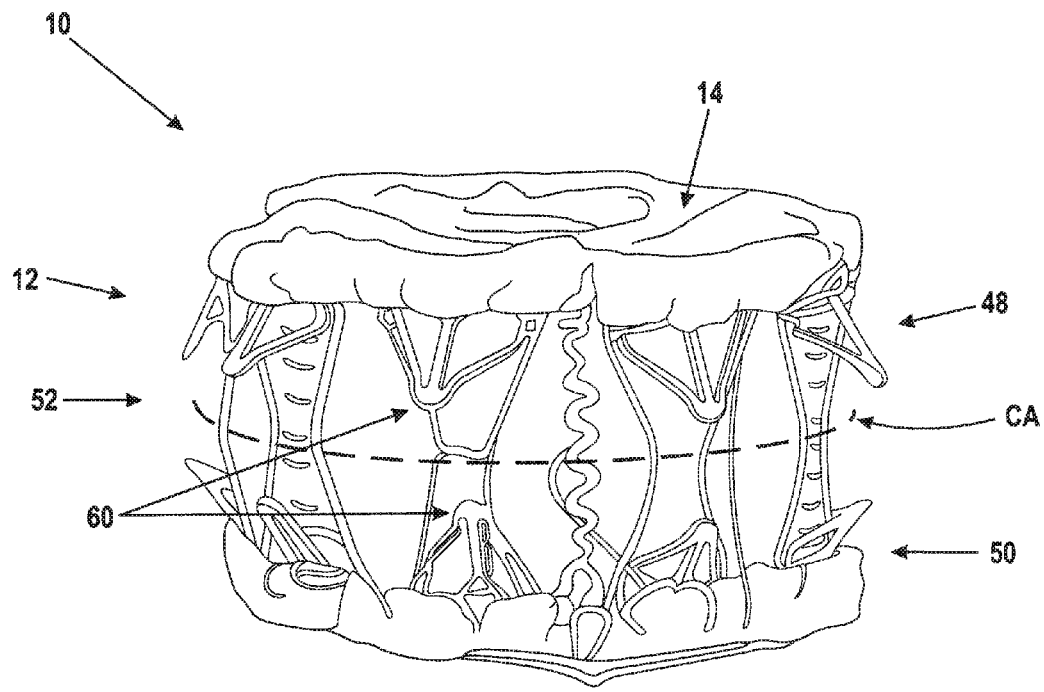
FIG. 1B is the apparatus in FIG. 1A in a radially expanded configuration.
Figure 43:
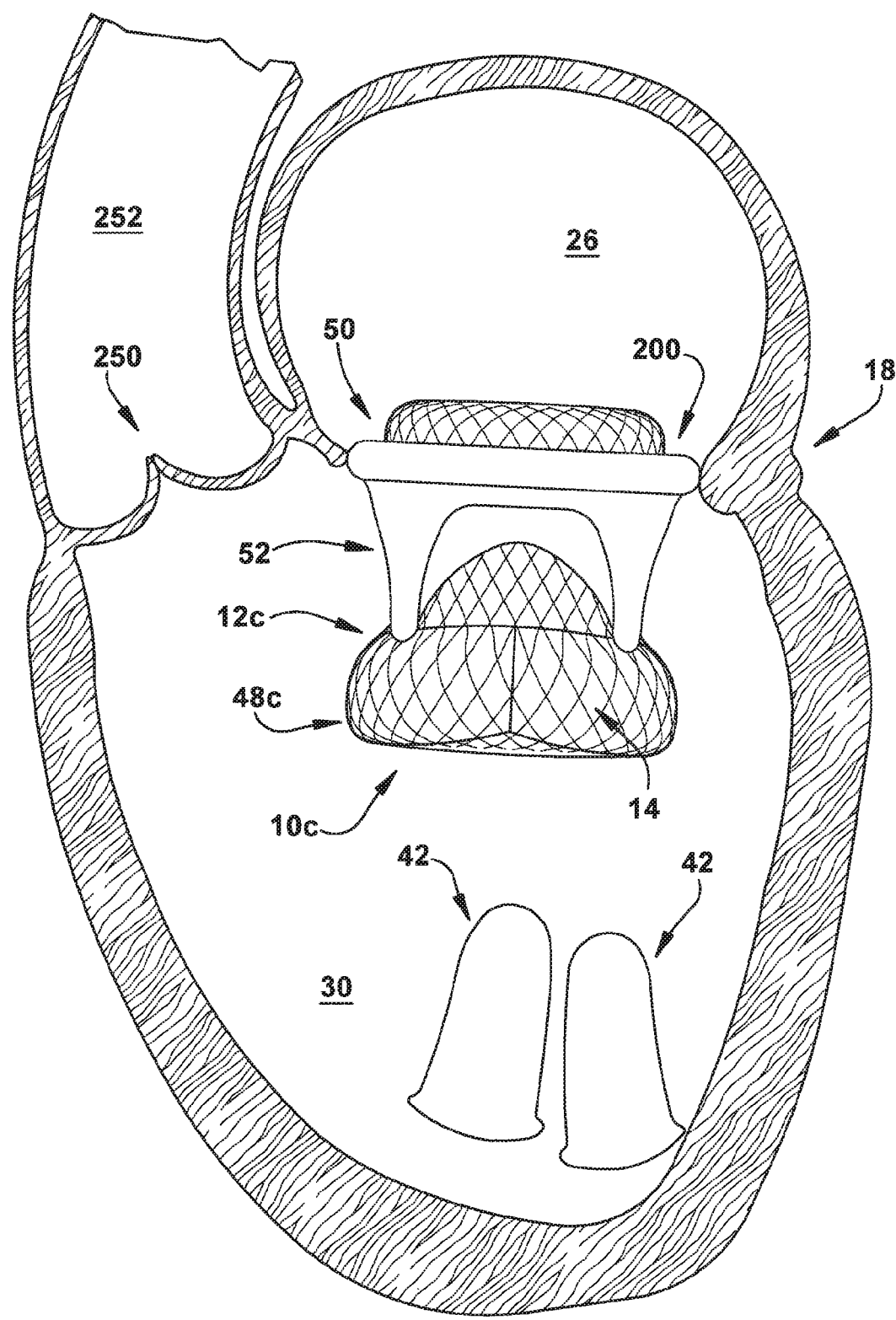
FIG. 43 is a cross-sectional view showing an alternative configuration of the apparatus in FIGS. 1A-B implanted in an indwelling bioprosthetic mitral valve.

The present invention relates generally to cardiac valve repair and replacement, and more particularly to an apparatus and method for the correction of cardiac valve disorders. As representative of the present invention, FIGS. 1A-B illustrate an apparatus 10 comprising an expandable support member 12 and a prosthetic valve 14 secured therein. The apparatus 10 is for replacing a diseased cardiac valve 16 (FIG. 2) (e.g., a mitral valve 18) by implanting the apparatus (FIGS. 1A-B) over the native or diseased cardiac valve so that the prosthetic valve 14 assumes the valvular function. Although the apparatus 10 is described below for replacing a diseased mitral valve 18 (FIG. 2), it should be understood that the apparatus could also be used to replace other diseased cardiac valves, such as the tricuspid valve 20, the pulmonary valve (not shown), and the aortic valve 250 (FIG. 43).

Figure 2:
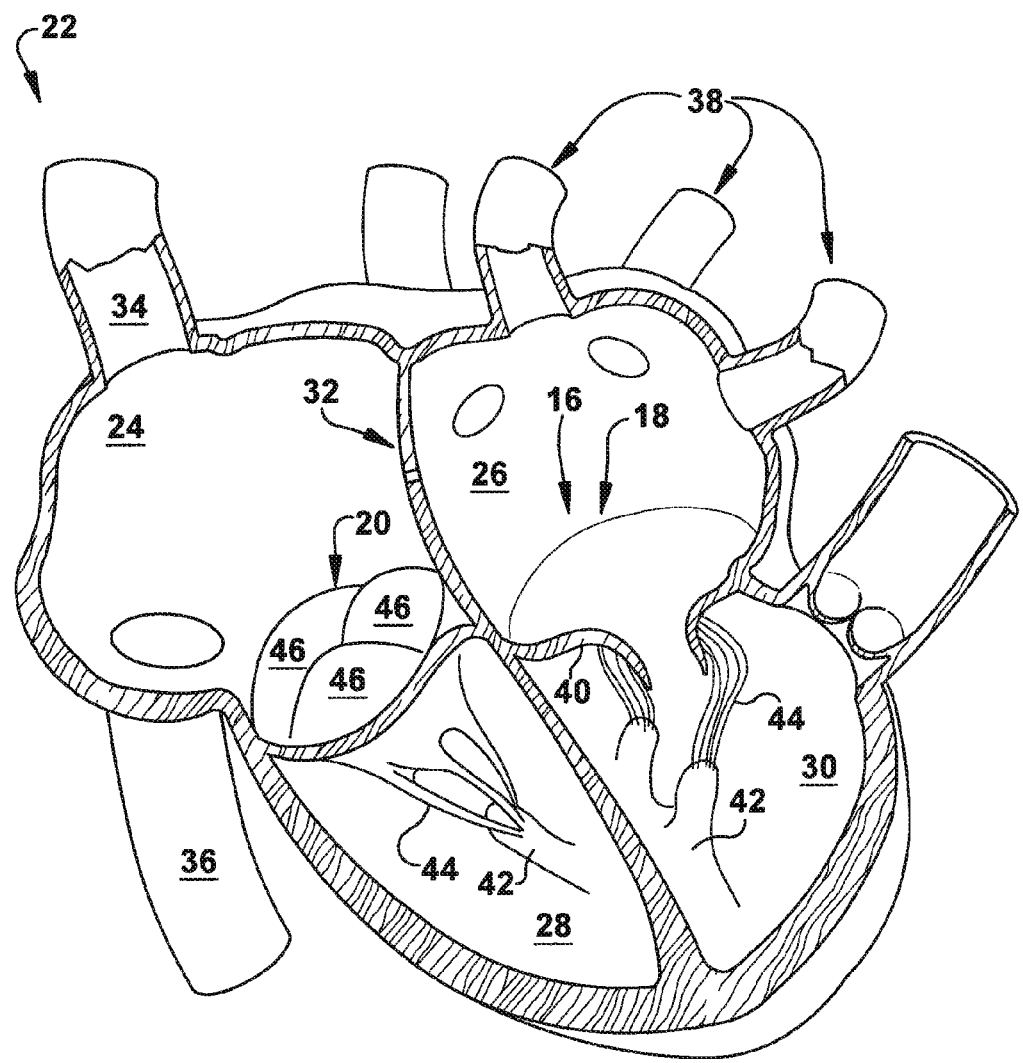
FIG. 2 is a view of a human heart.

FIG. 2 schematically illustrates a human heart 22, which includes four chambers: the right and left atria 24 and 26, respectively, and the right and left ventricles 28 and 30, respectively. The right and left atria 24 and 26 are divided by the interatrial septum 32. The thin-walled right atrium 24 receives deoxygenated blood from the superior vena cava 34, the inferior vena cava 36, and from the coronary sinus (not shown). The thin-walled left atrium 26 receives oxygenated blood from pulmonary veins 38. The right and left ventricles 28 and 30 pump oxygenated and deoxygenated blood, respectively, throughout the body, and the pocket-like semilunar pulmonary valve and the aortic valve prevent reflux into the ventricles. Atrial blood is pumped through the atrioventricular orifices, guarded by the tri-leaflet tricuspid valve 20 on the right side of the heart 22 and the bi-leaflet mitral valve 18 on the left side of the heart. The leaflets 40 of the mitral valve 18 are attached to the papillary muscles 42 in the left and right ventricles 30 and 28 by chordae tendineae 44. Similarly, the leaflets 46 of the tricuspid valve 20 are attached to the papillary muscles 42 in the left and right ventricles 30 and 28 by chordae tendineae 44.

Figure 3A:
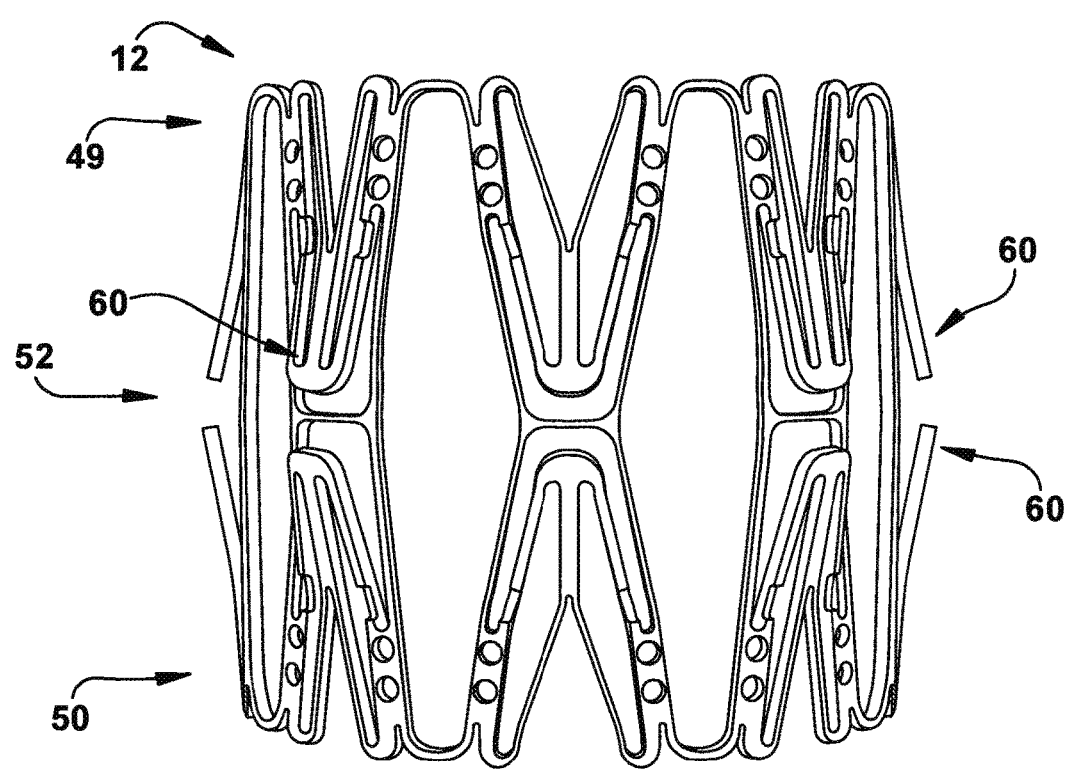
FIG. 3A is an expandable support member of the apparatus in FIGS. 1A-B in the radially collapsed configuration.
Figure 3B:
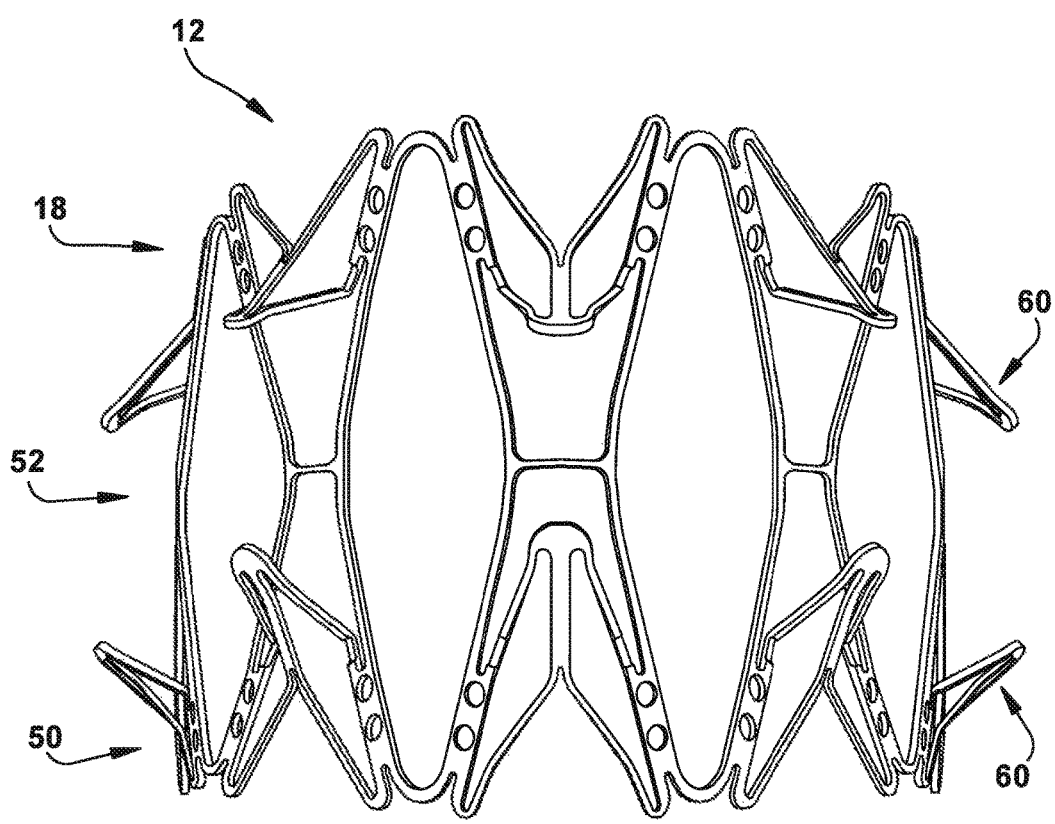
FIG. 3B is the expandable support member of FIG. 3A in the radially expanded configuration.
Figure 3C:
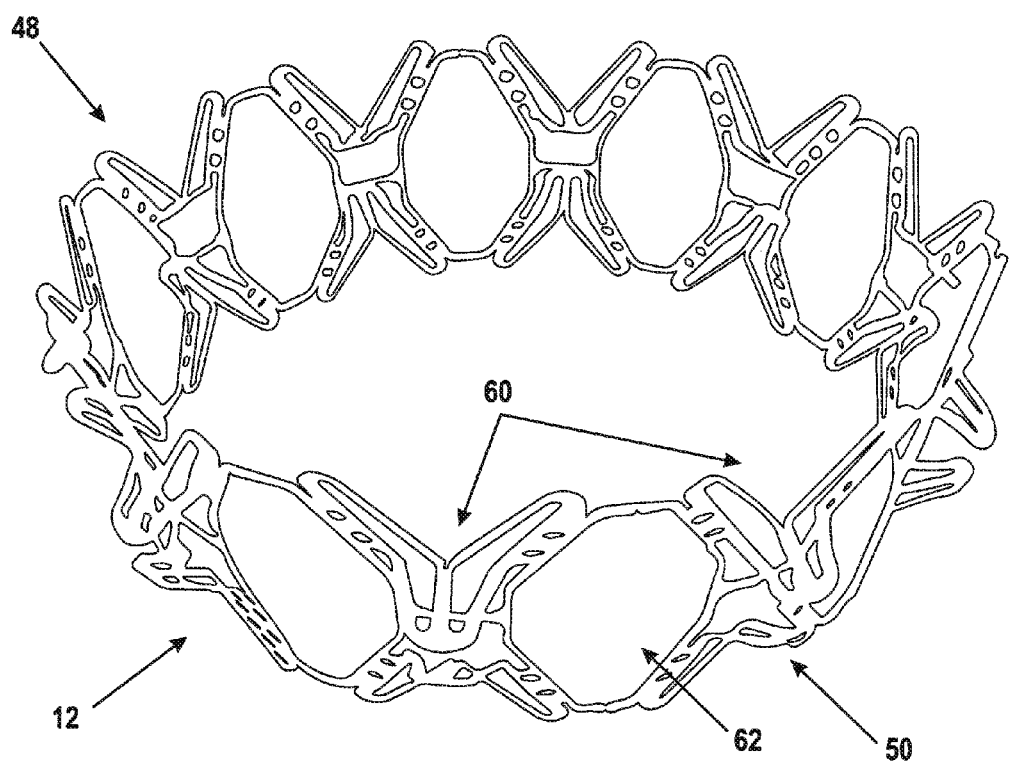
FIG. 3C is saddle-shaped, three-dimensional configuration of the expandable support member in the radially expanded configuration.

As shown in FIGS. 1A-B, one aspect of the present invention includes an apparatus 10 for replacing a diseased cardiac valve. The apparatus 10 comprises an expandable support member 12, commonly referred to as a stent, and a prosthetic valve 14 secured therein. The expandable support member 12 is generally annular in shape and has oppositely disposed first and second end portions 48 and 50 and a main body portion 52 extending between the end portions. Additionally, the expandable support member 12 has a saddle-shaped, three-dimensional (3D) configuration to mimic the 3D shape of a diseased cardiac valve (FIG. 3C). The expandable support member 12 (FIGS. 1A-B) has a flexible configuration that allows the apparatus 10 to transition between a radially collapsed configuration (FIG. 1A) and a radially expanded configuration (FIG. 1B). The flexible and expandable properties of the expandable support member 12 facilitate delivery of the apparatus 10, while also allowing the expandable support member to conform to the convex shape of the mitral valve annulus 54 (FIG. 12), for example.

All or only a portion of the expandable support member 12 (FIGS. 1A-B) may be made from a medical grade metal or plastic, including shape memory materials, such as Nitinol, stainless steel, and/or titanium. For example, all or only a portion of the expandable support member 12 may be made of a Co—Cr alloy, such as Co-20Cr-15W-10Ni. As described below, the expandable support member 12 may thus be self-expandable or mechanically expandable (e.g., using a balloon) depending upon the material used to construct the expandable support member. Additionally, at least a portion of the expandable support member 12 may be made from a bioabsorbable material, such as a magnesium alloy, dendrimers, biopolymers (e.g., thermoplastic starch), polylactides, cellulose, and aliphatic aromatic copolyesters.

The main body portion 52 (FIG. 1A) extends between the first and second end portions 48 and 50 of the expandable support member 12. The main body portion 52 includes an outer circumferential surface 56 oppositely disposed from an inner circumferential surface 58. As shown in FIG. 1A, a circumferential axis CA extends about or around the outer circumferential surface 56, approximately between the first and second end portions 48 and 50 of the expandable support member 12.

The main body portion 52 also includes a plurality of wing members 60 (FIGS. 3A-B) spaced apart from one another by an expandable region 62. Each of the wing members 60 (FIGS. 4A-B) has an arch-like shape and includes a first end portion 64, a second end portion 66, and a flexible middle portion 68 extending between the first and second end portions. The first end portion 64 of each of the wing members 60 is substantially adjacent the circumferential axis CA of the main body portion 52. The first end portion 64 of each of the wing members 60 can be sharpened or dull (e.g., arrow- or fish hook-shaped). It should be appreciated that the first end portion 64 of each of the wing members 60 can include at least one attachment mechanism (not shown) to facilitate attachment and positioning of the apparatus 10 in the annulus (not shown in detail) of the diseased cardiac valve 16. For example, the attachment mechanism can include at least one barb, hook, or other similar means for embedding into a section of cardiac tissue (e.g., annular tissue, myocardium, valve leaflet, chordae, etc.).

Figure 4A:
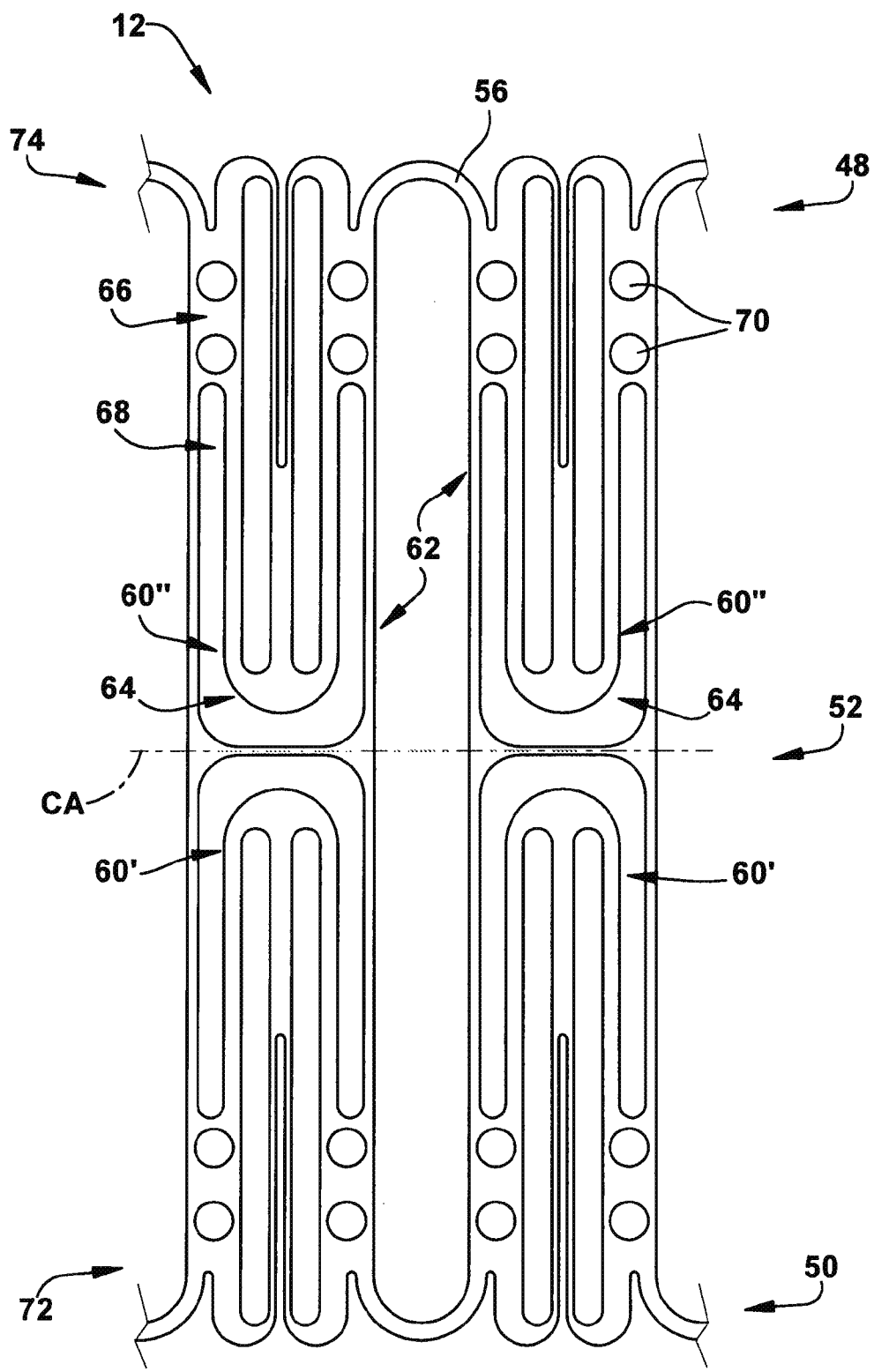
FIG. 4A is a plan view showing an exploded portion of the expandable support member in FIG. 1A.
Figure 4B:
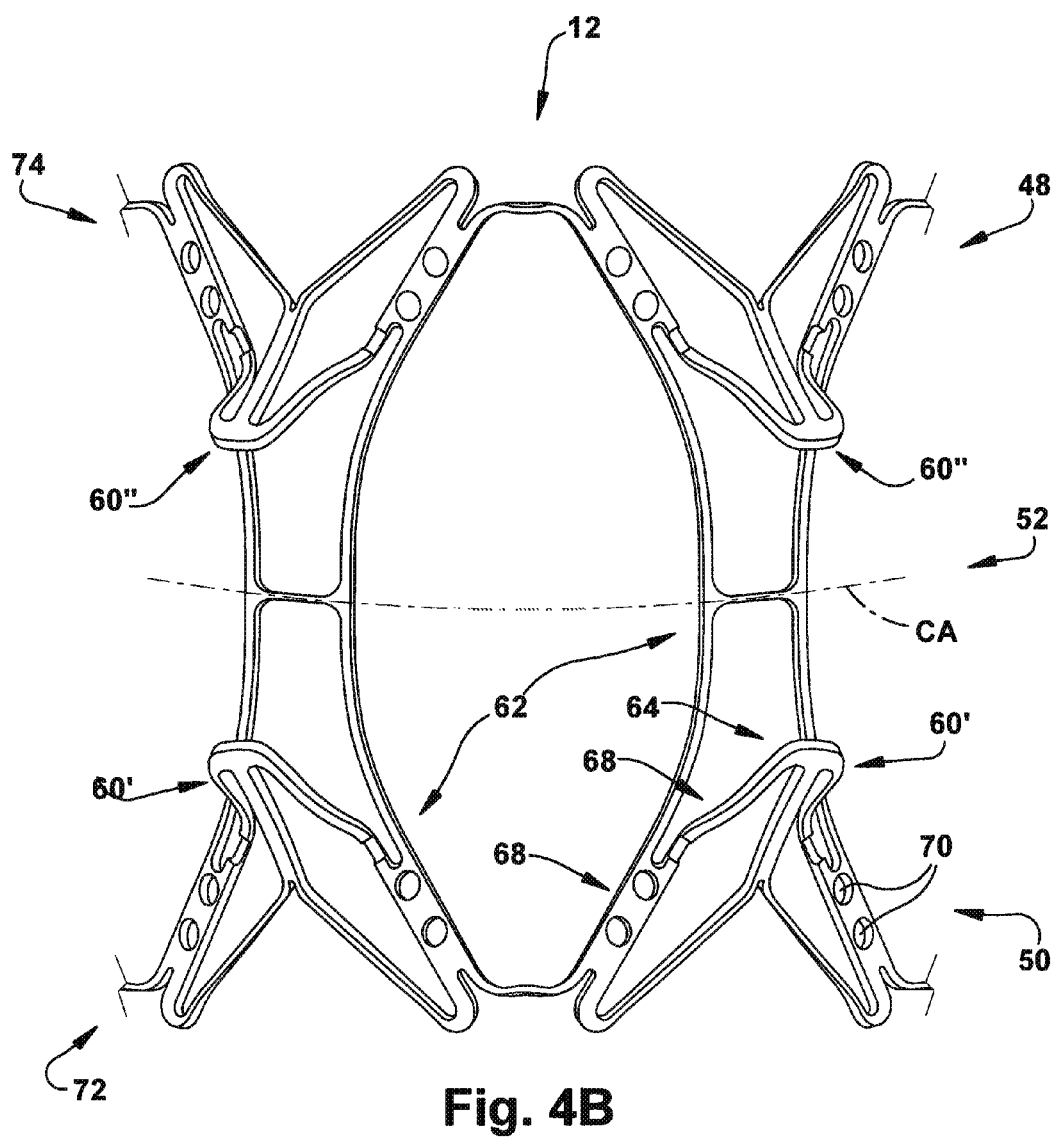
FIG. 4B is a plan view showing an exploded portion of the expandable support member in FIG. 1B and FIG. 3B.

As described below, the flexible middle portion 68 is resiliently bendable to allow the first end portion 64 of each of the wing members 60 to radially expand relative to the outer circumferential surface 56. As shown in FIGS. 4A-B, for example, the first end portion 64 of each of the wing members 60 is substantially flush with the outer circumferential surface 56 when the apparatus 10 is in the radially collapsed configuration. Additionally, the first end portion 64 of each of the wing members 60 extends substantially radial to both the circumferential axis CA and the outer circumferential surface 56 when the apparatus 10 is in the radially expanded configuration. In the expanded configuration, for example, the wing members 60 can bend, flex, or protrude outward so that they are offset from and/or non-coplanar with (e.g., substantially radial to) the outer circumferential surface 56. For instance, the wing members 60 can be offset from the outer circumferential surface 56 by about 1° to about 90° or more.

Figure 5A:
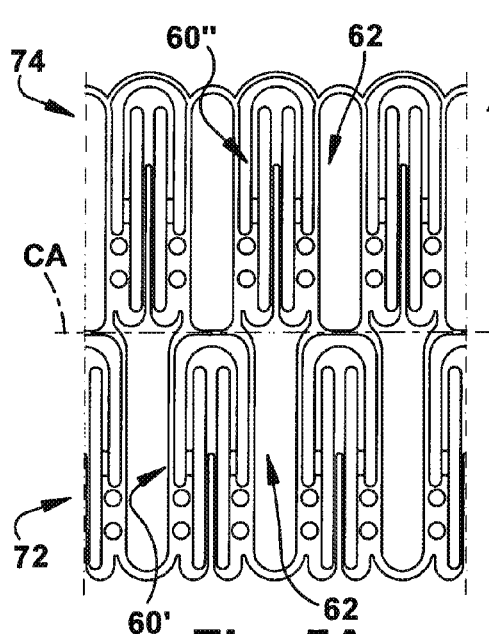
FIG. 5A is a plan view showing an alternative configuration of the expandable support member in FIG. 4A.

The second end portion 66 of each of the wing members 60 is integrally formed with a portion of the main body portion 52. As shown in FIGS. 4A-B, for example, the second end portion 66 of each of the wing members 60 is integrally formed with the main body portion 52, near the first and second end portions 48 and 50 of the expandable support member 12. The second end portion 66 can also be integrally formed with the main body portion 52 near the circumferential axis CA, as shown in FIG. 5A. The second end portion 66 (FIGS. 4A-B) of each of the wing members 60 can additionally or optionally include a plurality of openings 70 to facilitate attachment of the prosthetic valve 14 to the expandable support member 12. Although four circular openings 70 are shown at the second end portion 66 of each of the wing members 60, it will be appreciated that the second end portion can include any number and shape of openings.

The expandable support member 12 can include any number, size, and configuration of wing members 60. As illustrated in FIGS. 3A-B, for example, the apparatus 10 includes eighteen wing members 60 spaced about the main body portion 52 of the expandable support member 12. It should be understood, however, that the expandable support member 12 can include more or less than eighteen wing members 60. As shown in FIGS. 4A-B and FIGS. 5C-D, for example, a first plurality of wing members 60' can be circumferentially spaced around a lower portion 72 of the expandable support member 12, and a second plurality of wing members 60" can be circumferentially spaced around an upper portion 74 of the expandable support member. The first plurality of wing members 60' can be symmetrically aligned with the second plurality of wing members 60" (with respect to the circumferential axis CA). Alternatively, the first plurality of wing members 60' can be asymmetrically aligned with the second plurality of wing members 60" (with respect to the circumferential axis CA), as shown in FIG. 5A and FIG. 5C.

Figure 5B:
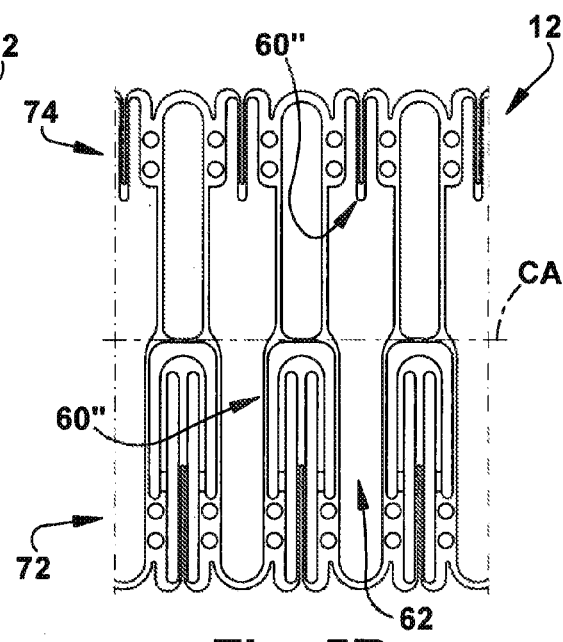
FIG. 5B is a plan view showing another alternative configuration of the expandable support member in FIG. 5A.
Figure 5C:
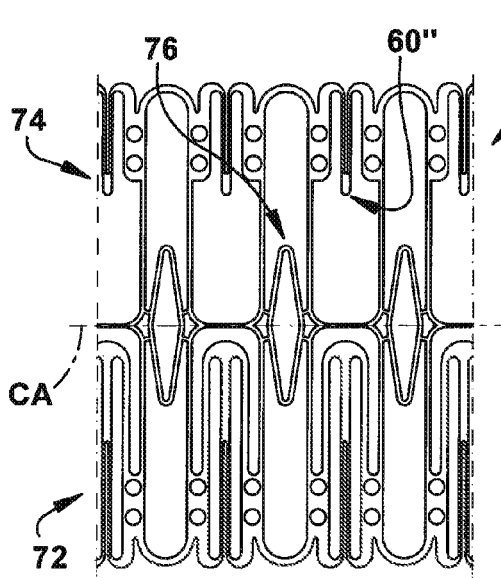
FIG. 5C is a plan view showing another alternative configuration of the expandable support member in FIG. 5B.
Figure 5D:
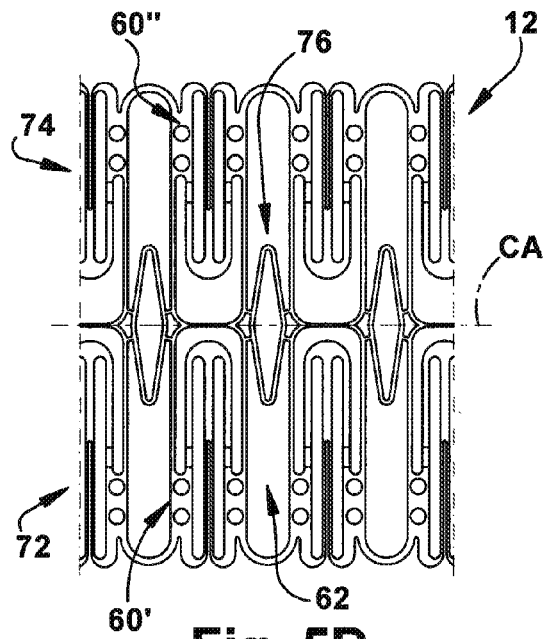
FIG. 5D is a plan view showing an alternative configuration of the expandable support member in FIG. 5C.

Other possible wing member 60 configurations are illustrated in FIGS. 5B-D. As shown in FIGS. 5B-C, each of the wing members 60" comprising the second plurality of wing members can have a size less than the size of each of the wing members 60' comprising the first plurality of wing members (e.g., ½, ⅓, or ⅔ of the size). For instance, each of the wing members comprising the second plurality of wing members 60" can have a size that is less than about two-thirds the size of the wing members comprising the first plurality of wing members 60'. It will be appreciated that each of the wing members 60' comprising the first plurality of wing members can alternatively have a size less than the size of each of the wing members 60" comprising the second plurality of wing members. Although the expandable support member 12 is shown as having wing members 60 at both the first and second end portions 48 and 50, it should be appreciated that only the first end portion or only the second end portion of the expandable support member may include a plurality of wing members.

The main body portion 52 of the expandable support member 12 also includes a plurality of expandable regions 62, each of which is spaced between the wing members 60 and extends between the first and second end portions 48 and 50 of the expandable support member. In the radially collapsed configuration shown in FIG. 4A, each of the expandable regions 62 obtains an elongated cylindrical configuration, whereas each of the expandable regions obtains a trapezoidal configuration in the radially expanded configuration (FIG. 4B).

Figure 6A:
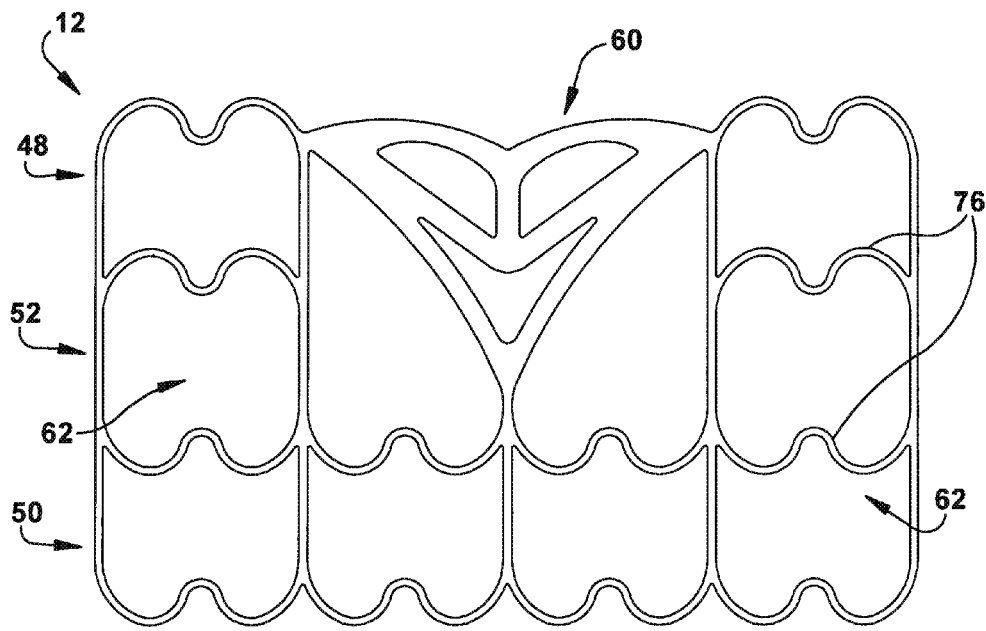
FIG. 6A is an exploded plan view showing an alternative configuration of an expandable region comprising a portion of the expandable support member in FIG. 4A.
Figure 6B:
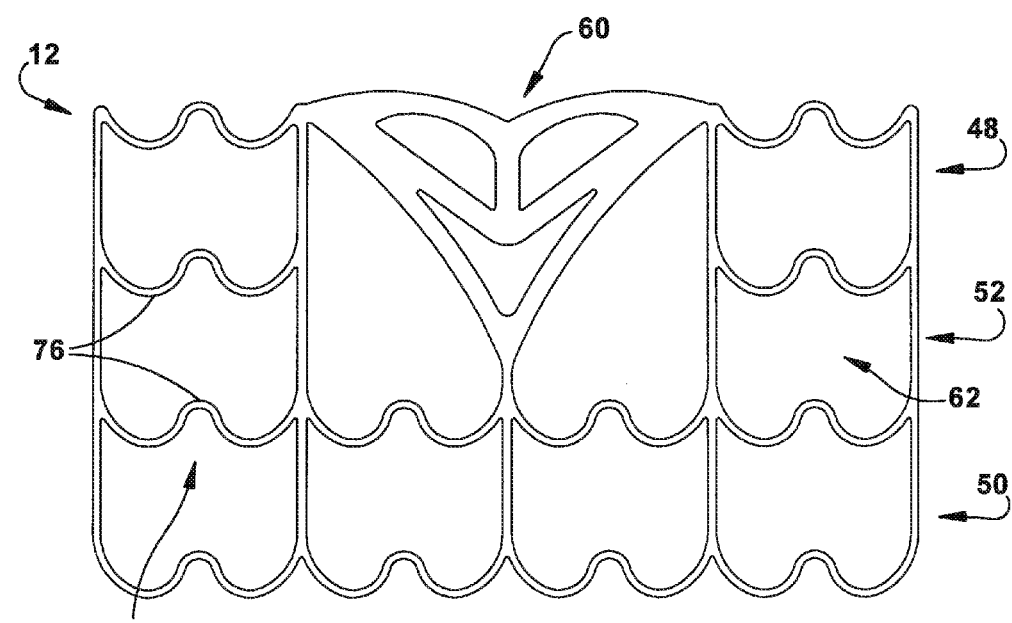
FIG. 6B is an exploded plan view showing another alternative configuration of the of the expandable region in FIG. 6A.
Figure 6C:
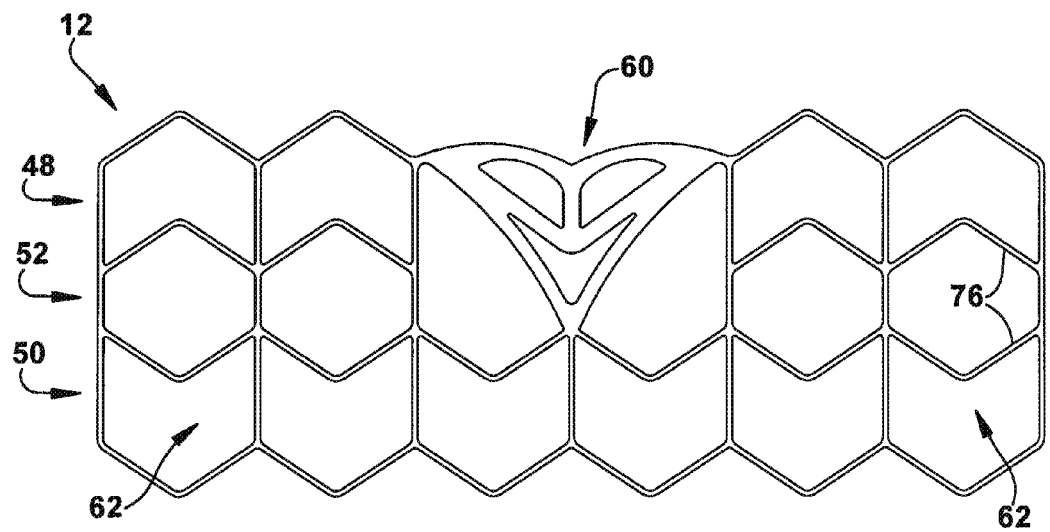
FIG. 6C is an exploded plan view showing another alternative configuration of the of the expandable region in FIG. 6B.
Figure 6D:
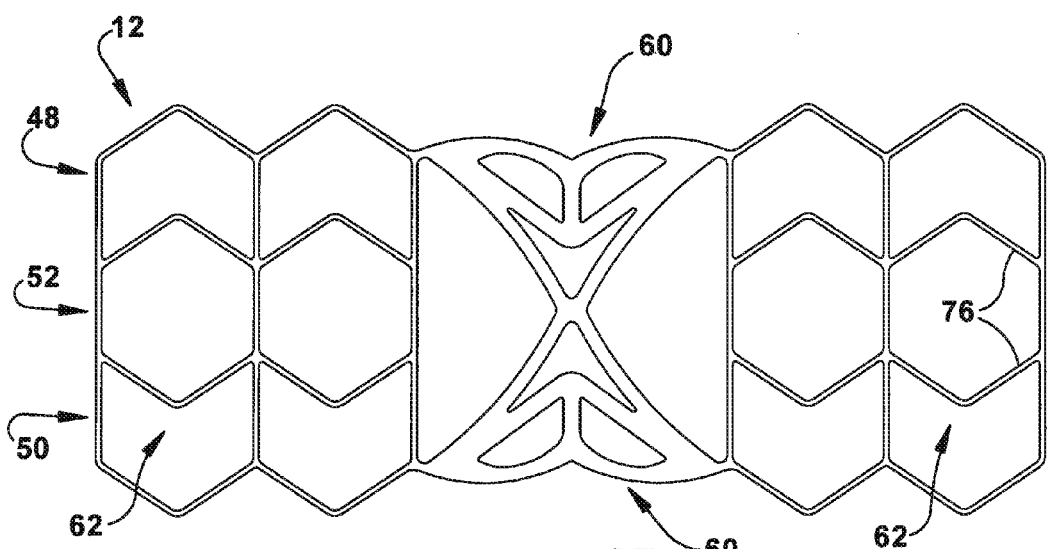
FIG. 6D is an exploded plan view showing another alternative configuration of the of the expandable region in FIG. 6C.
Figure 6E:
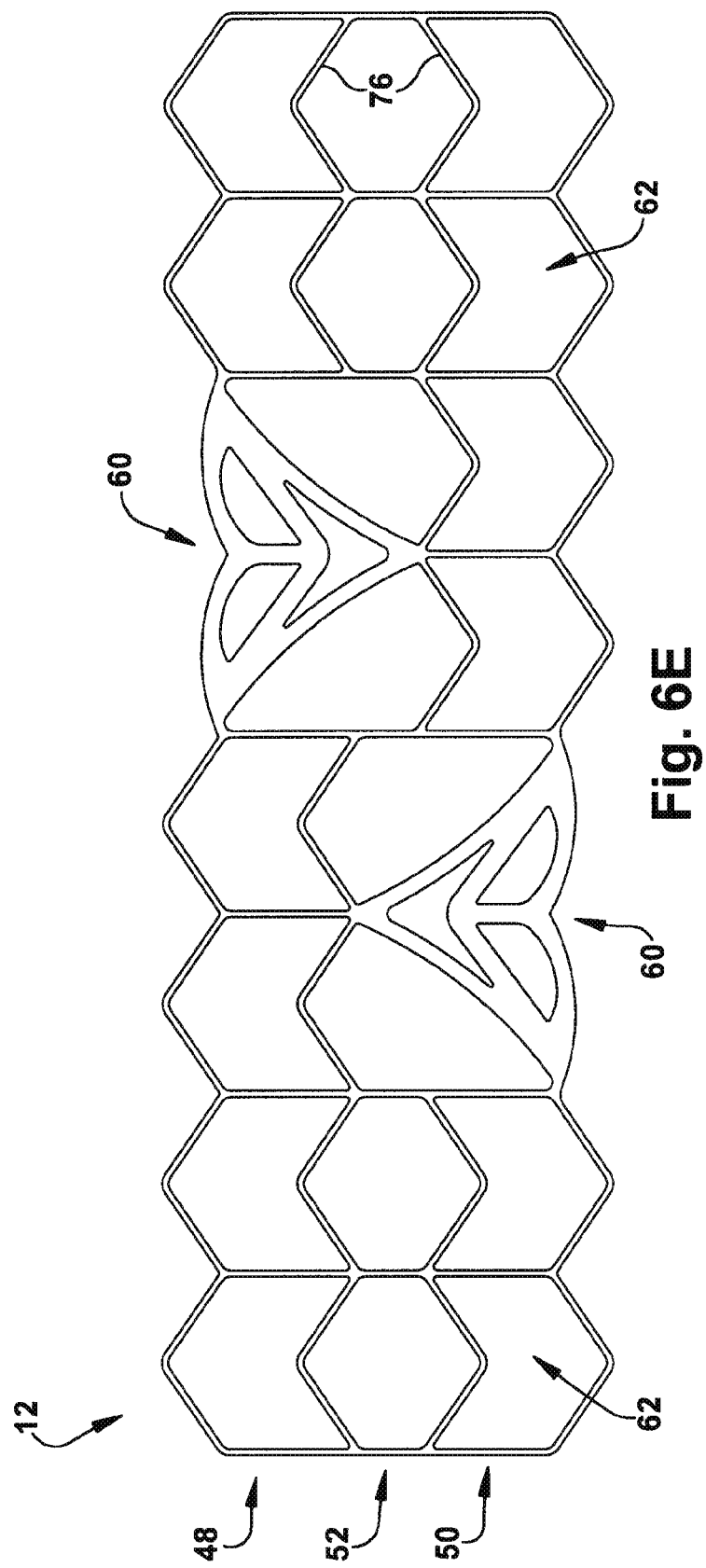
FIG. 6E is an exploded plan view showing another alternative configuration of the of the expandable region in FIG. 6D.

As illustrated in FIGS. 5A-6E, each of the expandable regions 62 can additionally or optionally include at least one reinforcing strut member 76. The reinforcing strut member 76 can have a variety of configurations. For example, the reinforcing strut member 76 can be diamond-shaped as shown in FIGS. 5C-D. Additionally or optionally, each of the expandable regions 62 can include two or more strut members 76 that extend substantially parallel to the circumferential axis CA. For example, each of the expandable regions 62 can include a plurality of M-shaped (FIG. 6A), W-shaped (FIG. 6B), or A-shaped strut members 76 (FIGS. 6C-E).

Figure 7:
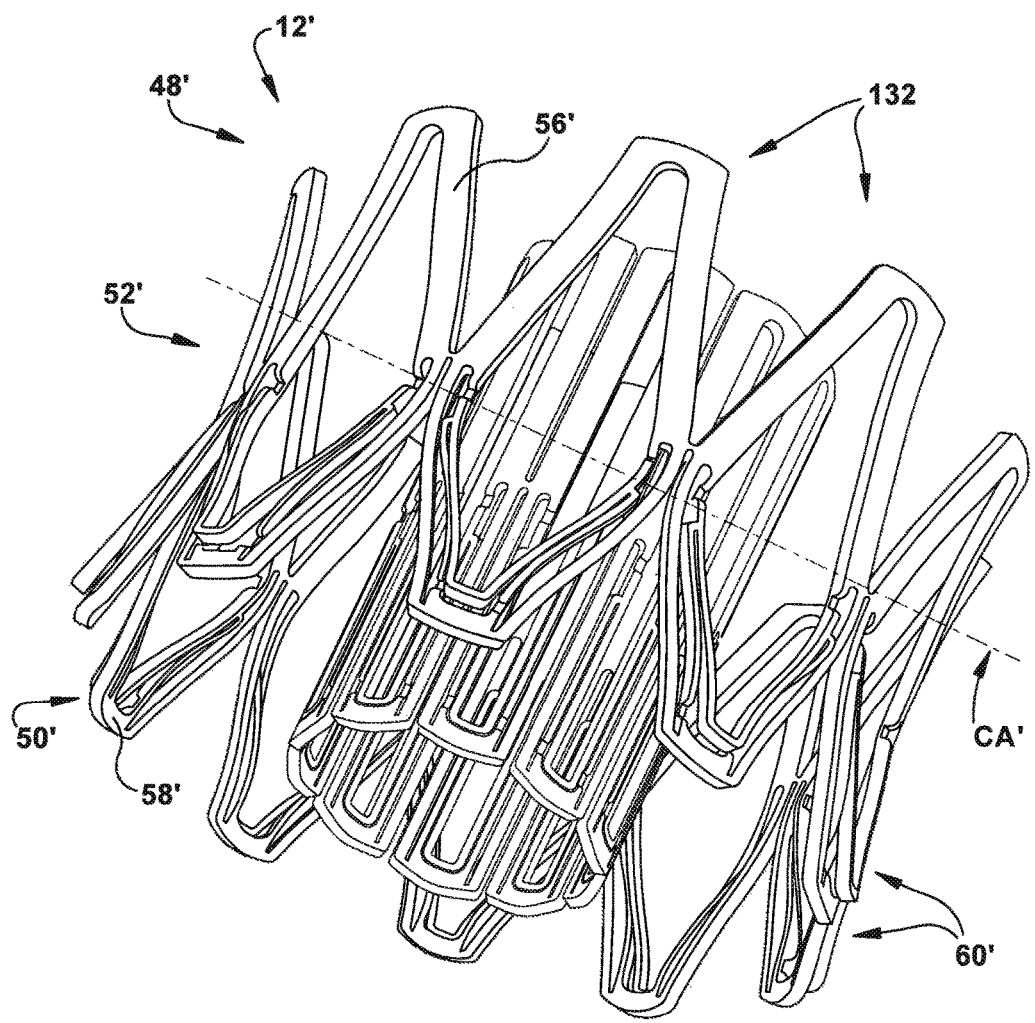
FIG. 7 is a perspective view showing an alternative configuration of the expandable support member in FIGS. 3A-B comprising a plurality of expandable units.
Figure 8:
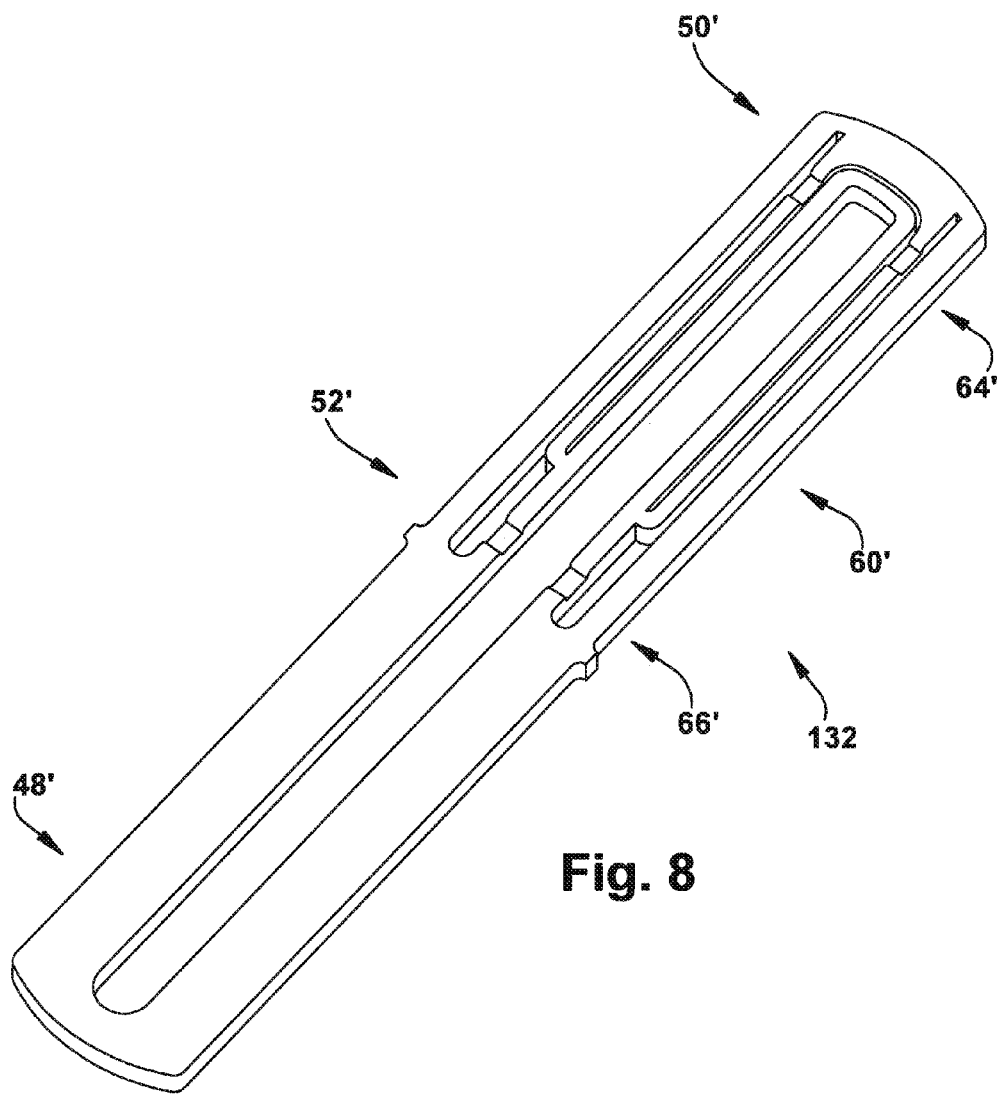
FIG. 8 is a perspective view showing one of the expandable units in FIG. 7 in a radially collapsed configuration.

FIGS. 7-8 illustrate an expandable support member 12' constructed with a similar configuration as the expandable support member 12 illustrated in FIGS. 3A-B. As shown in FIG. 7, the expandable support member 12' can be generally annular in shape and have oppositely disposed first and second end portions 48' and 50' and a main body portion 52' extending between the end portions. Additionally, the expandable support member 12' can have a saddle-shaped, 3D configuration to mimic the 3D shape of a diseased cardiac valve (FIG. 3C). The expandable support member 12' (FIG. 7) can have a flexible configuration to facilitate transition between a radially collapsed configuration and a radially expanded configuration. All or only a portion of the expandable support member 12' may be made from a medical grade metal or plastic, including shape memory materials, such as Nitinol, stainless steel, and/or titanium. For example, all or only a portion of the expandable support member 12' may be made of a Co—Cr alloy, such as Co-20Cr-15W-10Ni. The expandable support member 12' may be self-expandable or mechanically expandable (e.g., using a balloon), depending upon the material used to construct the expandable support member. Additionally, at least a portion of the expandable support member 12' may be made from a bioabsorbable material, such as a magnesium alloy, dendrimers, biopolymers (e.g., thermoplastic starch), polylactides, cellulose, and aliphatic aromatic copolyesters.

The main body portion 52' can extend between the first and second end portions 48' and 50' and include an outer circumferential surface 56' oppositely disposed from an inner circumferential surface 58'. As shown in FIG. 7, a circumferential axis CA' extends about or around the outer circumferential surface 56', approximately between the first and second end portions 48' and 50' of the expandable support member 12'.

The expandable support member 12' can be made from a plurality of interconnected, expandable units 132 (FIG. 8). In the radially collapsed configuration, each of the units 132 has a rectangular configuration; whereas each of the units has trapezoidal configuration (FIG. 7) in the radially expanded configuration. The second end portion 50' of each of the expandable units 132 can include a W-shaped wing member 60' having a first end portion 64' and a spaced apart, flexible second end portion 66'.

The first end portion 64' of each of the wing members 60' can be substantially adjacent the second end portion 50' of the expandable support member 12'. The first end portion 64' of each of the wing members 60' can be sharpened or dull (e.g., arrow or fish hook-shaped). It should be appreciated that the first end portion 64' of each of the wing members 60' can include at least one attachment mechanism (not shown) to facilitate attachment and positioning of the expandable support member 12' in the annulus (not shown in detail) of the diseased cardiac valve 16. For example, the attachment mechanism can include at least one barb, hook, or other similar means for embedding into a section of cardiac tissue (e.g., annular tissue, valve leaflet, chordae, etc.).

The second end portion 66' of each of the wing members 60' can be integrally formed with a portion of the main body portion 52'. As shown in FIGS. 7-8, for example, the second end portion 66' of each of the wing members 60' can be integrally formed with the main body portion 52' near the circumferential axis CA'. The first end portion 64' of the wing members 60', the second end portion 66' of the wing members, or both, can additionally or optionally include a plurality of openings (not shown) to facilitate attachment of the prosthetic valve 14 to the expandable support member 12'.

The second end portion 66' of each of the wing members 60' is resiliently bendable to allow the first end portion 64' to radially expand relative to the outer circumferential surface 56'. As shown in FIG. 7, for example, the first end portion 64' of each of the wing members 60' can be substantially flush with the outer circumferential surface 56' when the expandable support member 12' is in the radially collapsed configuration. Additionally, the first end portion 64' of each of the wing members 60' can extend substantially radial to both the circumferential axis CA' and the outer circumferential surface 56' when the expandable support member 12' is in the radially expanded configuration.

It will be appreciated that the expandable support member 12' can include any number, size, and configuration of wing members 60'. For example, the expandable support member 12' can include a plurality of wing members 60' spaced around only the first end portion 48' or, alternatively, a plurality of wing members spaced around both the first end portion and the second end portion 50'. It will also be appreciated that the expandable support member 12' can additionally or optionally include at least one reinforcing strut member 76, as shown in FIGS. 5A-6E and described above. Although the expandable support member 12' is shown as having wing members 60 and 60' at both the first and second end portions 48' and 50', it should be appreciated that only the first end portion or only the second end portion of the expandable support member may include a plurality of wing members.

It will be appreciated that the expandable support member 12 and 12' can include a layer of biocompatible material (not shown) separately covering at least a portion of the expandable support member and/or one or more of the wing members 60 and 60'. The layer of biocompatible material may be synthetic, such as DACRON (Invista, Wichita, Kans.), woven velour, polyurethane, polytetrafluoroethylene (PTFE), expanded PTFE, GORE-TEX (W. L. Gore & Associates, Flagstaff, Ariz.), or heparin-coated fabric. Alternatively, the layer may be a biological material, such as bovine, porcine or equine pericardium, peritoneal tissue, an allograft, a homograft, a patient graft, or a cell-seeded tissue. The layer may be attached around the outer circumferential surface 56 and 56' of the expandable support member 12 and 12' in pieces or interrupted sections to allow the wing members 60 and 60' to easily expand. By covering a portion of the expandable support member 12 and 12' with a layer of biocompatible material, the hemocompatibility of the apparatus 10 may be improved.

The expandable support member 12 and 12' may additionally or optionally include at least one therapeutic agent for eluting into the cardiovascular tissue and/or blood stream. The therapeutic agent may be capable of preventing a variety of pathological conditions including, but not limited to, hypertension, hypotension, arrhythmias, thrombosis, stenosis and inflammation. Accordingly, the therapeutic agent may include at least one of an anti-arrhythmic agent, an anti-hypertensive, an anti-hypotensive agent, an anticoagulant, an antioxidant, a fibrinolytic, a steroid, an anti-apoptotic agent, an anti-mineralization agent, an anti-calcification agent, and/or an anti-inflammatory agent.

Optionally or additionally, the therapeutic agent may be capable of treating or preventing other diseases or disease processes, such as microbial infections and heart failure. In these instances, the therapeutic agent may include an inotropic agent, a chronotropic agent, an anti-microbial agent, and/or a biological agent such as a cell, peptide, or nucleic acid. The therapeutic agent can be linked to a surface of the expandable support member 12 and 12', embedded and released from within polymer materials, such as a polymer matrix, or surrounded by and released through a carrier.

As shown in FIGS. 1A-B, the prosthetic valve 14 is secured within the main body portion 52 of the expandable support member 12 by sutures or other suitable means. In one example of the present invention, the prosthetic valve 14 can comprise a stentless, substantially dehydrated bioprosthetic valve. By "stentless" it is meant that the leaflets of the prosthetic valve 14 are not reinforced with a support structure, such as a stent or other similar structure. Other examples of prosthetic valves are known in the art, such as the valves disclosed in U.S. Pat. No. 5,156,621, which is hereby incorporated by reference in its entirety.

A substantially dehydrated bioprosthetic valve 14 may be fixed and preserved using a variety of known methods. The use of chemical processes for the fixation and preservation of biological tissues have been described and are readily available in the art. For example, glutaraldehyde, and other related aldehydes have seen widespread use in preparing cross-linked biological tissues. Glutaraldehyde is a five carbon aliphatic molecule with an aldehyde at each end of the chain, rendering it bifunctional. These aldehyde groups react under physiological conditions with primary amine groups on collagen molecules resulting in the cross-linking of collagen containing tissues. Methods for glutaraldehyde fixation of biological tissues have been extensively described and are well known in the art. In general, a tissue sample to be cross-linked is simply contacted with a glutaraldeyde solution for a duration effective to cause the desired degree of cross-linking within the biological tissue being treated.

Many variations and conditions have been applied to optimize glutaraldehyde fixation procedures. For example, lower concentrations have been found to be better in bulk tissue cross-linking compared to higher concentrations. It has been proposed that higher concentrations of glutaraldehyde may promote rapid surface cross-linking of the tissue, generating a barrier that impedes or prevents the further diffusion of glutaraldehdye into the tissue bulk. For most bioprosthesis applications, the tissue is treated with a relatively low concentration glutaraldehyde solution, e.g., typically between 0.1%-5%, for 24 hours (or more) to ensure optimum fixation. Various other combinations of glutaraldehyde concentrations and treatment times will also be suitable depending on the objectives for a given application. Examples of such other combinations include, but are not limited to, U.S. Pat. Nos. 6,547,827, 6,561,970, and 6,878,168, all of which are hereby incorporated by reference in their entirety.

In addition to bifunctional aldehydes, many other chemical fixation procedures have been described. For example, some methods employ polyethers, polyepoxy compounds, diisocyanates, and azides. These and other approaches available to the skilled individual in the art for treating biological tissues are suitable for cross-linking vascular graft tissue according to the present invention.

The substantially dehydrated bioprosthetic valve 14 may also be treated and preserved with a dry tissue valve procedure as described in U.S. Pat. No. 6,534,004, the entire contents of which are hereby incorporated by reference. Furthermore, the substantially dehydrated bioprosthetic valve 14 may be treated with anti-calcification solutions, such as XENOLOGIX treatment (Edwards Lifesciences, Irvine, Calif.) or the SYNERGRAF (CryoLife, Inc., Kennesaw, Ga.) treatment process, and/or anti-calcification agents, such as a-amino oleic acid.

The substantially dehydrated bioprosthetic valve 14 can be made with one piece of pericardial tissue, for example. Where a single piece of pericardial tissue is used, a seam may be formed by suturing the ends of the tissue. Alternatively, the substantially dehydrated bioprosthetic valve 14 can be made with two pieces of pericardial tissue, one of which will form the first leaflet and the other forms the second leaflet of the valve. Where two pieces of pericardial tissue are used, it is necessary to suture the tissue in two locations, thereby forming two seams. The seams are always placed at what will be the commissural sections of the valve 14, where the first leaflet meets the second leaflet. It will be appreciated that the prosthetic valve 14 can be made with three or more pieces of tissue as well.

Figure 9:
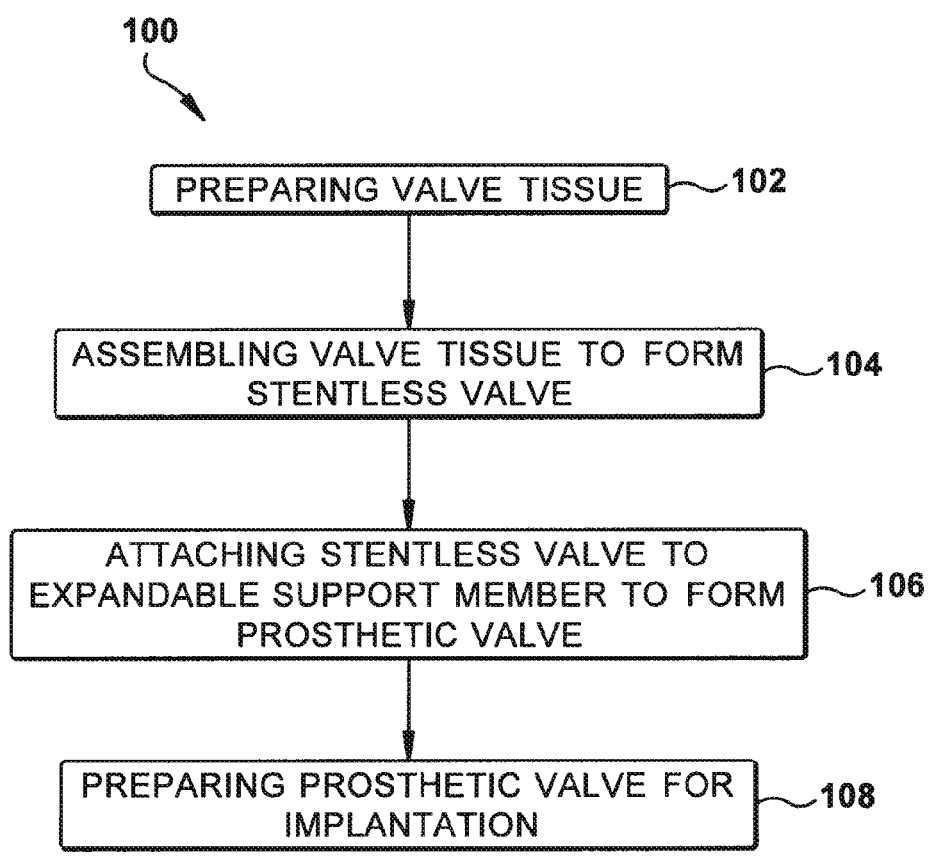
FIG. 9 is a process flow diagram illustrating a method for forming a prosthetic valve according to another aspect of the present invention.

Another method 100 for making the prosthetic valve 14 (e.g., a substantially dehydrated bioprosthetic valve) is illustrated in FIG. 9. As shown in FIG. 9, one step of the method 100 can include preparing valve tissue 110 (FIG. 10A) at Step 102. The valve tissue used to prepare the prosthetic valve 14 can comprise any one or combination of biological tissue(s), such as bovine, porcine or equine pericardium, peritoneal tissue, an allograft, a homograft, a patient graft, or a cell-seeded tissue. The valve tissue 110 can be chemically-treated (e.g., cross-linked) prior to use (as described above). For example, the tissue 110 used to form the prosthetic valve 14 can comprise cross-linked equine pericardium tissue.

Figure 10:
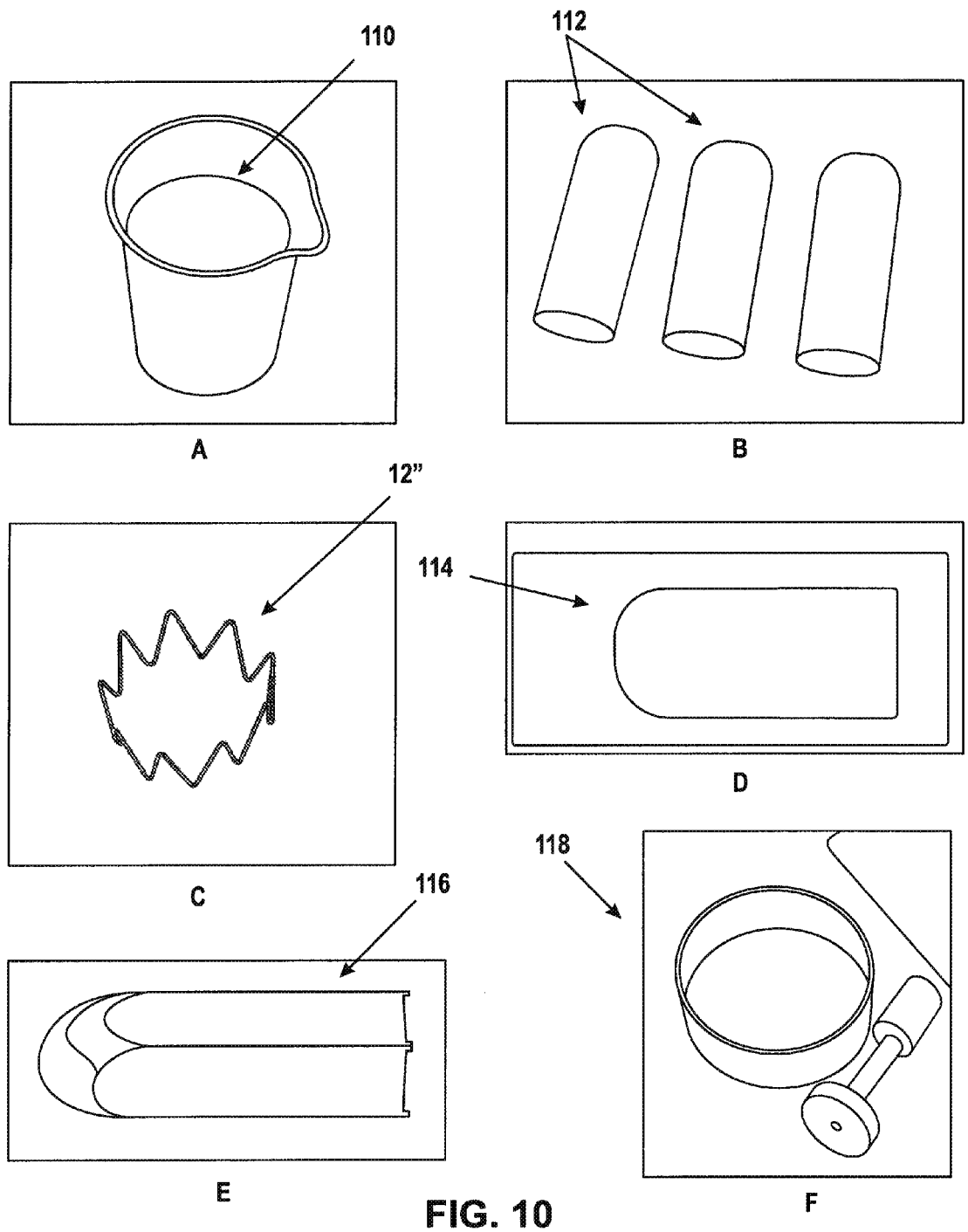
FIG. 10A is valve tissue in a beaker used to prepare the prosthetic valve according to the method of FIG. 9.
FIG. 10B is three valve molds used to prepare the prosthetic valve according to the method of FIG. 9.
FIG. 10C is an alternative configuration of the expandable support member in FIGS. 3A-B used to prepare the prosthetic valve according to the method of FIG. 9.
FIG. 10D shows sutures used to prepare the prosthetic valve according to the method of FIG. 9.
FIG. 10E shows a valve leaflet support member used to prepare the prosthetic valve according to the method of FIG. 9.
FIG. 10F shows a holding clamp used to prepare the prosthetic valve according to the method of FIG. 9.

To prepare the valve tissue 110, a variety of materials and components can first be assembled. As shown in FIGS. 10A-F, the materials and components can include the valve tissue 110 (FIG. 10A), a plurality of valve molds 112 (FIG. 10B), an expandable support member 12" (FIG. 10C), sutures 114 (FIG. 10D) (e.g., 4-0 prolene sutures), a silicone valve leaflet support member 116 (FIG. 10E), and a holding clamp 118 (FIG. 10F). Although the expandable support member 12" shown in FIG. 10C has a W-shaped configuration, it will be appreciated that the expandable support member can have any other desired configuration, such as the configuration of the expandable support member 12 and 12' shown in FIGS. 1A-B and FIGS. 7-8 (respectively). Other materials and components that may be needed for the method 100 can include one or more scalpels 120 (FIG. 17), one or more hemostats (not shown), one or more surgical towels 122 (FIG. 12), and scissors 124.

Figure 11:
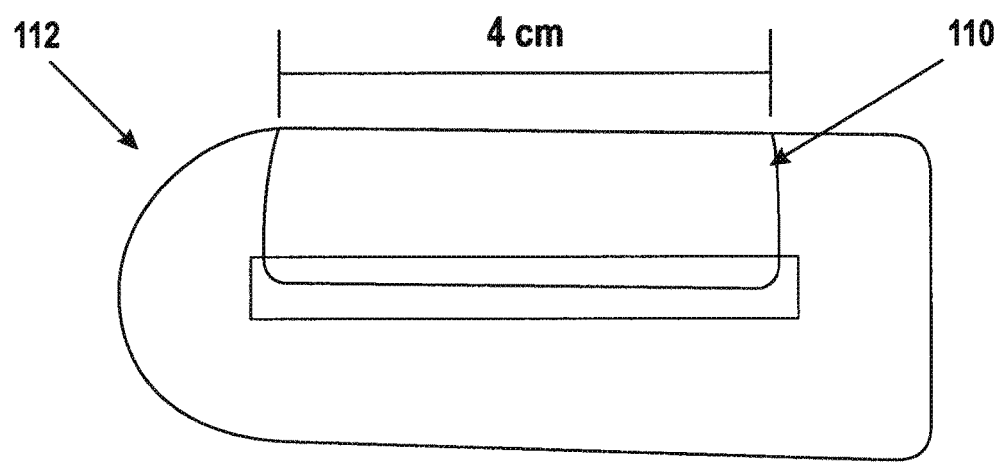
FIG. 11 shows the valve tissue in FIG. 10A wrapped around one of the valve molds.
Figure 12:
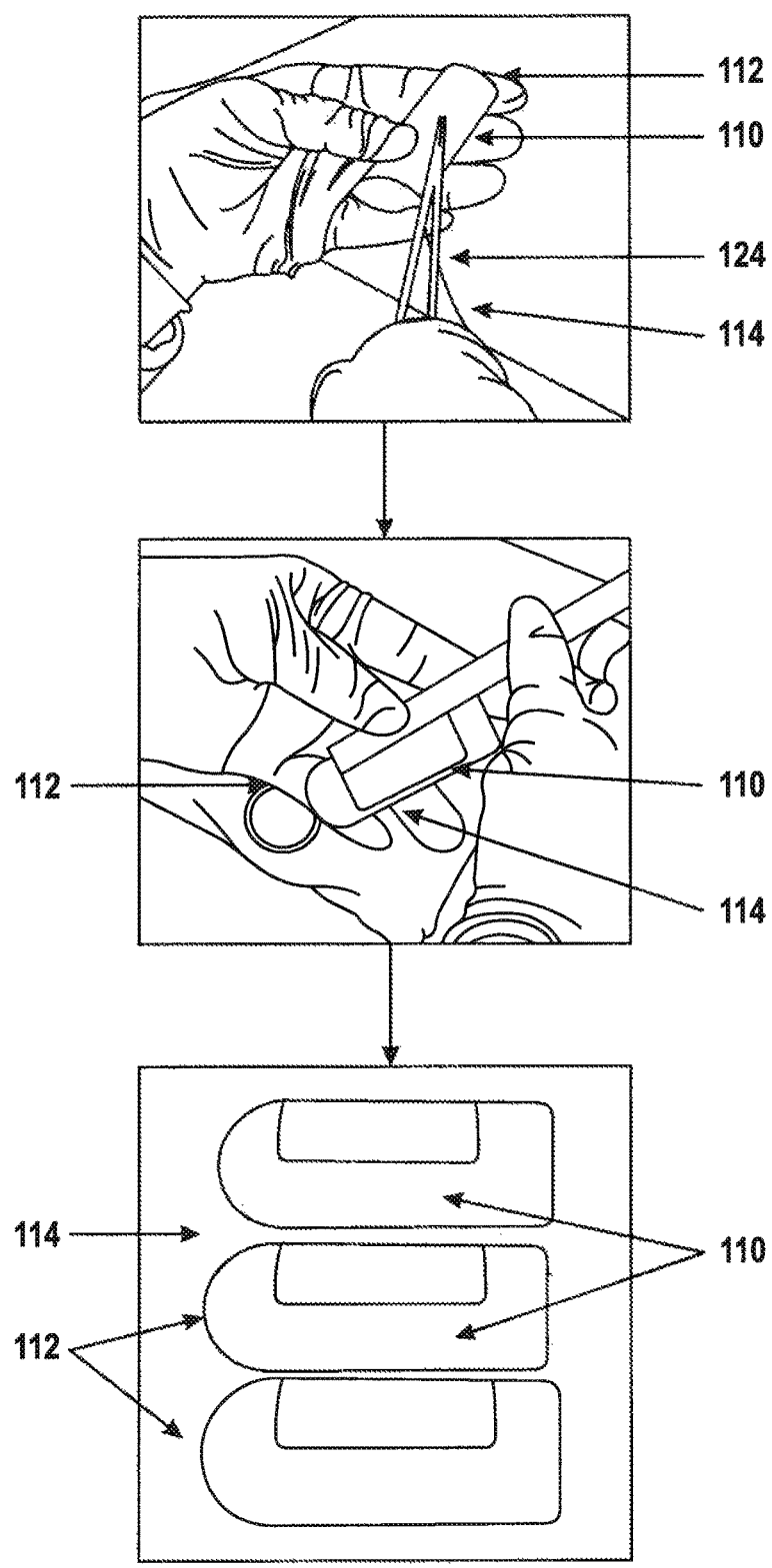
FIG. 12 shows the valve tissue in FIG. 11 being sutured about the valve mold.

To prepare the valve tissue 110 (e.g., cross-linked equine pericardium) (FIG. 11), the tissue is measured and cut into a number of strips equal to the number of valve molds 112. For example, three strips of tissue 110 each having a width of about 4 cm can be prepared. As shown in FIG. 11, each of the tissue strips 110 can then be wrapped around a separate one of the valve molds 112. The tissue 110 can then be trimmed (e.g., using a surgical knife) such that the two ends of the tissue meet without any overlap (indicated by boxed region in FIG. 11). The ends of each of the tissue strips 110 can then be sutured to form a sleeve-like configuration around each of the valve molds 112. As shown in FIG. 12, for example, suturing can begin with three or four knots 114 followed by the first stitch. The suture 114 density can be controlled within about 1.25 mm to about 1.5 mm per stitch, and each stitch can be about 3 mm wide.

Figure 13:
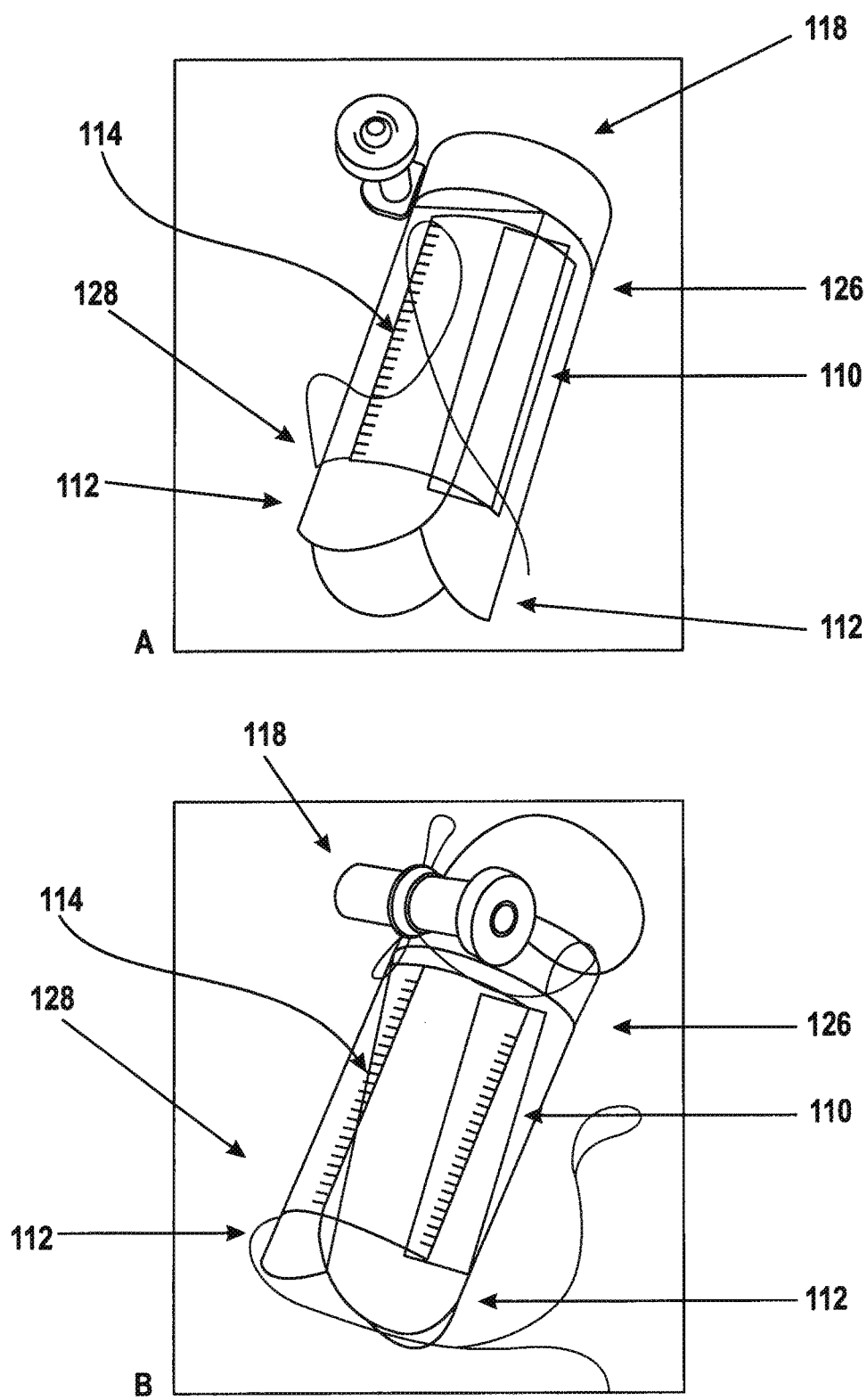
FIG. 13A shows each of the valve molds and corresponding valve tissue sections joined together with the holding clamp in FIG. 10F.
FIG. 13B shows the valve tissue sections in FIG. 13A being sutured together.

At Step 104, the valve tissue 110 can be sewn together to form a stentless valve. As shown in FIG. 13A, formation of the stentless valve can begin by joining each of the valve molds 112 together such that each suturing line is aligned with an exterior midline of each of the valve molds. Next, the holding clamp 118 is placed around one end of each of the valve molds 112 to form a high end 126 and a low end 128. As indicated by the boxed region in FIGS. 13A-B, each of the tissue sleeves 110 is positioned adjacent one another and then sutured. The suture 114 can start with about 3 to four knots, which serve as an alignment point for the expandable support member 12". The suture 114 density can be controlled within about 1.25 mm to about 1.5 mm per stitch, and each stitch can be about 3 mm wide. About 3 mm of each of the tissue sleeves 110 at the high end 126 should not be sutured to facilitate later attachment of the stentless valve to the expandable support member 12".

Figure 14:
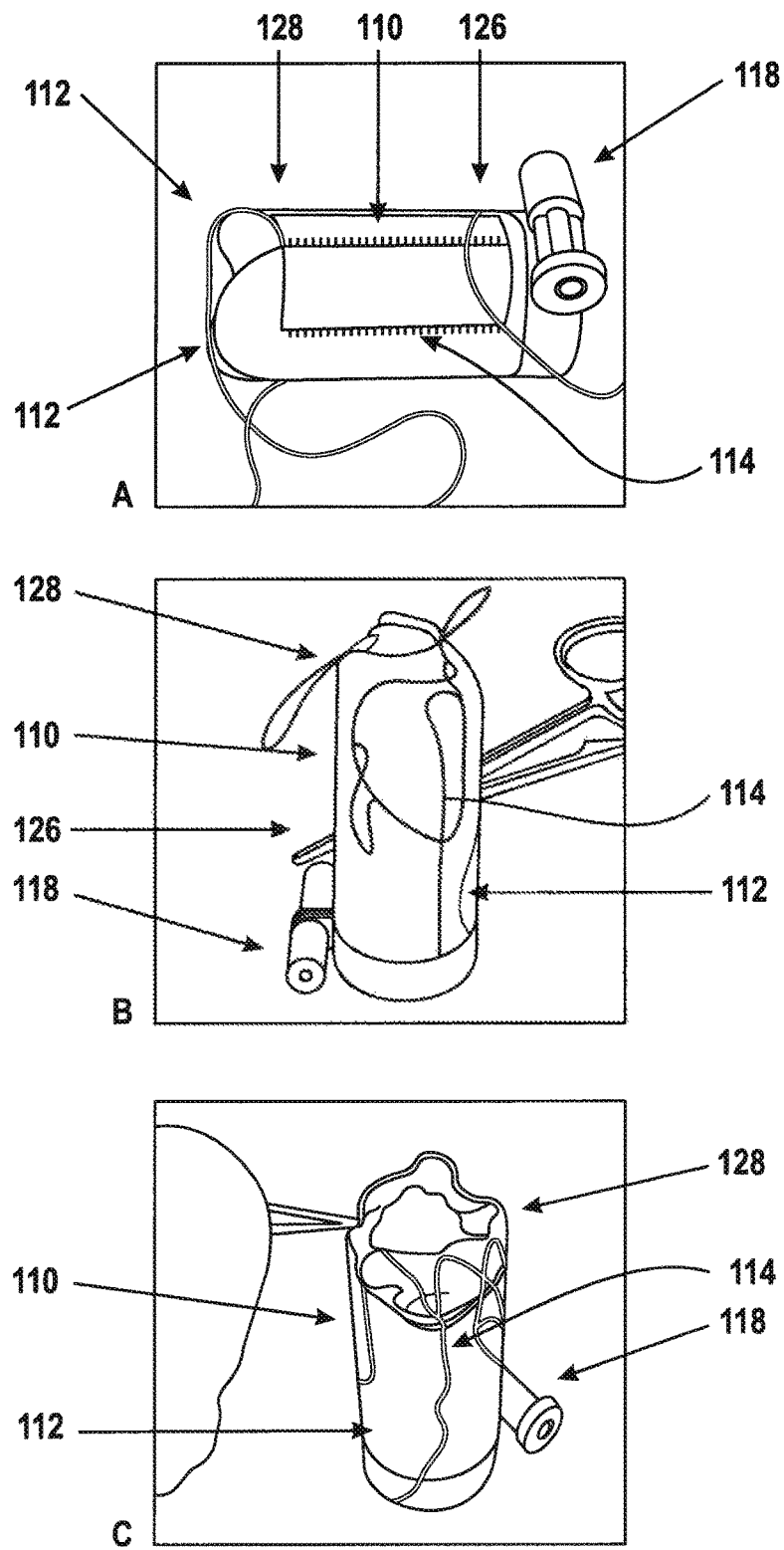
FIG. 14A shows the valve tissue sections in FIG. 13B sutured together.
FIG. 14B shows a low end of the valve tissue in FIG. 14A being sutured together.
FIG. 14C shows the low end of the valve tissue in FIG. 14B being further sutured together.

Next, the low end 128 of the stentless valve can be closed. As shown in FIGS. 14A-C, the tissue 110 can be moved downward (i.e., away from the holding clamp 118) so that a desired amount of the tissue at the low end 128 extends beyond each of the valve molds 112. For example, the tissue 110 can be moved about 15 mm. After moving the tissue 110 downward, the pliable tissue at the low end 128 can be partially closed as shown in FIG. 14C. The suture 114 density can be controlled within about 1.25 mm to about 1.5 mm per stitch, and each stitch can be about 3 mm wide.

Figure 15:
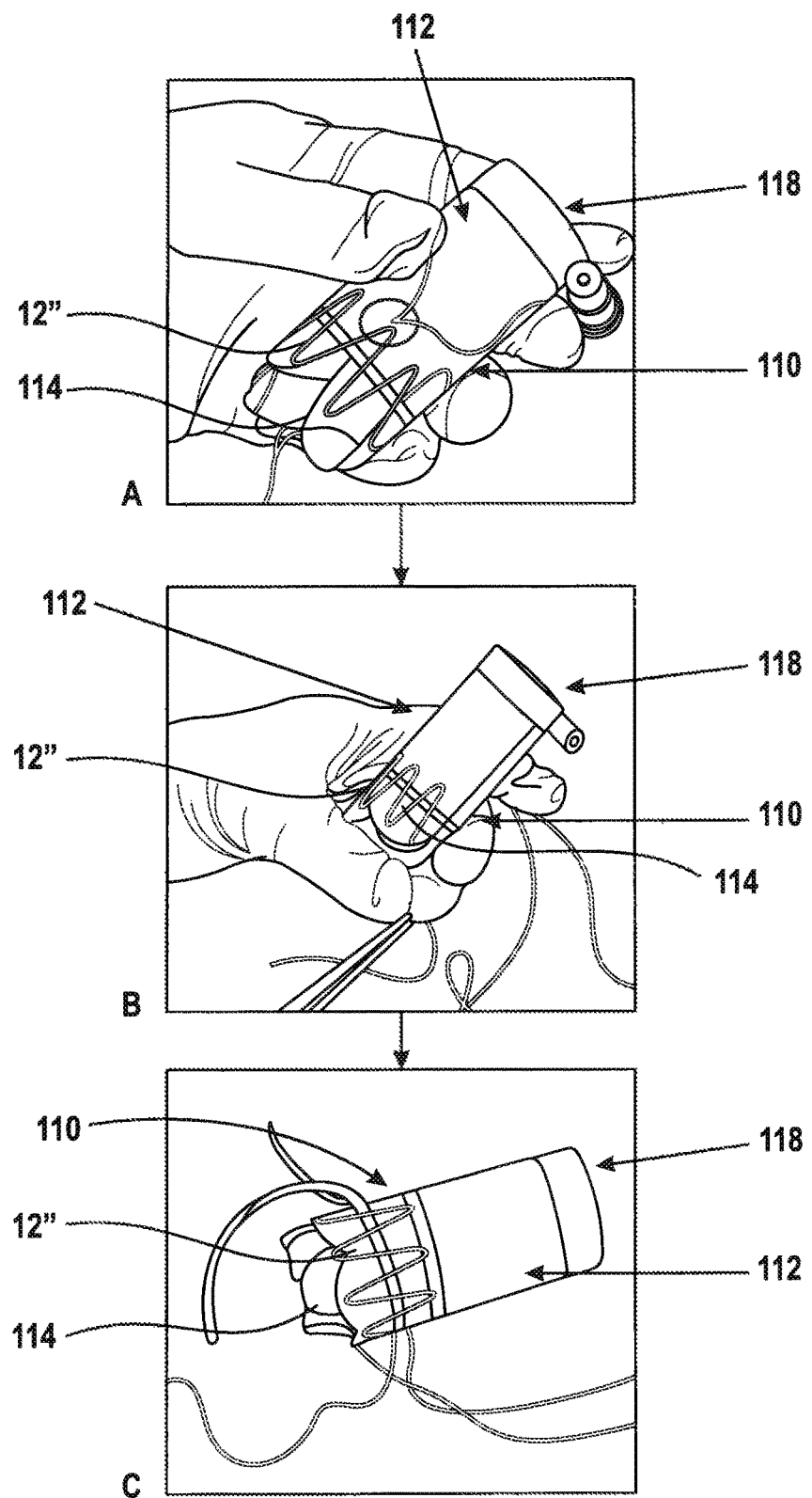
FIG. 15A shows the expandable support member of FIG. 10C being positioned around the valve tissue in FIG. 14C.
FIG. 15B shows a high end of the valve tissue in FIG. 15A being sutured to the expandable support member.
FIG. 15C shows the low end of the valve tissue in FIG. 15B being sutured to the expandable support member.

At Step 106, the stentless valve can be attached to the expandable support member 12". As shown in FIG. 15A, the expandable support member 12" can be evenly positioned over the tissue 110 so that each suture line 114 is aligned with an alternating peak of the expandable support member (indicated by oval in FIG. 15A). Care should be taken to make sure the expandable support member 12" is evenly aligned with the tissue 110. Using the W-shaped expandable support member 12" shown in FIGS. 15A-C, for example, care should be taken to ensure that each tissue section 110 includes three V-shaped "units" of the expandable support member.

As shown in FIG. 15B, the tissue 110 located at the high end 126 can then be flipped downward over a portion of the expandable support member 12" to form a lip. The lip can be carefully sutured to ensure that the suture penetrates all layers of the tissue 110. Additionally, care should be taken to place stitches 114 (e.g., about 3 stitches) on every peak of the expandable support member 12", as well as one or more stitches at every two peak ends. As shown in FIG. 15C, the free tissue 110 at the low end 128 of the expandable support member 12" can then be flipped to form a lip and then sutured to secure the lower end to the expandable support member (as described above).

Figure 16:
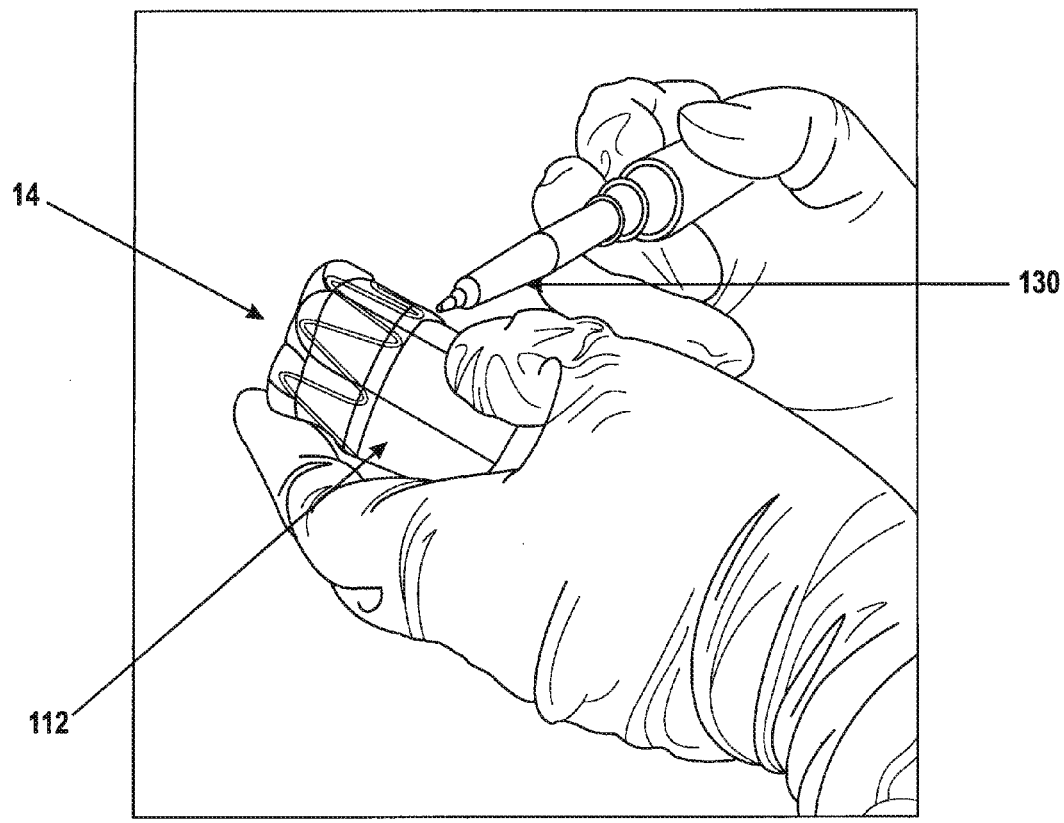
FIG. 16 shows an electric welding tip being used to trim and weld down the expandable support member in FIG. 15C.

After suturing the high and low ends 126 and 128, the newly-formed prosthetic valve 14 can be prepared for implantation at Step 108. Any free end(s) of the suture(s) 114 can be trimmed using scissors 124, for example. The expandable support member 12" can then be trimmed and welded for a sufficient period of time using an electric welding tip 130 (FIG. 16) at about 650° F. to about 660° F. Examples of electric welding devices (not shown) and tips 130 are known in the art and can include the WELLER EC2002M Soldering Station, for example. Next, any unwanted remaining tissue 110 at the low end 128 can be trimmed as needed.

Figure 17:
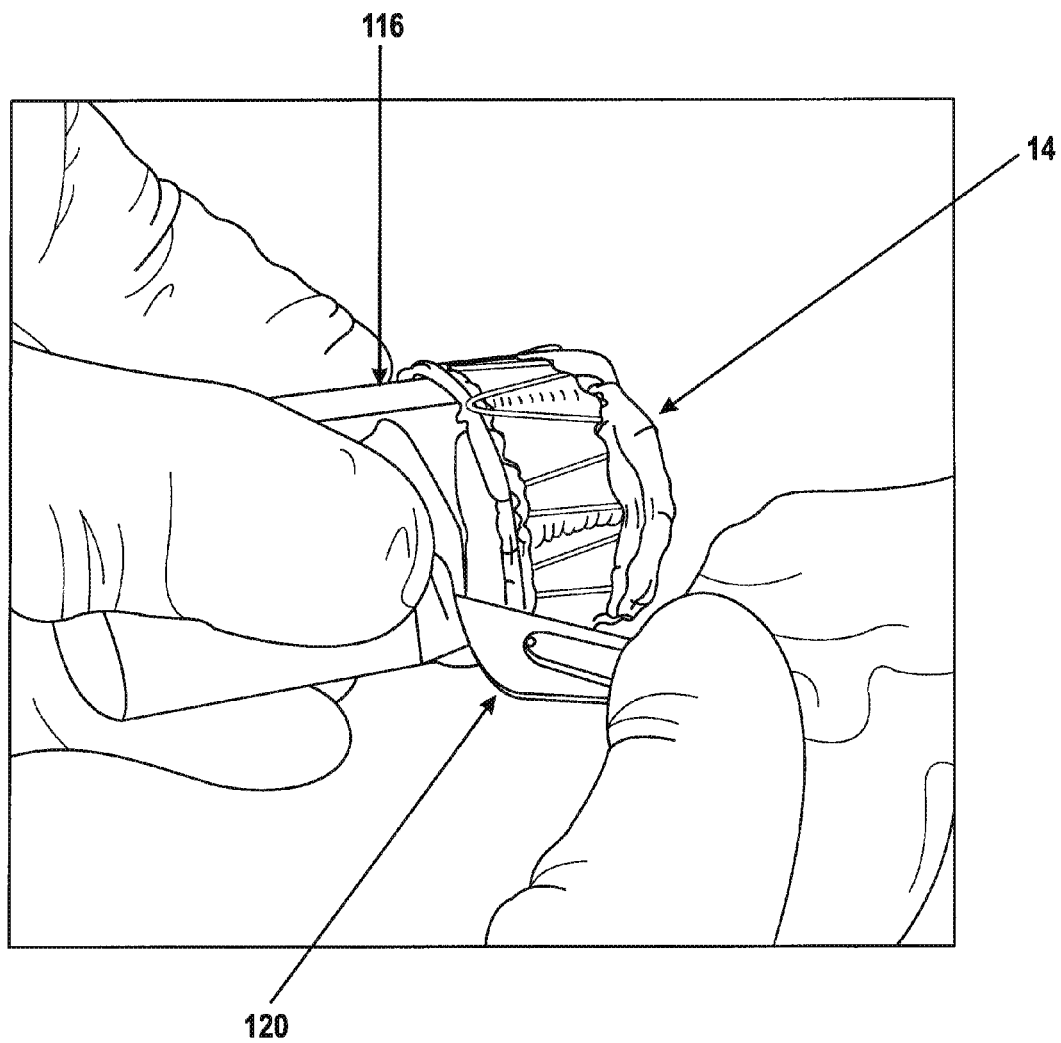
FIG. 17 shows a scalpel the valve leaflet support member of FIG. 10E being used to trim excess valve tissue.

To trim any tissue 110 remaining at the high end 126, the silicone valve leaflet support 116 can be used as shown in FIG. 17. For example, spare tissue 110 can be trimmed using a scalpel 120 (e.g., a #12 scalpel) to make the ends of the leaflets uniform with one another. Additionally, the spare tissue 110 can be trimmed such that each of the leaflets is angled downward (as measured from the circumference to the central axis of the valve 14). For example, each of the leaflets can be trimmed so that the end of each of the leaflets is angled downward at about 2 to 5 degrees. Once the construction of the prosthetic valve 14 has been completed, the valve can be sterilized and stored under wet or dry (i.e., dehydrated) conditions.

Figure 18:
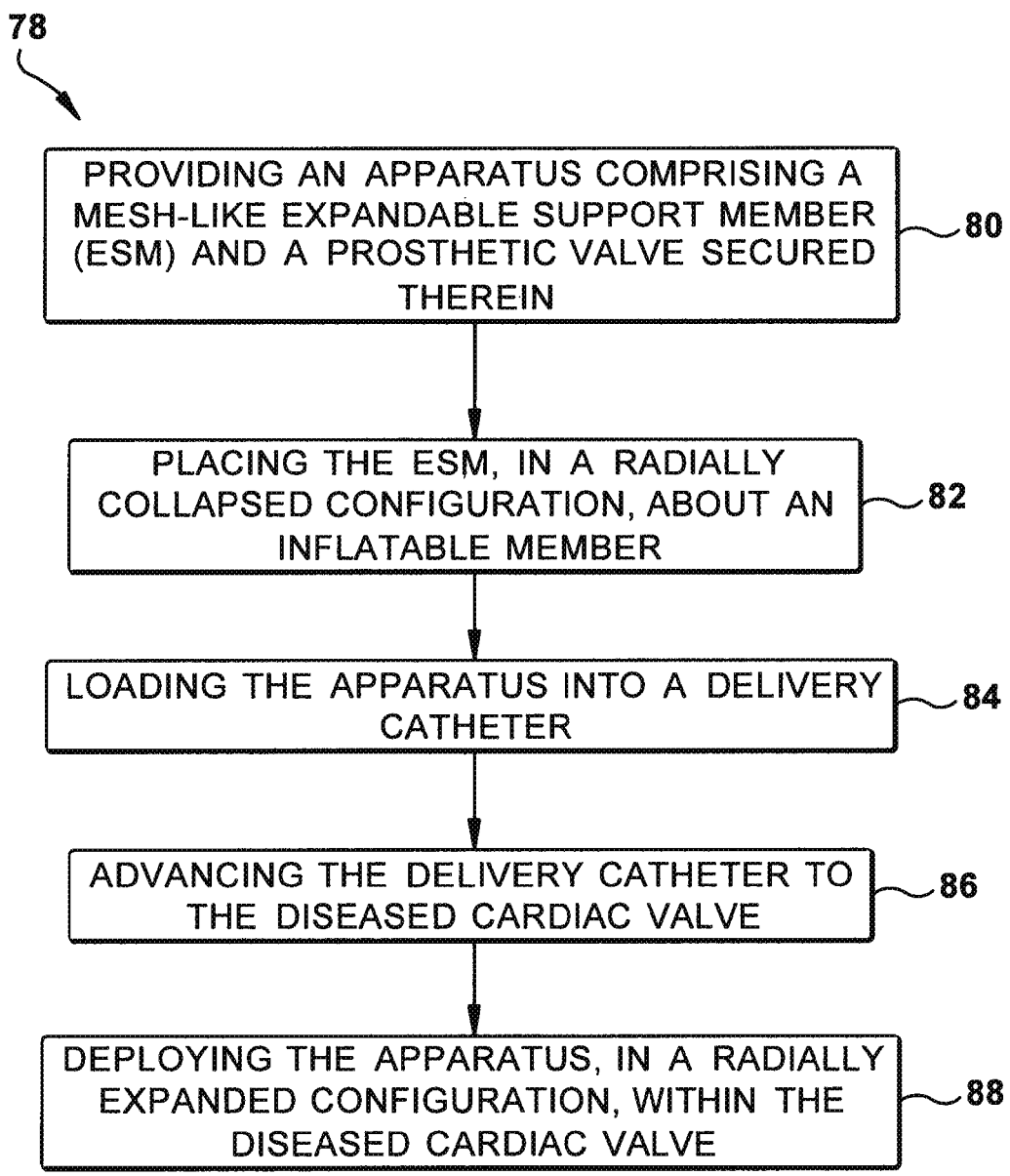
FIG. 18 is a process flow diagram illustrating a method for replacing a diseased cardiac valve according to another aspect of the present invention.

FIG. 18 illustrates another aspect of the present invention comprising a method 78 for replacing a diseased cardiac valve 16, such as a diseased mitral valve 18. Although the method 78 is illustrated below using a percutaneous approach, it will be appreciated that other approaches can be used for replacing the diseased cardiac valve 16. Examples of such alternative approaches can include, but are not limited to, open heart surgery, thoracotomy, thoracoscopic, robotic implantation, left atrial dome insertion, left atrial appendage insertion, transapical insertion, insertion via a pulmonary vein 38, and other minimally invasive techniques known in the art.

One step of the method 78 includes providing an apparatus 10 at Step 80. For example, the apparatus 10 can be constructed as illustrated in FIGS. 1A-4B. Prior to placement of the apparatus 10, the dimensions of the diseased mitral valve 18 are determined using known imaging techniques including, for example, magnetic resonance imaging (MRI), fluoroscopy, echocardiography (e.g., TEE or TTE imaging), computed tomography (CT), angiography, ultrasound, or a combination thereof. After determining the dimensions of the diseased mitral valve 18, an appropriately-sized apparatus 10 having dimensions that correspond to the dimensions of the diseased mitral valve is selected.

To enable delivery and deployment of the apparatus 10 in the diseased mitral valve 18, the apparatus 10 is positioned about an inflatable member 90 (FIG. 23) in the radially collapsed configuration at Step 82. The inflatable member 90 can include a balloon, for example, capable of expanding the main body portion 52 into full and complete contact with the annulus 54 of the diseased mitral valve 18. Additionally, the inflatable member 90 can be shaped to conform to the cross-sectional configuration of the main body portion 52. After securing the apparatus 10 about the inflatable member 90 in the radially collapsed configuration, the apparatus is then loaded into the end of a delivery catheter 92 at Step 84 in a known manner.

Figure 19:
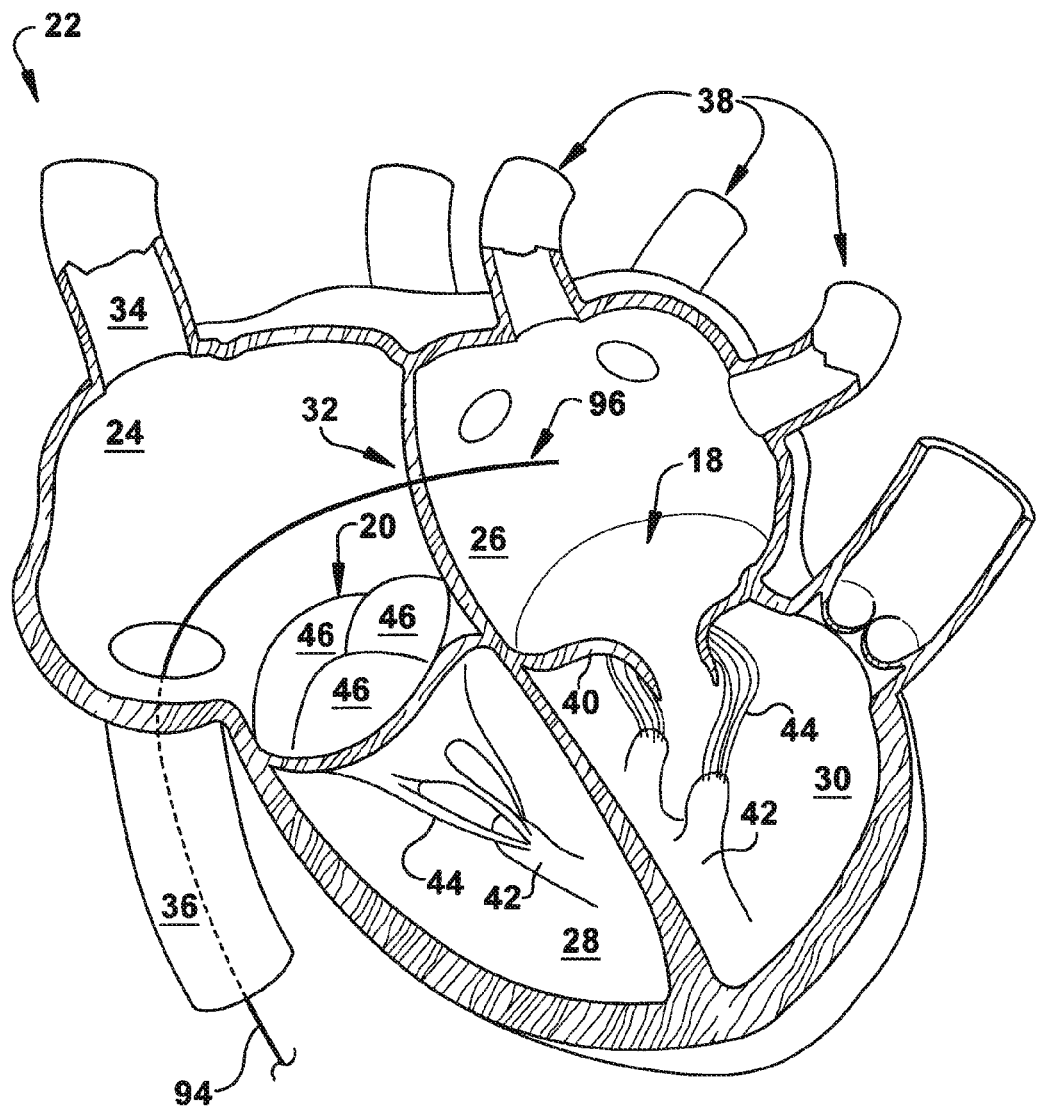
FIG. 19 is a cross-sectional view showing a guidewire extending trans-septally through the human heart of FIG. 2.
Figure 20:
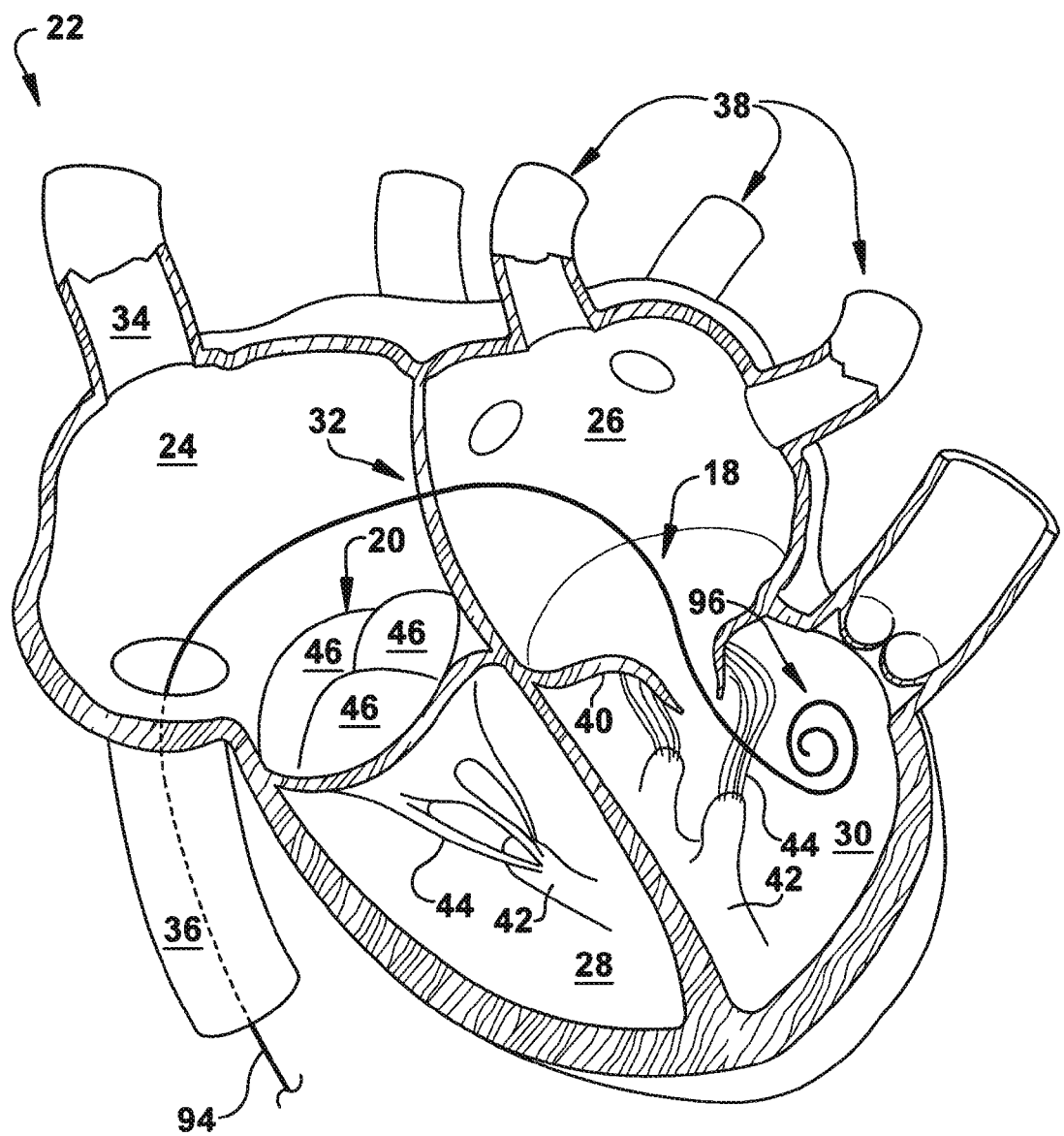
FIG. 20 is a cross-sectional view showing the guidewire in FIG. 19 extending through the mitral valve into the left ventricle.

Next, a guidewire 94 is inserted into the vasculature via a femoral vein (not shown) or jugular vein (not shown) and, under image guidance (e.g., fluoroscopy, ultrasound, MRI, CT, angiography, or a combination thereof), respectively steered through the vasculature into the inferior vena cava 36 or superior vena cava 34. The guidewire 94 is then passed across the right atrium 24 so that the distal end 96 of the guidewire pierces the interatrial septum 32 as shown in FIG. 19. The guidewire 94 is extended across the left atrium 26 and then downward through the diseased mitral valve 18 so that the distal end 96 of the guidewire is securely positioned in the left ventricle 30 (FIG. 20).

Figure 21:
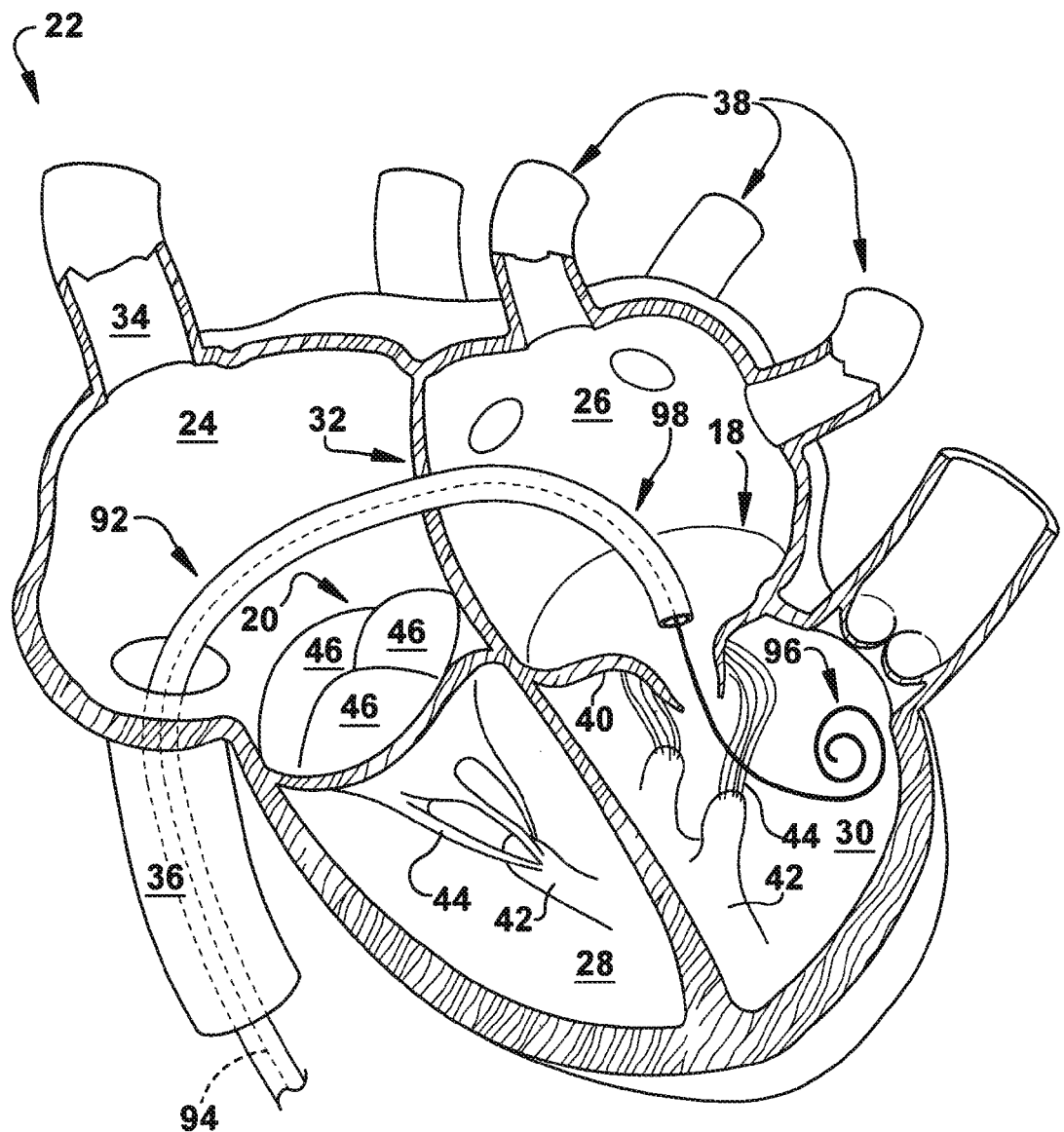
FIG. 21 is a cross-sectional view showing a delivery catheter advanced over the guidewire in FIG. 20.
Figure 22:
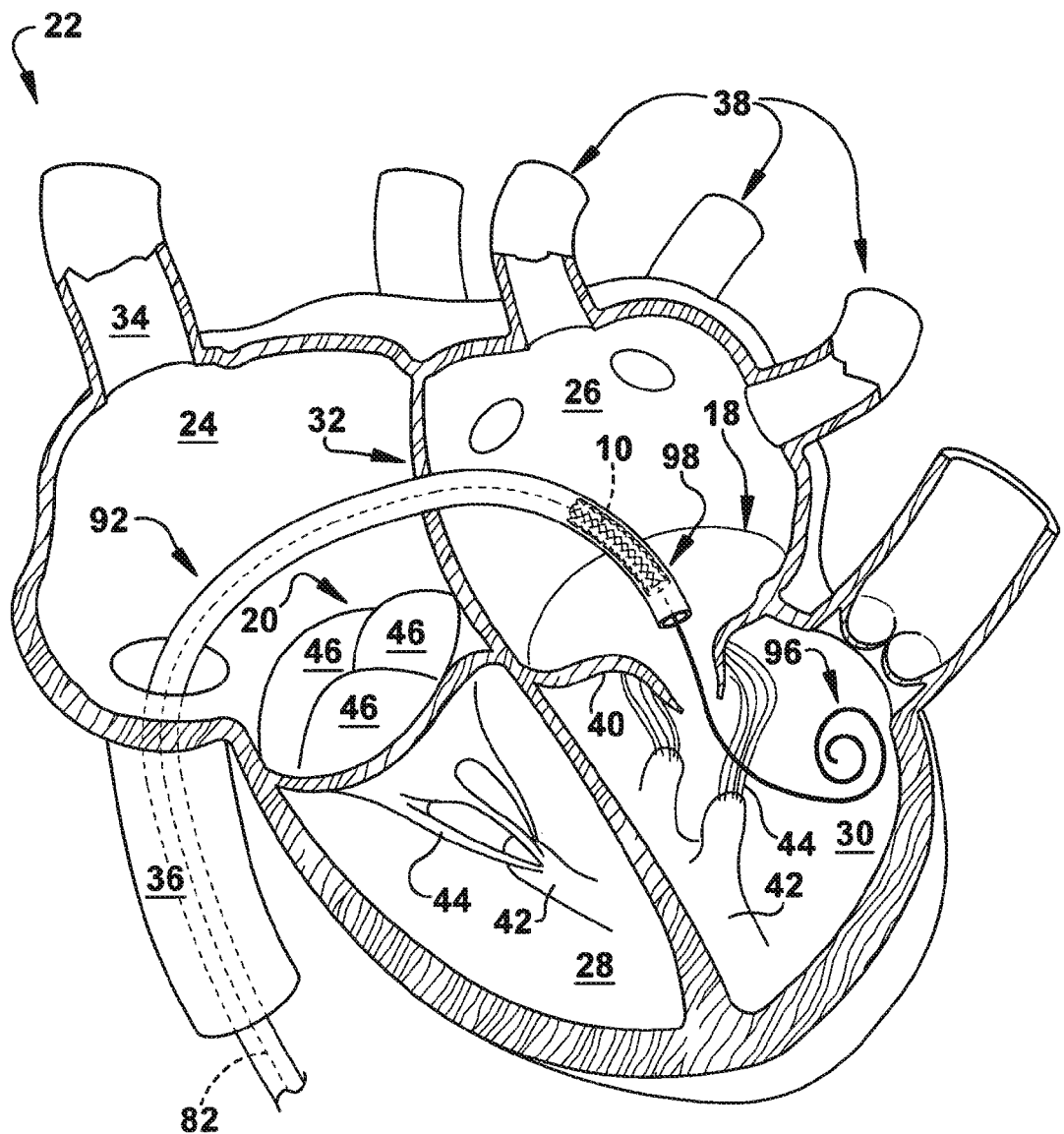
FIG. 22 is a cross-sectional view showing the apparatus of FIG. 1A positioned at the distal end of the delivery catheter in FIG. 21.

After the guidewire 94 is appropriately positioned in the heart 22, the delivery catheter 92 is passed over the guidewire at Step 86 (FIG. 21). After the delivery catheter 92 is positioned as shown in FIG. 21, the apparatus 10 is attached to the proximal end (not shown) of the guidewire 94. A positioning wire (not shown) or other similar device useful for advancing the apparatus 10 over the guidewire 94 is then attached to the apparatus. An axial force is then applied to the positioning wire so that the apparatus 10 is passed over the guidewire 94 and positioned at the distal end 98 of the delivery catheter 92 (FIG. 22).

Figure 23:
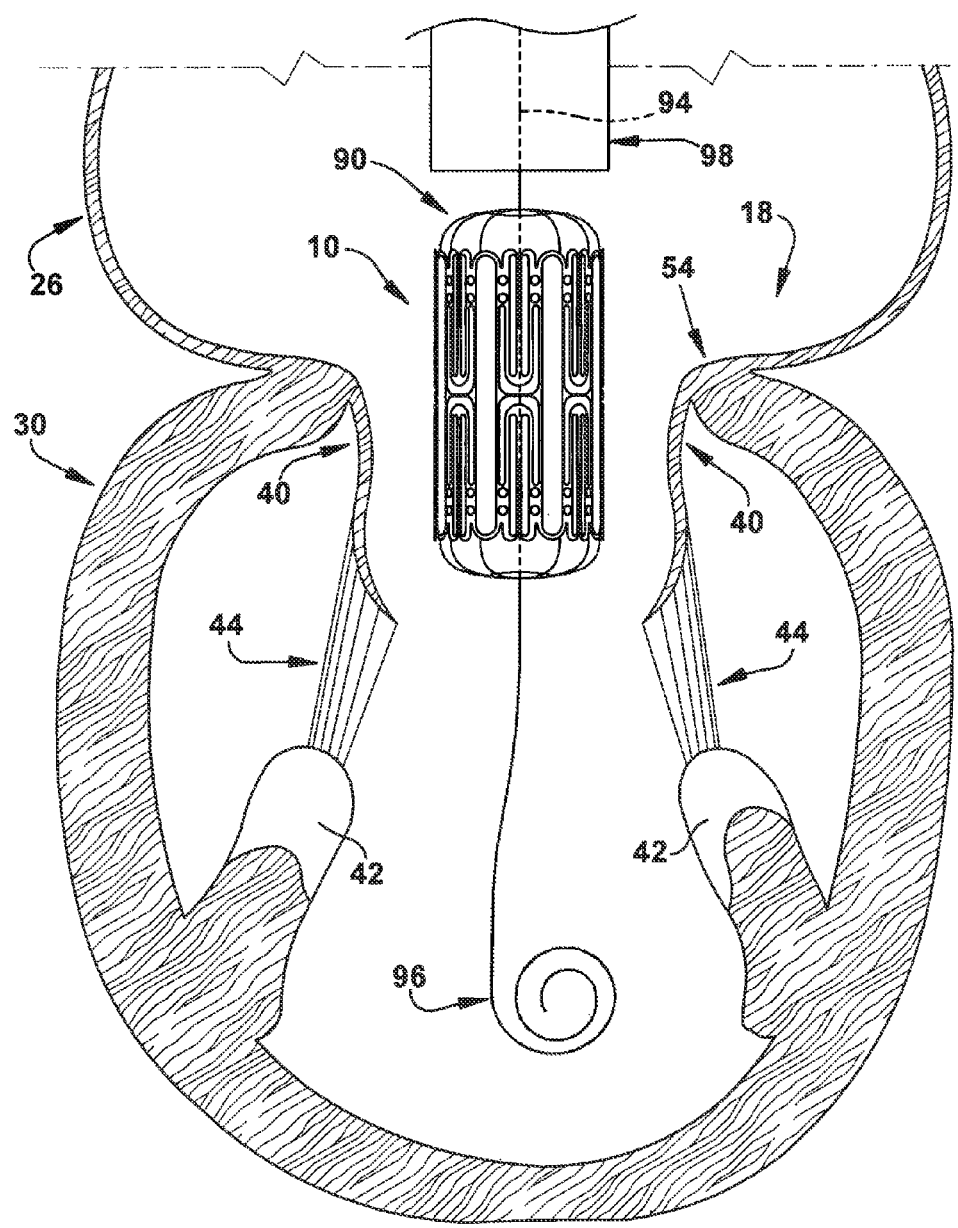
FIG. 23 is a cross-sectional view of a magnified mitral valve showing the apparatus in FIG. 22 being deployed in the mitral valve with an inflatable member.

Upon reaching the distal end 98 of the delivery catheter 92, the apparatus 10 is deployed at Step 88. As shown in FIG. 23, the apparatus 10 is positioned adjacent the mitral annulus 54 and progressively freed from the delivery catheter 92. As the apparatus 10 is progressively freed from the delivery catheter 92, the position of the apparatus in the mitral annulus 54 can be monitored, controlled, and/or quality assured by imaging systems of various kinds For example, X-ray machines, angiography, fluoroscopic machines, ultrasound, CT, MRI, positron emission tomography (PET), and other imaging devices may be used.

Figure 24:
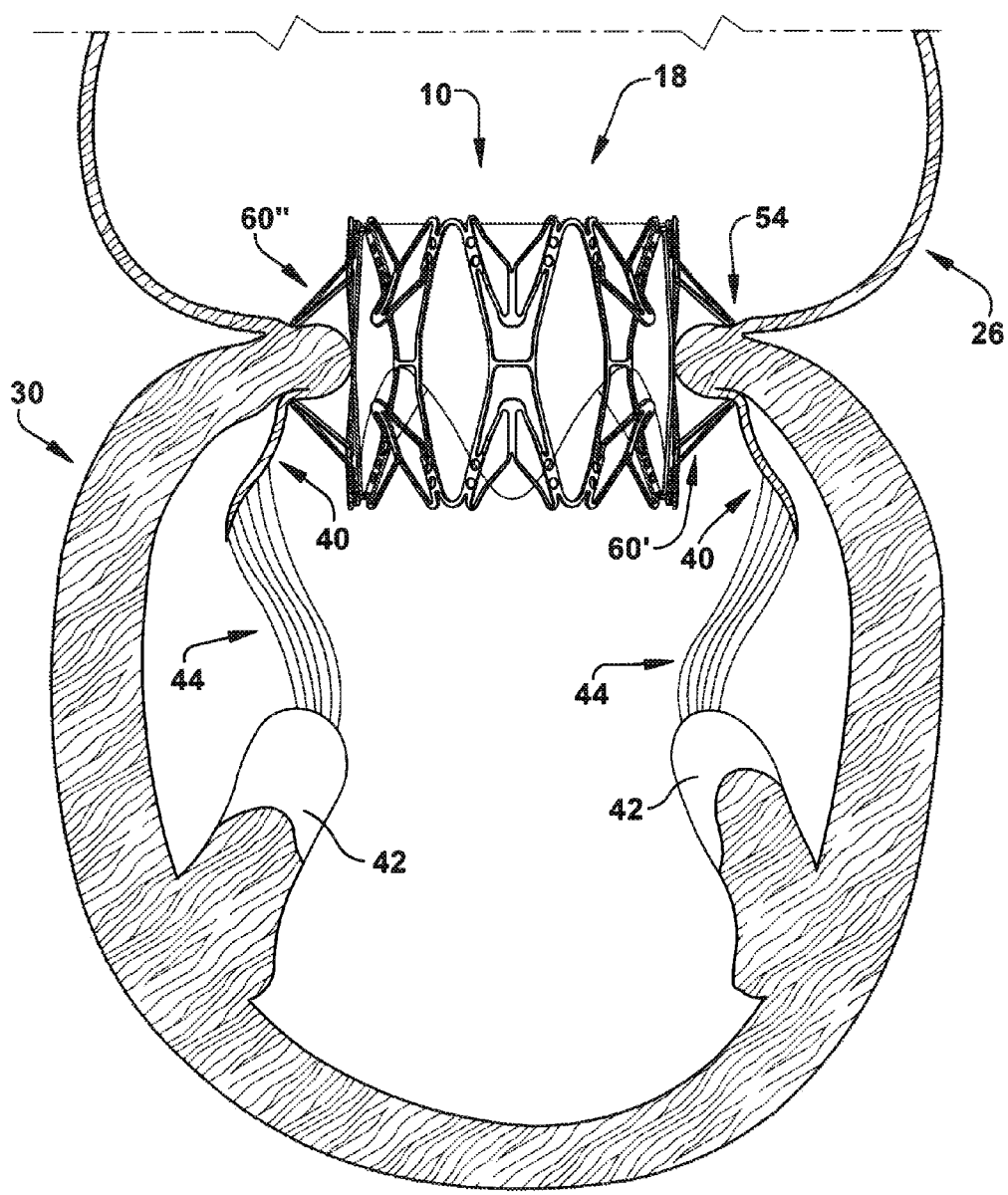
FIG. 24 is a cross-sectional view of the mitral valve showing the apparatus of FIG. 1B securely positioned in place of the mitral valve in FIG. 23.

After positioning the apparatus 10 as shown in FIG. 23, the inflatable member 90 is inflated using a suitable inflation medium, such air or a saline solution. Inflating the inflatable member 90 pushes the main body portion 52 of the expandable support member 12 radially outward into engagement with the mitral annulus 54 and, simultaneously, causes the wing members 60' and 60" to radially expand. As shown in FIG. 24, for example, the first end portion 64 of each of the wing members 60' comprising the first plurality of wing members moves radially outward from the outer circumferential surface 56 into contact with the mitral leaflets 40 and the chordae (not shown); although, it should be appreciated that the wing members may additionally or alternatively move into contact with a portion of the annulus 54. Additionally, the first end portion 64 of each of the wing members 60" comprising the second plurality of wing members moves radially outward into contact with the annulus 54.

With the apparatus 10 in the radially expanded configuration, the first and second plurality of wing members 60' and 60" respectively embrace the inferior and superior aspects of the mitral valve 18 and, consequently, secure the apparatus in place of the diseased mitral valve 18. Additionally, the radially expansive force of the main body portion 52 serves to secure the apparatus 10 in the mitral valve 18. Blood can now flow through the expandable support member 12 and contact the substantially dehydrated bioprosthetic valve 14. As blood contacts the valve 14, the interstices of the valve are re-hydrated and cause the valve to obtain its original (or substantially original) properties and assume normal (or substantially normal) blood flow performance. It should be appreciated that the prosthetic valve 14 may not be re-hydrated with blood where the prosthetic valve comprises a standard (i.e., non-dehydrated) bioprosthetic valve (e.g., made of porcine tissue). With the apparatus 10 fully deployed, the inflatable member 90 is deflated, moved out of the mitral valve annulus 54, and the procedure completed.

Figure 25:
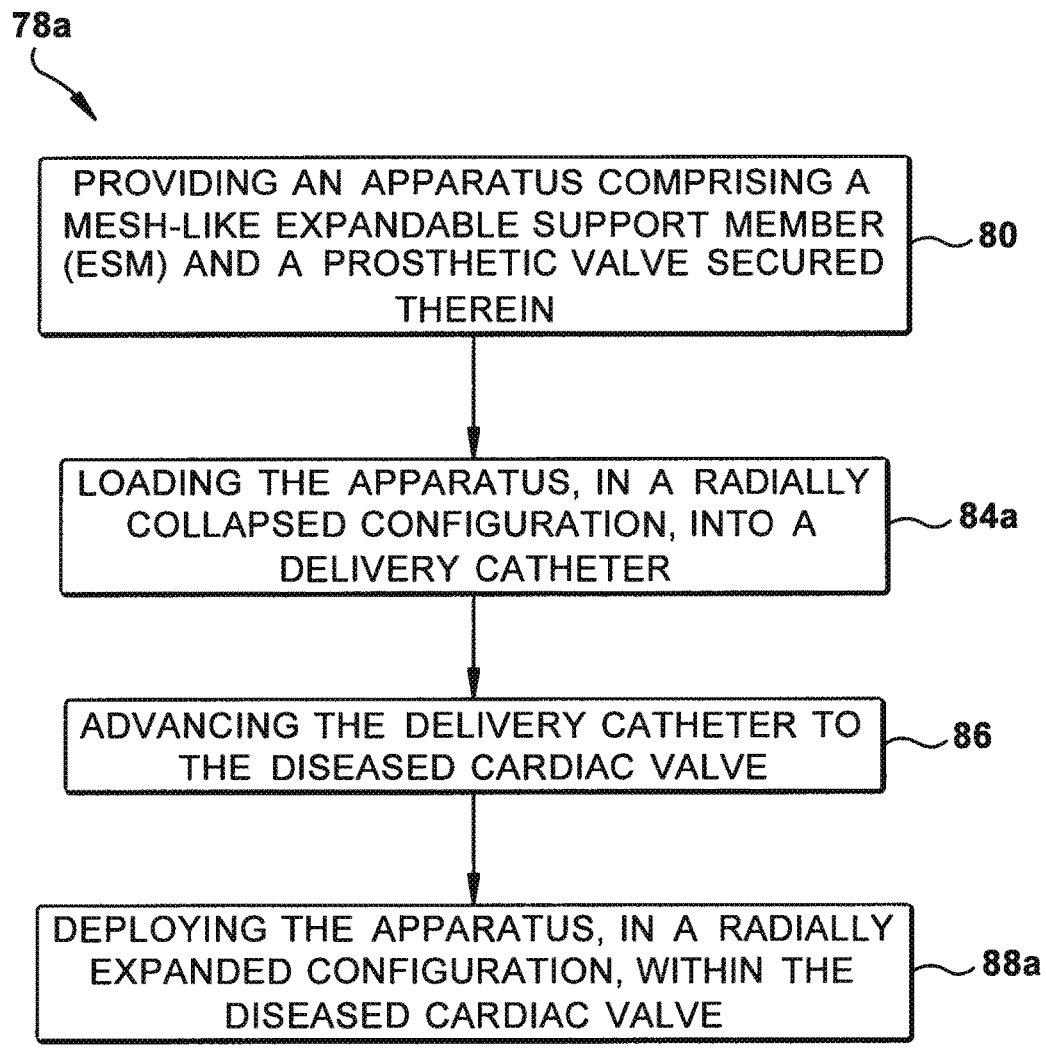
FIG. 25 is a process flow diagram illustrating a method for replacing a diseased cardiac valve according to another aspect of the present invention.

In another aspect of the present invention, a method $78_a$ (FIG. 25) is provided for replacing a diseased cardiac valve 16 (e.g., a diseased mitral valve 18). The steps of the method $78_a$ are identical to the steps of the method 78 shown in FIG. 18, except where as described below. In FIG. 25, steps that are identical to steps in FIG. 18 use the same reference numbers, whereas steps that are similar but not identical carry the suffix "a". Although the method $78_a$ is illustrated below using a percutaneous approach, it will be appreciated that other approaches can be used for replacing the diseased cardiac valve 16. Examples of such alternative approaches can include, but are not limited to, open heart surgery, thoracotomy, left atrial dome insertion, left atrial appendage insertion, transapical insertion, insertion via a pulmonary vein 38, and other minimally invasive techniques known in the art.

One step of the method $78_a$ includes providing an apparatus 10 at Step 80. For example, the apparatus 10 can have a configuration as illustrated in FIGS. 1A-4B and be made of a self-expandable material, such as Nitinol. Prior to placement of the apparatus 10, the dimensions of the diseased mitral valve 18 are determined using known imaging techniques, as described above. After determining the dimensions of the diseased mitral valve 18, an appropriately-sized apparatus 10 having dimensions that correspond to the dimensions of the diseased mitral valve is selected.

To enable delivery and deployment of the apparatus 10 in the diseased mitral valve 18, the apparatus 10 is placed in the radially collapsed configuration and then loaded into a delivery catheter 92 at Step $84_a$. Next, a guidewire 94 is inserted into the vasculature via a femoral vein (not shown) or jugular vein (not shown) and, under image guidance (e.g., fluoroscopy, ultrasound, MRI, CT, angiography, or a combination thereof), respectively steered through the vasculature into the inferior vena cava 36 or superior vena cava 34. The guidewire 94 is then passed across the right atrium 24 so that the distal end 96 of the guidewire pierces the interatrial septum 32 (FIG. 19). The guidewire 94 is extended across the left atrium 26 and then downward through the diseased mitral valve 18 so that the distal end 96 of the guidewire is securely positioned in the left ventricle 30 (FIG. 20).

After the guidewire 94 is appropriately positioned in the heart 22, the delivery catheter 92 is passed over the guidewire at Step 86 (FIG. 21). After the delivery catheter 92 is positioned as shown in FIG. 21, the apparatus 10 is attached to the proximal end (not shown) of the guidewire 94. A positioning wire (not shown) or other similar device useful for advancing the apparatus 10 over the guidewire 94 is then attached to the apparatus. An axial force is then applied to the positioning wire so that the apparatus 10 is passed over the guidewire 94 and positioned at the distal end 98 of the delivery catheter 92 (not shown).

Figure 26:
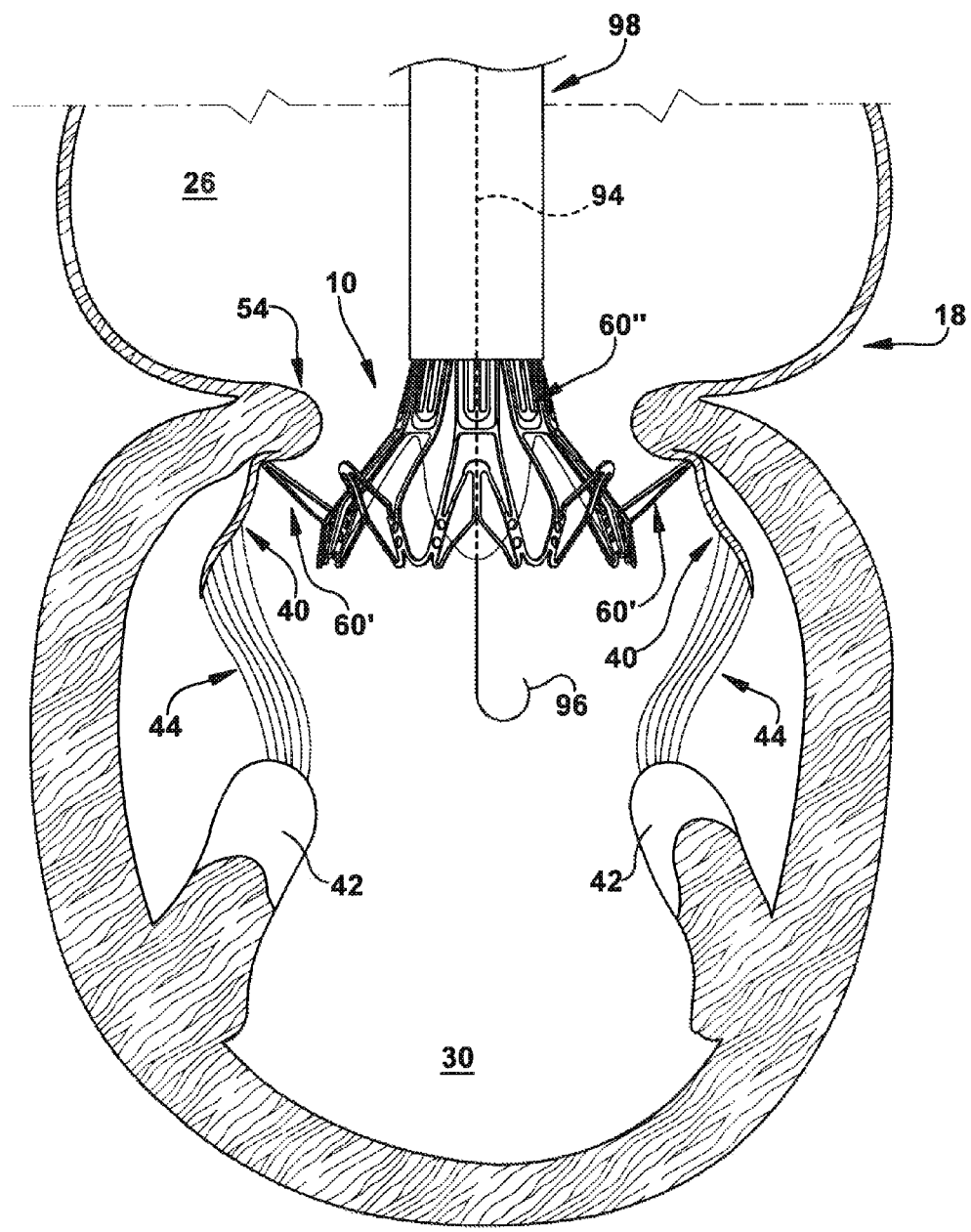
FIG. 26 is a cross-sectional view of the mitral valve showing the apparatus of FIG. 1B self-expanding in place of the mitral valve in FIG. 23.

Upon reaching the distal end 98 of the delivery catheter 92, the apparatus 10 is deployed at Step $88_a$. As shown in FIG. 26, the apparatus 10 is positioned adjacent the mitral annulus 54 and progressively freed from the delivery catheter 92. As the apparatus 10 is progressively freed from the delivery catheter 92, the position of the apparatus in the mitral annulus 54 can be monitored, controlled, and/or quality assured by imaging systems of various kinds. For example, X-ray machines, angiography, fluoroscopic machines, ultrasound, CT, MRI, PET, and other imaging devices may be used.

Figure 27:
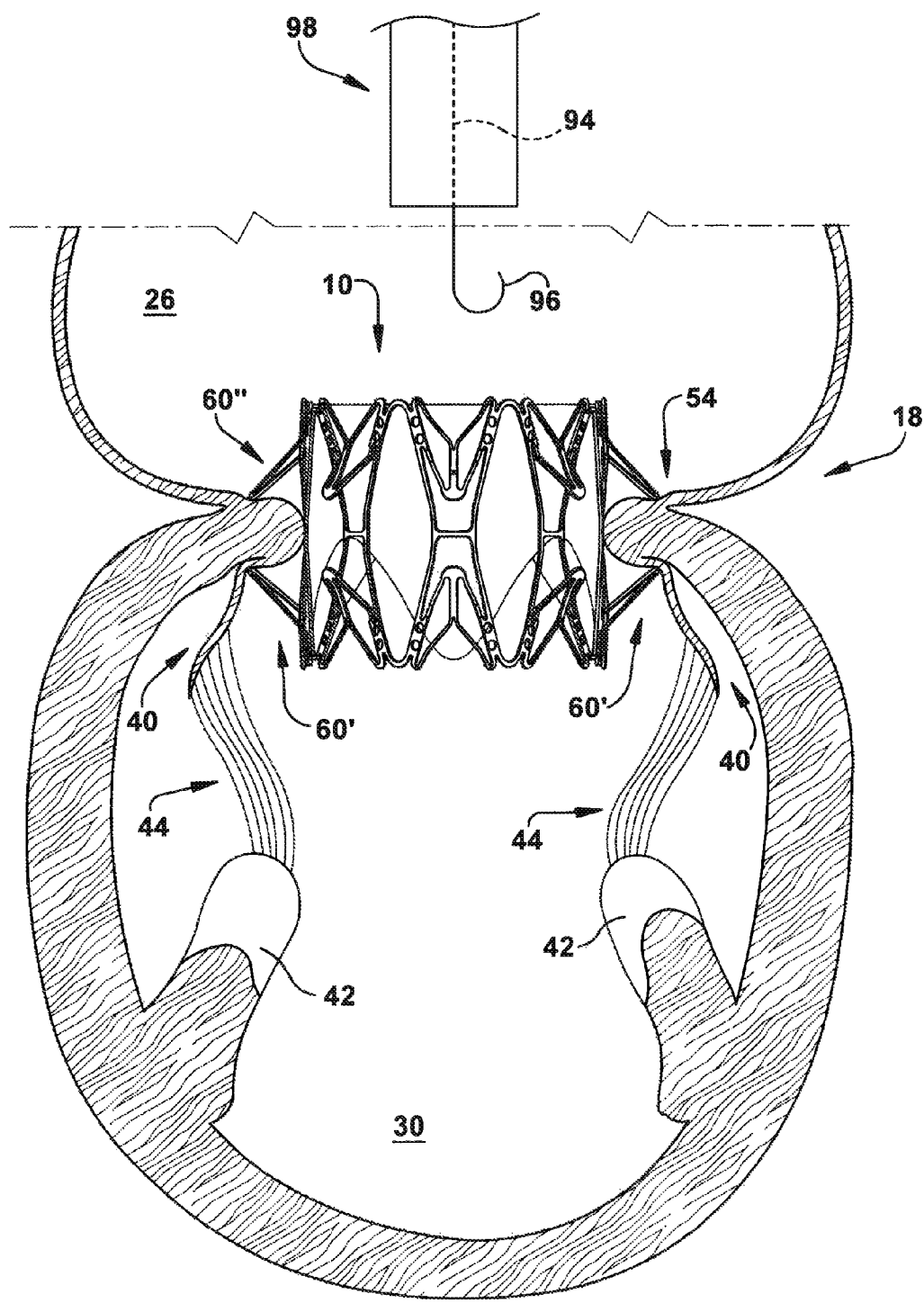
FIG. 27 is a cross-sectional view showing the apparatus in FIG. 26 implanted in the mitral valve.

Progressively withdrawing the delivery catheter 92 allows the second end portion 50 of the expandable support member 12 to expand. As the second end portion 50 expands, the first end portion 64 of each of the wing members 60' comprising the first plurality of wing members moves radially outward from the outer circumferential surface 56 into contact with the mitral leaflets 40 and the chordae (not shown); although, it should be appreciated that the wing members may additionally or alternatively move into contact with a portion of the annulus 54. Continually withdrawing the delivery catheter 92 then allows the main body portion 52 of the expandable support member 12 to engage the mitral annulus 54. As the delivery catheter 92 is finally removed from over the apparatus 10, the first end portion 64 of each of the wing members 60" comprising the second plurality of wing members moves radially outward into contact with the annulus 54 (FIG. 27).

With the apparatus 10 in the radially expanded configuration, the first and second plurality of wing members 60' and 60" respectively embrace the inferior and superior aspects of the mitral valve 18 and, consequently, secure the apparatus in place of the diseased mitral valve 18. Additionally, the radially expansive force of the main body portion 52 serves to secure the apparatus 10 in the mitral valve 18. Blood can now flow through the expandable support member 12 and contact the substantially dehydrated bioprosthetic valve 14. As blood contacts the valve 14, the interstices of the valve are re-hydrated and cause the valve to obtain its original (or substantially original) properties and assume normal (or substantially normal) blood flow performance. It should be appreciated that the prosthetic valve 14 may not be re-hydrated with blood where the prosthetic valve comprises a standard (i.e., non-dehydrated) bioprosthetic valve (e.g., made of porcine tissue).

FIGS. 28-32 illustrate an alternative method $78_a$ for replacing a diseased cardiac valve 16 (e.g., a diseased mitral valve 18). The method $78_a$ is identical to method (FIG. 25) described above, except that the delivery catheter 92' used to deliver the apparatus 10 has a different configuration than the delivery catheter 92 illustrated in FIGS. 26-27 and described above.

Figure 28:
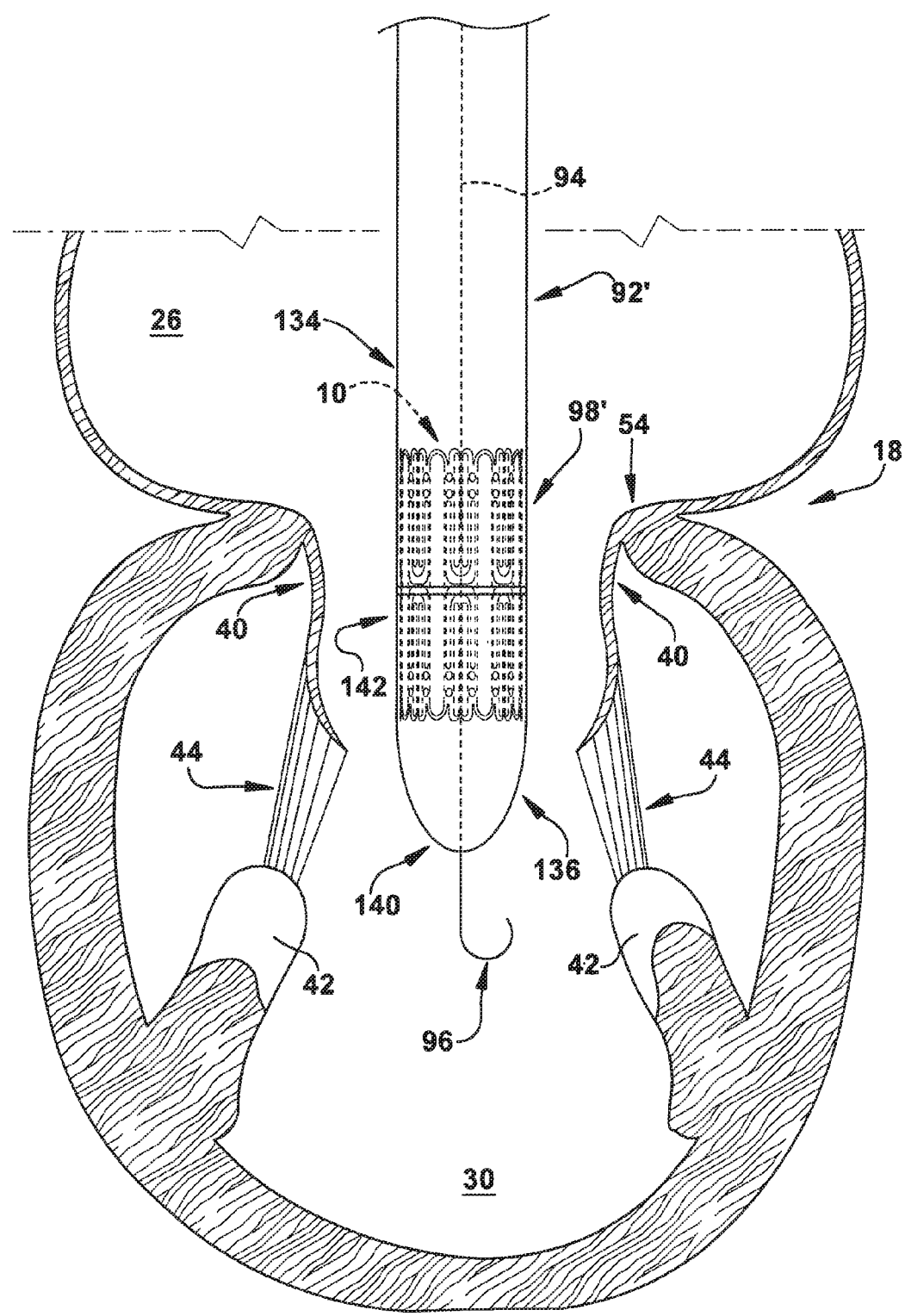
FIG. 28 is a cross-sectional view showing an alternative configuration of the delivery catheter in FIG. 26.
Figure 29:
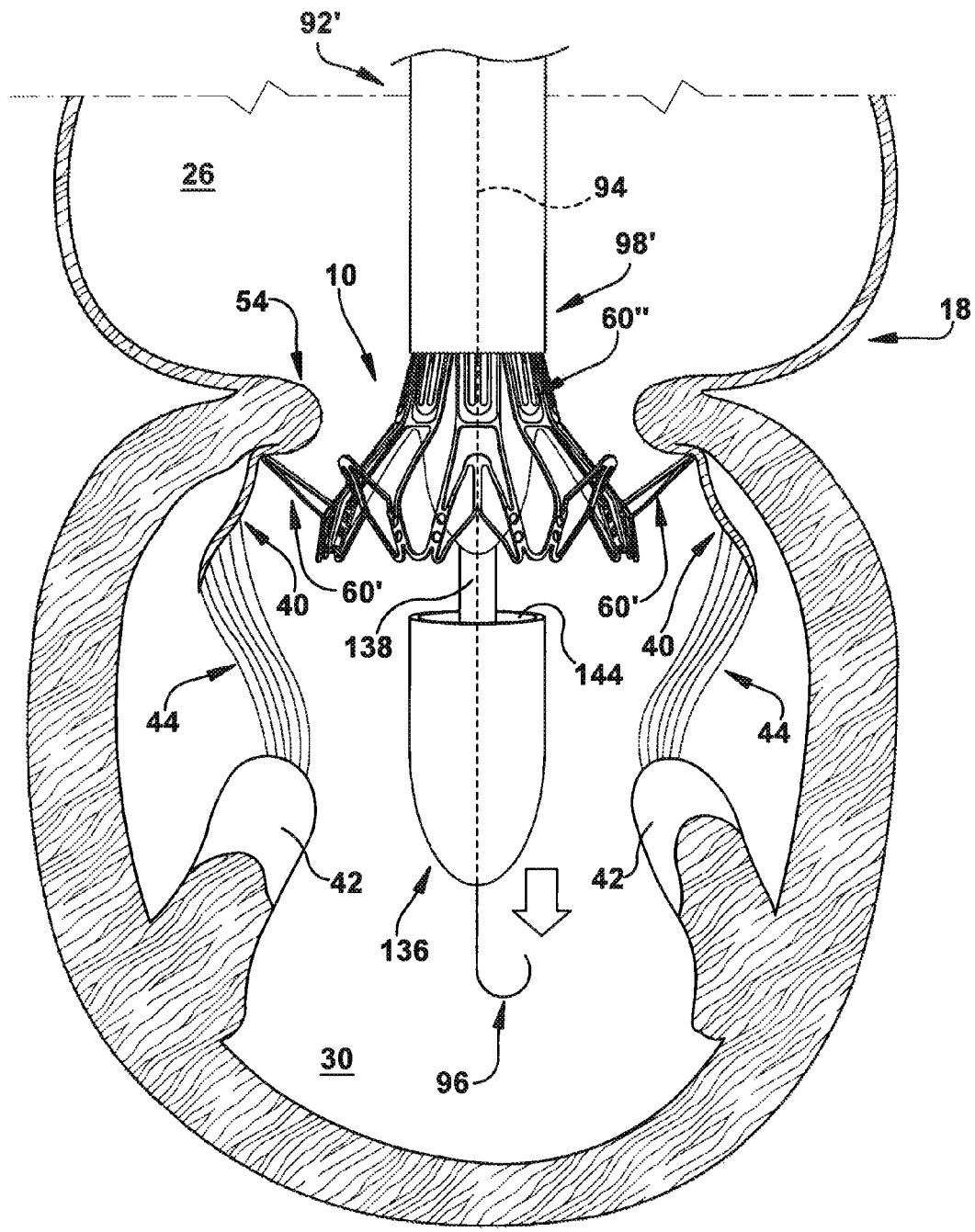
FIG. 29 is a cross-sectional view showing the delivery catheter in FIG. 28 deploying the apparatus in FIG. 1B.

As shown in FIGS. 28-32, the delivery catheter 92' comprises a main body portion 134 that is similar or identical to the delivery catheter 92 described above. For example, the main body portion 134 has an elongated, tube-like configuration with a proximal end (not shown) and a distal end 98'. The delivery catheter 92' also includes a conical distal tip 136 that is operably connected to a rod-like positioning member 138 (FIG. 29). As described in more detail below, the positioning member 138 extends longitudinally through the delivery catheter 92' and can be controlled or manipulated (e.g., using tactile force) at its proximal end (not shown) to engage or disengage the distal tip 136 with or from the distal end 98' of the delivery catheter.

The distal tip 136 includes oppositely disposed first and second ends 140 and 142 and a cavity 144 (FIG. 29) extending between the first and second ends. The first end 140 includes a central aperture (not shown in detail) for receiving the distal end 96 of the guidewire 94. The second end 142 is capable of mating with the distal end 98' of the delivery catheter 92'. The second end 142 of the distal tip 136 has a diameter sufficient to permit at least a portion of the apparatus 10 to be disposed in a portion of the cavity 144 when the apparatus is in the radially collapsed configuration (i.e., during deployment). The distal tip 136 can have a rigid or semi-rigid configuration and be made of the same or similar material as the main body portion 134 of the delivery catheter 92'.

To replace a diseased cardiac valve 16, such as the mitral valve 18, an apparatus 10 that is similar or identical to the one illustrated in FIGS. 1A-4B and made of a self-expandable material (e.g., Nitinol) is provided at Step 80. The apparatus 10 is then placed in the radially collapsed configuration and then loaded into the delivery catheter 92' at Step $84_a$. To load the apparatus 10 into the delivery catheter 92', the apparatus is placed at the proximal end of the delivery catheter and then advanced over the positioning member 138 to the distal end 98'. Prior to advancing the apparatus 10 to the distal end 98', however, the second end 142 of the distal tip 136 is mated with the distal end so that the distal end of the delivery catheter 92' has a bullet-shaped configuration (FIG. 28).

Next, a guidewire 94 is inserted into the vasculature via a femoral vein (not shown) or jugular vein (not shown) and, under image guidance (e.g., fluoroscopy, ultrasound, MRI, CT, angiography, or a combination thereof), respectively steered through the vasculature into the inferior vena cava 36 or superior vena cava 34. The guidewire 94 is then passed across the right atrium 24 so that the distal end 96 of the guidewire pierces the interatrial septum 32 (as described above). The guidewire 94 is extended across the left atrium 26 and then downward through the diseased mitral valve 18 so that the distal end 96 of the guidewire is securely positioned in the left ventricle 30.

After the guidewire 94 is appropriately positioned in the heart 22, the delivery catheter 92' is passed over the guidewire 94 at Step 86 until the delivery catheter is positioned as shown in FIG. 28. It will be appreciated that that the apparatus 10 may alternatively be delivered to the distal end 98' of the delivery catheter 92' by sliding the delivery catheter over the guidewire 94, attaching the apparatus to the proximal end of the guidewire, and then advancing the apparatus to the distal end of the delivery catheter.

Next, an axial force is applied to the proximal end of the positioning member 138 (e.g., using tactile means). Application of the axial force causes the distal tip 136 to disengage from the distal end 98' of the delivery catheter 92' and move downward into the left atrium 26 (indicated by arrow in FIG. 29). Downward movement of the distal tip 136 allows the second end portion 50 of the expandable support member 12 to expand. As the second end portion 50 expands, the first end portion 64 of each of the wing members 60' comprising the first plurality of wing members moves radially outward from the outer circumferential surface 56 into contact with the mitral leaflets 40 and the chordae (not shown); although, it should be appreciated that the wing members may additionally or alternatively move into contact with a portion of the annulus 54.

At Step 88$_a$, the delivery catheter 92' is continually withdrawn to allow the apparatus 10 to expand into the annulus 54. As the apparatus 10 is progressively freed from the delivery catheter 92', the position of the apparatus in the mitral annulus 54 can be monitored, controlled, and/or quality assured by imaging systems of various kinds. For example, X-ray machines, angiography, fluoroscopic machines, ultrasound, CT, MRI, PET, and other imaging devices may be used. Progressively withdrawing the delivery catheter 92' allows the second end portion 50 of the expandable support member 12 to expand.

Figure 30:
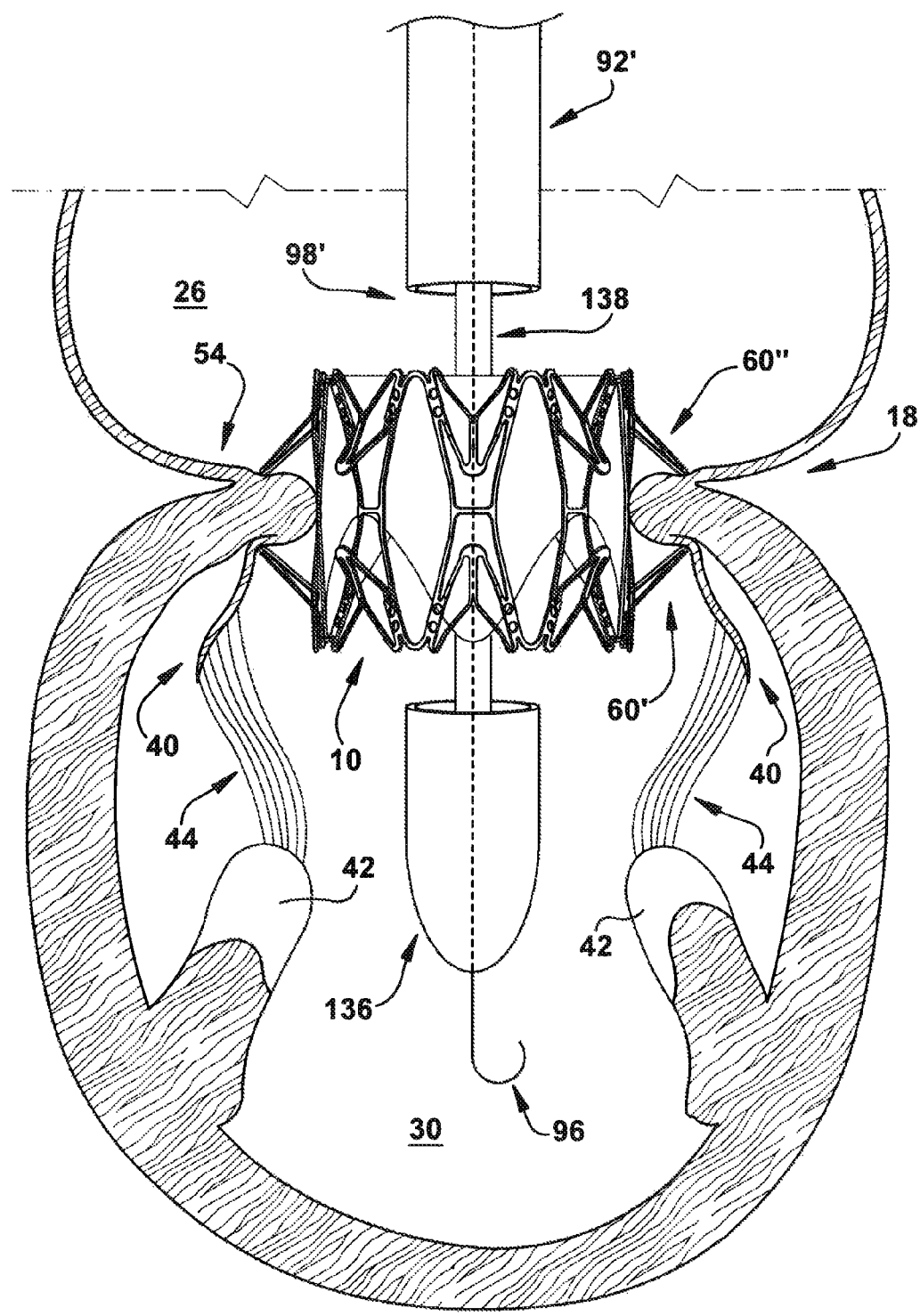
FIG. 30 is a cross-sectional view showing the apparatus in FIG. 29 being deployed in the mitral valve.

As the second end portion 50 expands, the first end portion 64 of each of the wing members 60' comprising the first plurality of wing members moves radially outward from the outer circumferential surface 56 into contact with the mitral leaflets 40 and the chordae (not shown); although, it should be appreciated that the wing members may additionally or alternatively move into contact with a portion of the annulus 54. Continually withdrawing the delivery catheter 92' then allows the main body portion 52 of the expandable support member 12 to engage the mitral annulus 54. As the delivery catheter 92' is finally removed from over the apparatus 10, the first end portion 64 of each of the wing members 60" comprising the second plurality of wing members moves radially outward into contact with the annulus 54 (FIG. 30).

With the apparatus 10 in the radially expanded configuration, the first and second plurality of wing members 60' and 60" respectively embrace the inferior and superior aspects of the mitral valve 18 and, consequently, secure the apparatus in place of the diseased mitral valve 18. Additionally, the radially expansive force of the main body portion 52 serves to secure the apparatus 10 in the mitral valve 18. Blood can now flow through the expandable support member 12 and contact the substantially dehydrated bioprosthetic valve 14. As blood contacts the valve 14, the interstices of the valve are re-hydrated and cause the valve to obtain its original (or substantially original) properties and assume normal (or substantially normal) blood flow performance. It should be appreciated that the prosthetic valve 14 may not be re-hydrated with blood where the prosthetic valve comprises a standard (i.e., non-dehydrated) bioprosthetic valve (e.g., made of porcine tissue).

Figure 31:
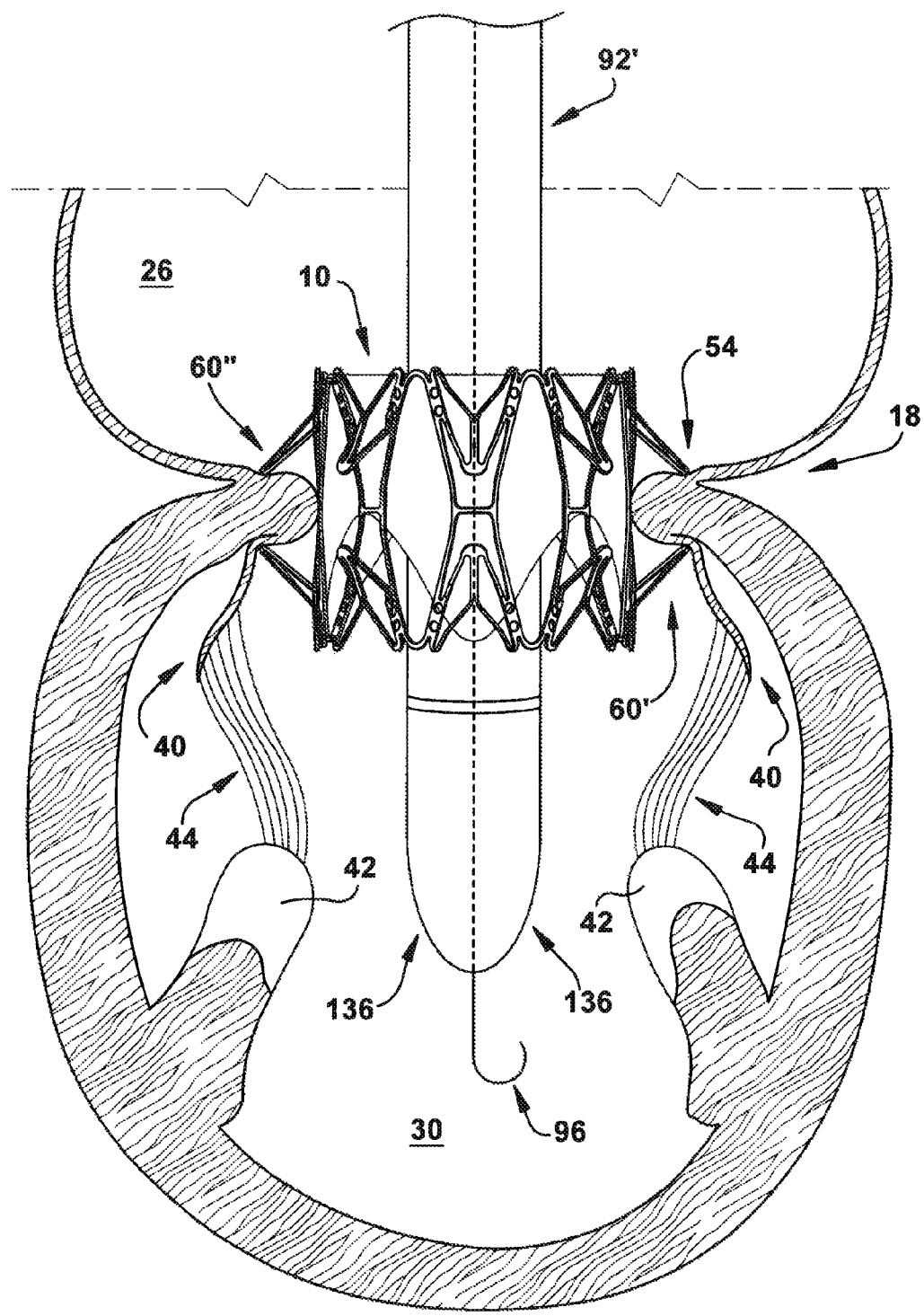
FIG. 31 is a cross-sectional view showing the apparatus in FIG. 30 deployed in the mitral valve and the delivery catheter in FIG. 30 placed in a non-deployed configuration.
Figure 32:
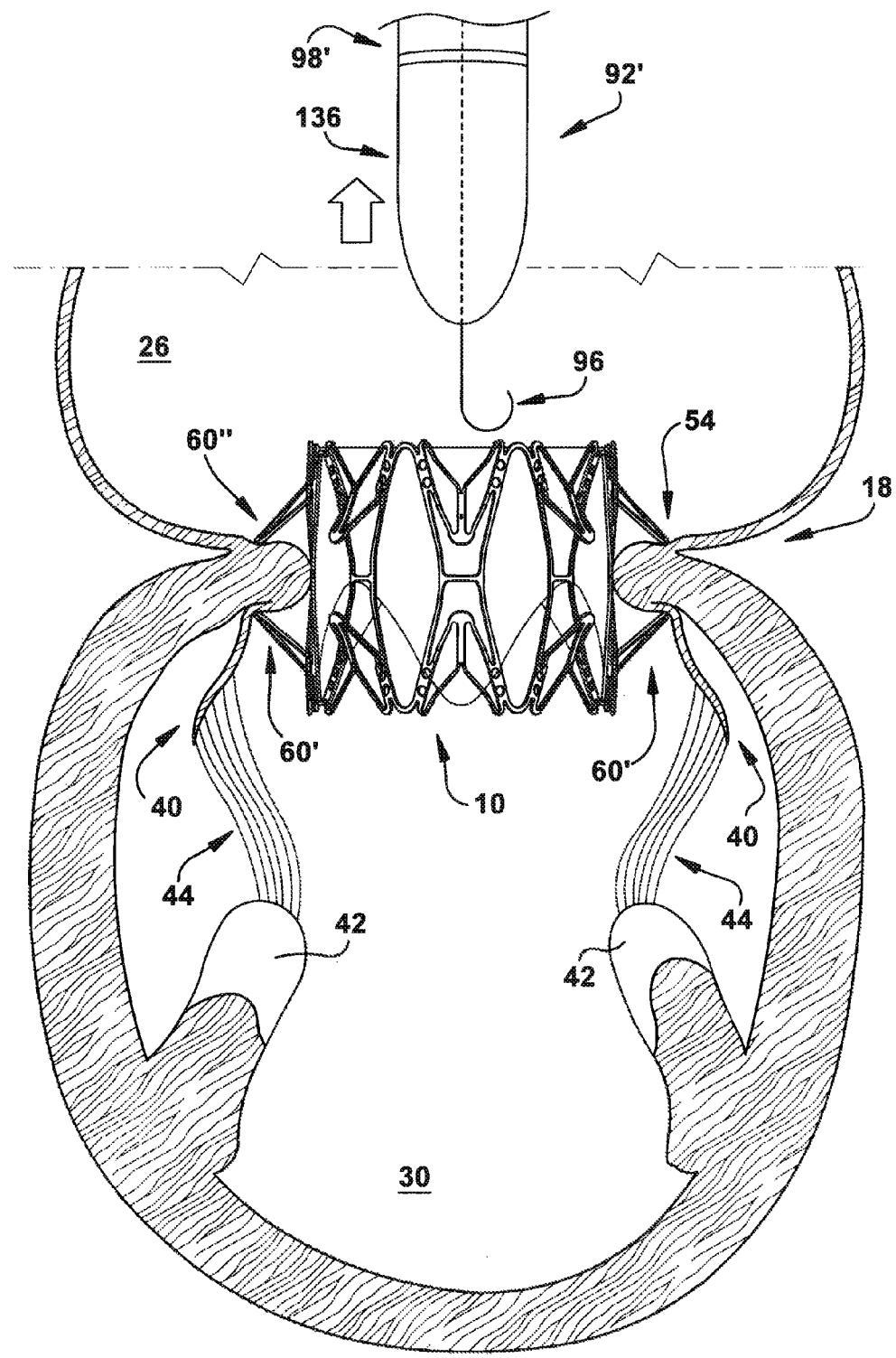
FIG. 32 is a cross-sectional view showing the catheter in FIG. 31 being removed from the subject.
Figure 33:
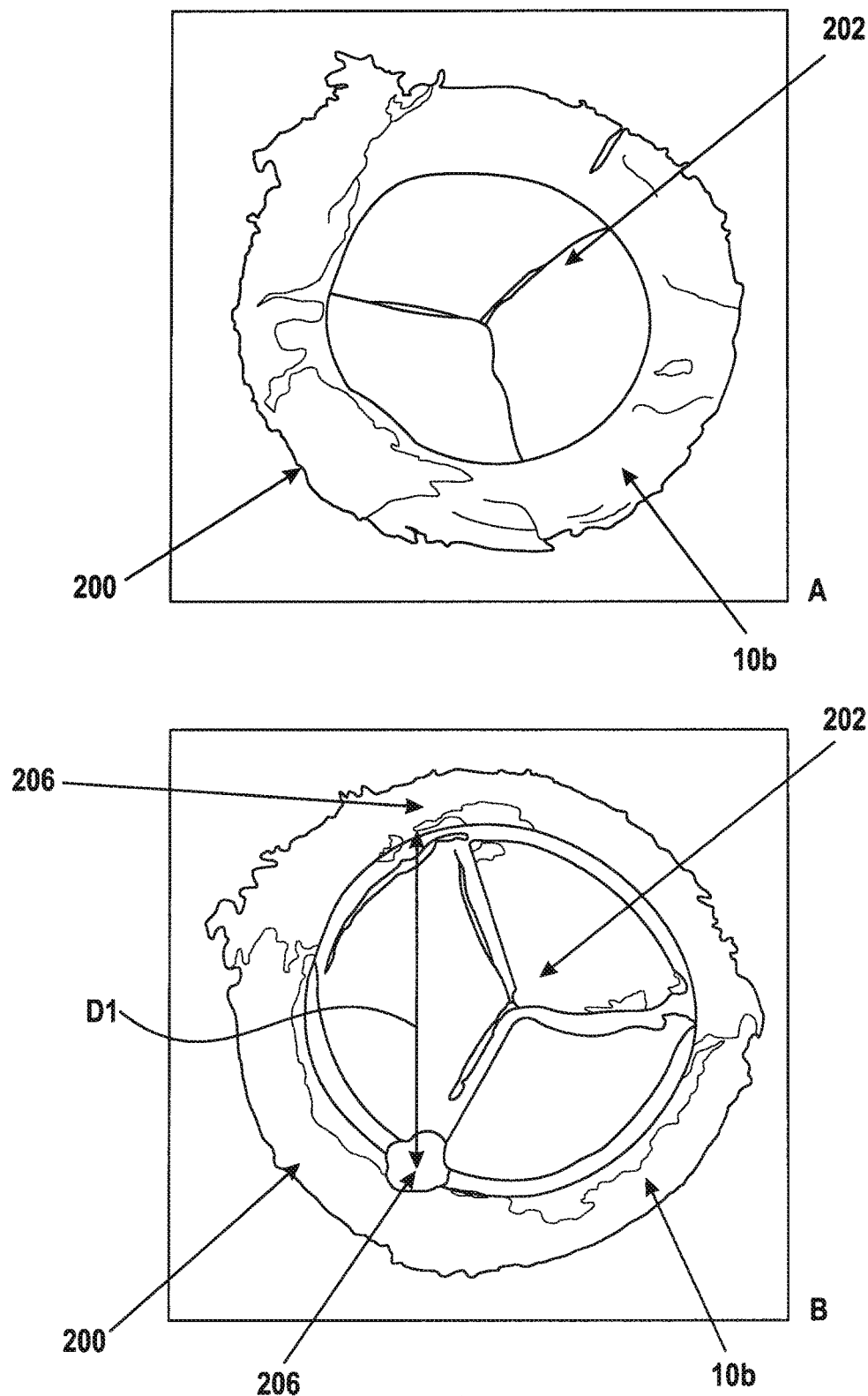
FIGS. 33A-B are perspective views showing an alternative configuration of the apparatus in FIG. 1B.
Figure 34:
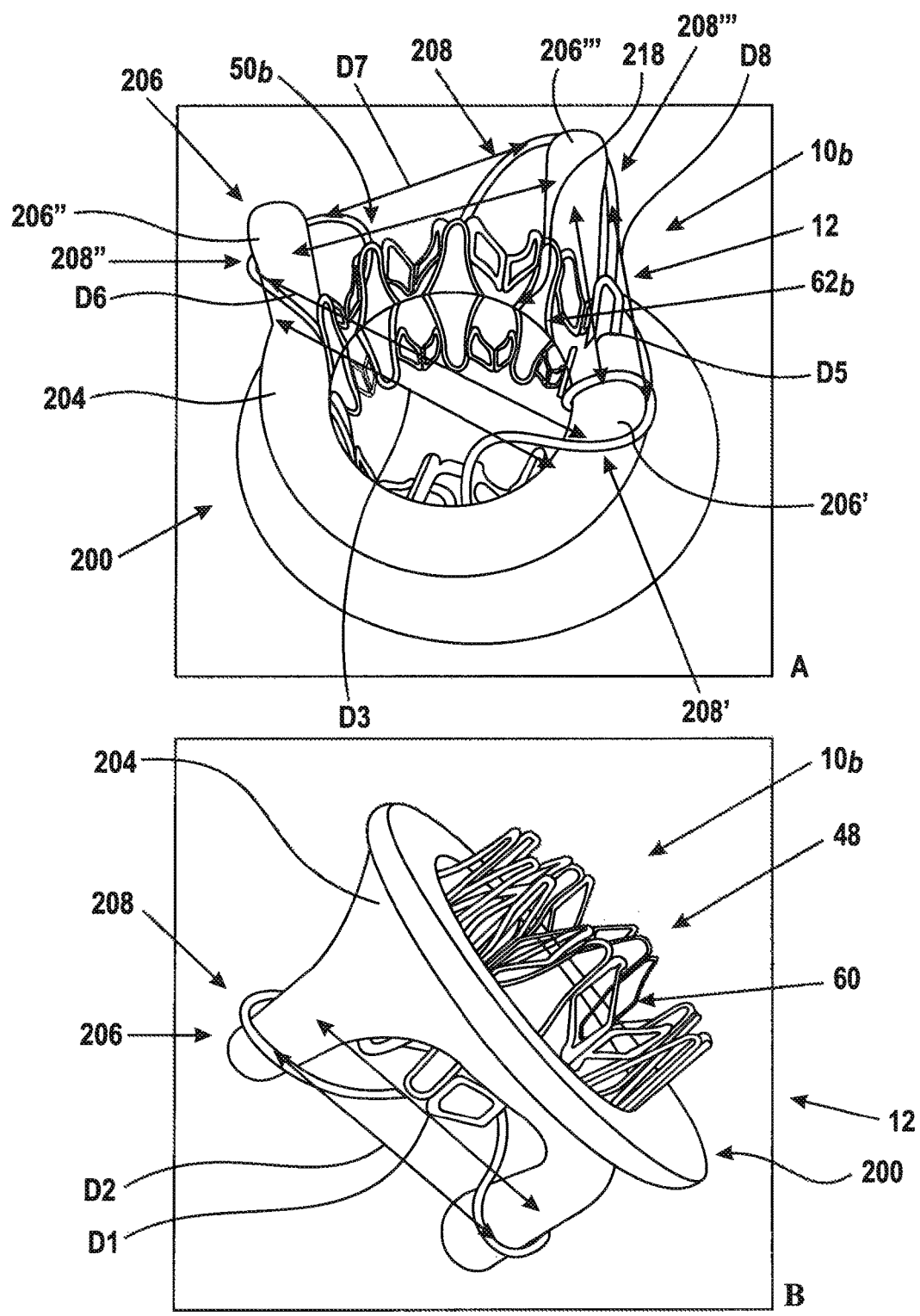
FIGS. 34A-B are perspective views showing the apparatus in FIGS. 33A-B without a bioprosthetic valve (for clarity)
Figure 36:
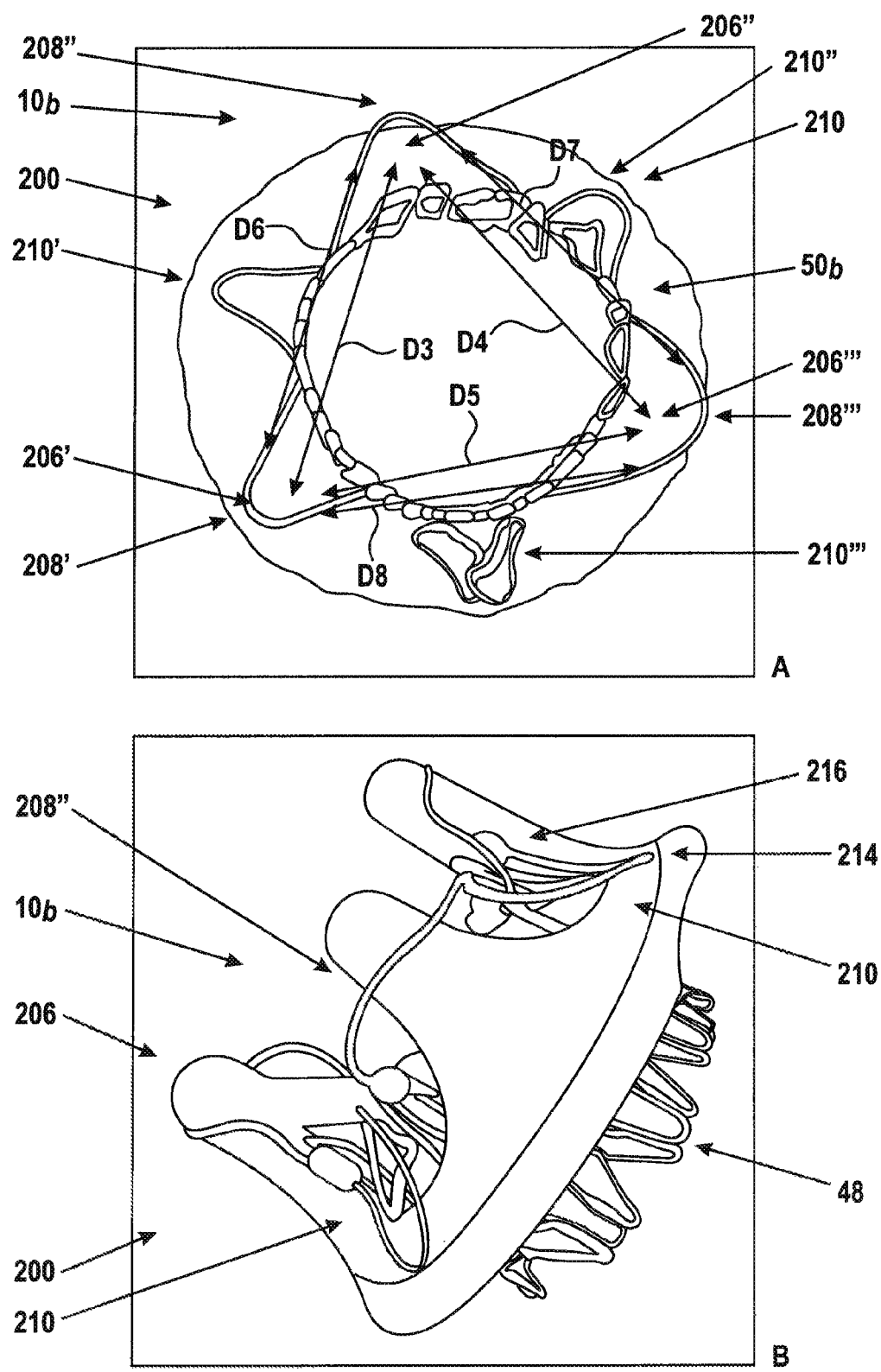
FIGS. 36A-B are perspective views showing an alternative configuration of the apparatus in FIGS. 34A-B.
Figure 37:
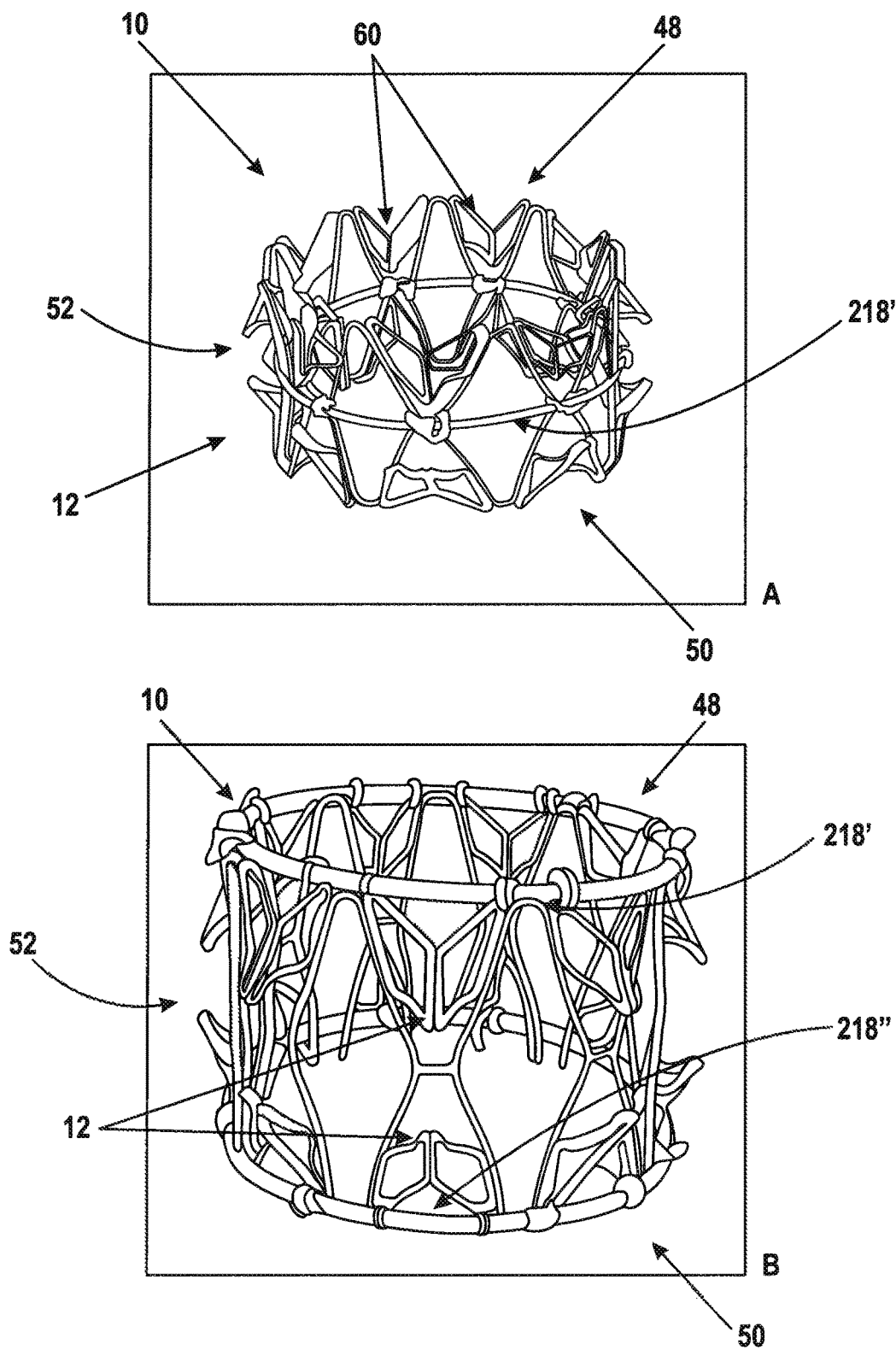
FIGS. 37A-B are a perspective view of the apparatus in FIGS. 34A-B optionally including an expandable ring disposed about a main body portion of the apparatus (FIG. 37A) and first and second expandable rings disposed about the first and second end portions, respectively, of the apparatus (FIG. 37B)

After the apparatus 10 has been deployed in the mitral valve 18, an axial force is applied to the proximal end of the positioning member 138 so that the second end 142 of the distal tip 136 is drawn toward the main body portion 134 and engages the distal end 98 of the delivery catheter 92' (FIG. 31). As shown in FIG. 32, the delivery catheter 92' and the guidewire 94 are then removed from the left atrium 26 and the procedure completed.

Another aspect of the present invention is illustrated in FIGS. 33A-38B. The apparatus 10$_b$ is identically constructed as the apparatus 10 shown in FIGS. 1A-B, except where as described below. In FIGS. 33A-38B, structures that are identical as structures in FIGS. 1A-B use the same reference numbers, whereas structures that are similar but not identical carry the suffix "b".

Implantation of bioprosthetic cardiac valves to treat hemodynamically significant valvular disease has become an increasingly common procedure. Replacement of diseased or dysfunctional bioprosthetic valves reduces the morbidity and mortality associated with valvular disease or dysfunction, but comes at the expense of risking complications unique to the implanted or indwelling bioprosthetic device. These complications include valve failure due to calcification or stenosis/fibrosis, valvular endocarditis, valvular thrombosis, thromboembolism, mechanical hemolytic anemia, and anticoagulant-related hemorrhage. When bioprosthetic valves fail, their removal and replacement entails a highly complicated and invasive procedure. As described in more detail below, the apparatus 10$_b$ of the present invention can advantageously be used to replace a previously-implanted or indwelling bioprosthetic valve 200 (FIG. 40) that has failed without the need for removal of the failed bioprosthetic valve. Consequently, the present invention assists in helping subjects with failed bioprosthetic valves avoid the numerous potential complications and hardships often associated with replacing such failed devices.

As shown in FIGS. 33A-34B, an apparatus 10$_b$ for replacing an indwelling or previously-implanted bioprosthetic valve 200 can comprise an expandable support member 12 (FIGS. 34A-B) and a bioprosthetic valve 202 (FIGS. 33A-B) secured therein. Bioprosthetic valves are well known in the art and can generally comprise a frame 204 having at least two commissural portions 206 (e.g., posts) spaced apart by a first distance D1 (FIG. 33B). Bioprosthetic valves also generally include a tissue portion comprising a plurality of leaflets, all or a portion of which can be made of a synthetic or biological material. For clarity, the bioprosthetic valve 200 shown in FIGS. 34A-37B does not include a tissue portion.

As mentioned above, the apparatus 10$_b$ can include an expandable support member 12, commonly referred to as a stent, and a bioprosthetic valve 202 secured therein. The expandable support member 12 can have a saddle-shaped, 3-D configuration and include a first end portion 48, a second end portion 50$_b$, and a main body portion 52$_b$ extending between the first and second end portions. The main body portion 52$_b$ can include an outer circumferential surface 56$_b$ and a circumferential axis CA extending about the outer circumferential surface. As described above, all or only a portion of the expandable support member 12 may be made from a medical grade metal or plastic (e.g., shape memory materials). For example, all or only a portion of the expandable support member 12 may be made of a Co—Cr alloy, such as Co-20Cr-15W-10Ni. The expandable support member 12 may be self-expandable or mechanically expandable (e.g., using a balloon), depending upon the material used to construct the expandable support member.

As shown in FIGS. 34A-B, the second end portion $50_b$ of the expandable support member 12 can include at least two flexible arch members 208 spaced apart by a second distance D2. The second distance D2 can be about equal to the first distance D1 so that the at least two arch members 208 can securely engage the commissural portions 206 (e.g., posts) of the indwelling bioprosthetic valve 200. The flexible arch members 208 can move from a collapsed configuration to an expanded configuration when the apparatus $10_b$ is in the radially collapsed and expanded configurations, respectively. In the collapsed configuration (not shown), the flexible arch members 208 can be co-planar with the outer circumferential surface $56_b$ (and extend radial to the circumferential axis CA) so that the apparatus $10_b$ can be readily moved into the indwelling bioprosthetic valve 200 for deployment. In the expanded configuration (FIGS. 34A-B), the flexible arch members 208 can bend, flex, or protrude outward so that they are offset from and/or non-coplanar with (e.g., substantially radial to) the outer circumferential surface $56_b$. For example, the flexible arch members 208 can be offset from the outer circumferential surface $56_b$ by about 1° to about 90° or more. As described in more detail below, expansion or flexion of the arch members 208 can anchor each of the arch members to a respective commissural portion 206 (e.g., post) of the indwelling bioprosthetic valve 200 to prevent or mitigate migration of the apparatus $10_b$ once implanted.

The flexible arch members 208 can have any configuration (e.g., shape and size) to facilitate engagement and anchoring of the arch members with the commissural portions 206 of the indwelling bioprosthetic valve 200. As shown in FIGS. 34A-B, for example, the arch members 208 can have a U-shaped configuration. It will be appreciated, however, that the flexible arch members 208 can have the same or different configuration. The arch members 208 can be securely attached to the second end portion $50_b$ of expandable support member 12 at at least one attachment point by any suitable means known in the art, such as soldering, an adhesive, etc. For example, each of the arch members 208 can be separately attached to the second end portion $50_b$ at alternating expandable regions $62_b$ of the expandable support member 12. Alternatively, the flexible arch members 208 can be integrally formed with the second end portion $50_b$ of the expandable support member 12. For example, the flexible arch members 208 can be a fluid extension of the material used to form the expandable support member 12. It will be appreciated that the arch members 208 can be attached to any section or portion of the second end portion $50_b$ of the expandable support member 12, and that the flexible arch members can be made of the same or different material (or materials) from which the expandable support member is made.

One example of an apparatus $10_b$ having first, second, and third flexible arch members 208', 208", and 208'" is shown in FIGS. 34A-35B. The apparatus $10_b$ can be used to replace an indwelling bioprosthetic valve 200 having first, second, and third commissural portions 206', 206", and 206'" (e.g., posts) spaced apart by third, fourth, and fifth distances D3, D4 and D5. Each of the first, second, and third flexible arch members 208', 208", and 208'" can have a U-shaped configuration and be connected to alternating expandable regions $62_b$ at the second end portion $50_b$ of the expandable support member 12. Each of the first, second, and third arch members 208', 208", and 208'" can be made of a resiliently bendable material, such as a shape memory material. The first, second, and third arch members 208', 208", and 208'" can be spaced apart by sixth, seventh, and eighth distances D6, D7, and D8 that are about equal to the third, fourth, an fifth distances D3, D4, and D5 (respectively).

It will be appreciated that the apparatus $10_b$ can additionally or optionally include at least one secondary flexible arch member 210 for contacting a non-commissural portion 212 (e.g., a frame or annulus portion) of the indwelling bioprosthetic valve 200. The secondary flexible arch member 210 can have any configuration (e.g., shape and size) to facilitate anchoring of the apparatus $10_b$ in the indwelling bioprosthetic valve 200 and thereby prevent or mitigate migration of the apparatus once implanted. As shown in FIGS. 36A-B, for example, at least one flexible secondary arch member 210 can have a U-shaped configuration and be in the form of a wire comprising a resiliently bendable material (e.g., a shape memory material). The at least one flexible secondary arch member 210 can be made of the same or different material (or materials) as the expandable support member 12.

The at least one flexible secondary arch member 210 can have oppositely disposed first and second end portions 214 and 216. When the apparatus $10_b$ is in the radially collapsed configuration (not shown), the first and second end portions 214 and 216 can be substantially flush with the outer circumferential surface $56_b$ of the expandable support member 12. When the apparatus $10_b$ is in the radially expanded configuration, the first end portion 214 of the flexible secondary arch member 210 can protrude, extend, or be offset from (e.g., substantially radial to) the outer circumferential surface $56_b$ (e.g., by about 1° to about 90° or more). As shown in FIGS. 36A-B, for example, the first end portion 214 of the at least one flexible secondary arch member 210 can engage a non-commissural portion 212 (e.g., the frame or annulus) of the indwelling bioprosthetic valve 200 when the apparatus $10_b$ is in the radially expanded configuration.

Depending upon the desired configuration of the apparatus $10_b$, the at least one secondary flexible arch member 210 can have a length (defined by the distance between the first and second end portions 214 and 216) about equal to the distance between the second end portion $50_b$ of the expandable support member 12 and the circumferential axis CA. One skilled in the art will appreciate that the length of the at least one secondary flexible arch member 210 can be greater or less, however, depending upon the desired configuration of the apparatus $10_b$.

The second end portion 216 of the at least one secondary flexible arch member 210 can be integrally formed with the second end portion $50_b$ of the expandable support member 12. For example, the at least one secondary flexible arch member 210 can be a fluid extension of the material used to form the expandable support member 12. Alternatively, the second end portion 216 of the at least one secondary flexible arch member 210 can be attached to a desired point (or points) at the second end portion $50_b$ of the expandable support member 12 by any suitable means known in the art, such as soldering, an adhesive, etc. As shown in FIGS. 36A-B, the at least one secondary flexible arch member 210 can be located between the flexible arch members 208 and securely affixed to the second end portion $50_b$ at first and second points on different expandable regions $62_b$ of the expandable support member 12.

In one example of the present invention, the apparatus $10_b$ shown in FIGS. 36A-B can be used to replace an indwelling bioprosthetic valve 200 having first, second, and third commissural portions 206', 206", and 206'" (e.g., posts) spaced apart by third, fourth, and fifth distances D3, D4 and D5. As described above, each of the first, second, and third arch flexible members 208', 208", and 208'" of the apparatus 10$_b$ can have a U-shaped configuration and be connected to alternating expandable regions 62$_b$ at the second end portion 50$_b$ of the expandable support member 12. Additionally, the apparatus 10$_b$ can include first, second, and third secondary flexible arch members 210', 210", and 210'" located at the second end portion 50$_b$ of the expandable support member 12 in between the first, second, and third flexible arch members 208', 208", and 208'".

The main body portion 52$_b$ of the apparatus 10$_b$ can include a plurality of wing members 60 spaced apart from one another by the expandable region 62$_b$. As described above, each of the wing members 60 can have an arch-like shape and include a first end portion 64, a second end portion 66, and a flexible middle portion 68 extending between the first and second end portions. As also described above, the first end portion 64 of each of the wing members 60 can be substantially flush with the outer circumferential surface 56$_b$ when the apparatus 10$_b$ is in the radially collapsed configuration, and substantially radial to the outer circumferential surface when the apparatus is in the radially expanded configuration. The main body portion 52$_b$ can include any number, size, and configuration of wing members 60, as illustrated in FIGS. 1A-B and FIGS. 3A-8.

Figure 38:
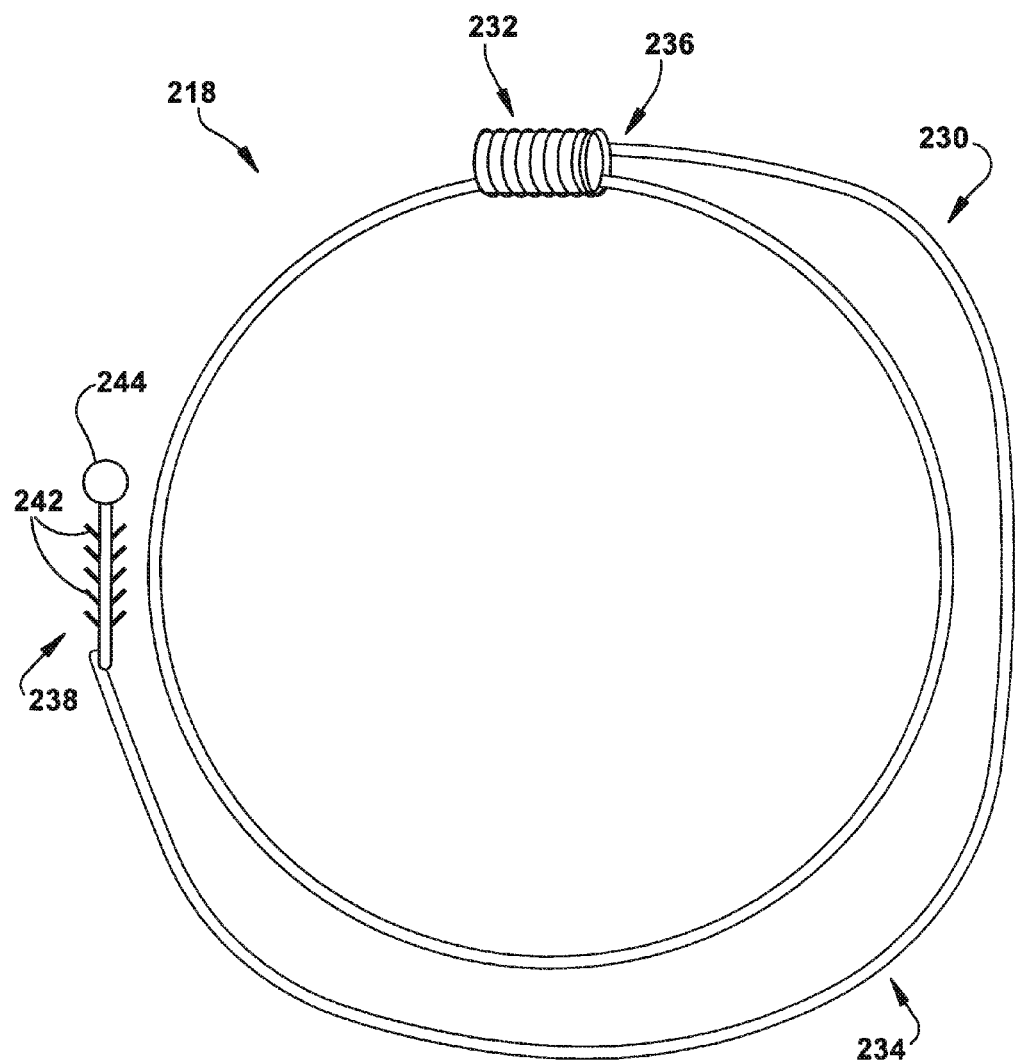
FIG. 38 is a schematic illustration showing a locking mechanism of the expandable rings in FIGS. 37A-B.

The main body portion 52$_b$ of the expandable support member 12 can additionally or optionally include at least one expandable ring 218 securely disposed about the outer circumferential surface 56$_b$. One skilled in the art will appreciate that the at least one expandable ring 218 can additionally or optionally be included as part of the apparatus 10 and 10$_b$ disclosed herein. The diameter of the at least one expandable ring 218 is adjustable and, as described below, can be adjusted to a predetermined diameter using a locking mechanism 230 (FIG. 38). For example, the at least one expandable ring 218 (FIG. 34A) can expand along with the expandable support member 12 and lock into the predetermined diameter (via the locking mechanism 230) when the outer circumferential surface 56$_b$ of the expandable support member engages a portion of the indwelling bioprosthetic valve 200 (e.g., the annulus or frame 204). By dynamically adjusting its diameter to the diameter of the expandable support member 12, the at least one expandable ring 218 can provide additional strength and radial force to the main body portion 52$_b$ of the apparatus 10$_b$, prevent or mitigate recoil of the apparatus, and prevent or mitigate unwanted changes in the shape of the apparatus once implanted.

One or more expandable rings 218 can be disposed about the outer circumferential surface 56$_b$ near or on the circumferential axis CA and/or near or on the first end portion 48 and/or second end portion 50$_b$ of the expandable support member 12. As shown in FIG. 37A, for example, a first expandable ring 218' can be disposed about the outer circumferential surface 56 near or on the circumferential axis CA. Alternatively, first and second expandable rings 218' and 218" can be securely disposed about the first and second end portions 48 and 50 of the expandable support member 12 (FIG. 37B). The at least one expandable ring 218 can be made of any one or combination of materials that allows the at least one expandable ring to dynamically adjust its diameter in-step the diameter of the expandable support member 12. The at least one expandable ring 218 can be a continuous piece of material (e.g., a continuously coiled wire) or, alternatively, a non-continuous piece of material comprising proximal and distal end portions (not shown). It will be appreciated that all or only a portion of the expandable ring 218 can be covered with a biocompatible material, such as ePTFE.

In one example of the present invention, the at least one expandable ring 218 can be spring-loaded to permit the at least one expandable ring to dynamically adjust its diameter in-step the diameter of the expandable support member 12. As shown in FIG. 38, for example, the at least one expandable ring 218 can include a spring 232 that is integrally formed therewith. The spring 232 can allow the at least one expandable ring 218 to dynamically adjust its diameter in-step the diameter of the expandable support member 12. As also shown in FIG. 38, the locking mechanism 230 can comprise a tensioning member 234 (e.g., a wire) having first and second ends 236 and 238. The first end 236 can be securely attached to the at least one expandable ring 218 at a desired point, such as at or near the spring 232. The second end 238 can include a slidable locking member 240 having a plurality of teeth 242 and a head 244 to facilitate locking and adjustment of the at least one expandable ring 218. It will be appreciated that the at least one expandable ring 218 can include one more locking mechanisms 230.

As noted above, the expandable support member 12 can include a bioprosthetic valve 202 secured within the main body portion 52$_b$. In one example of the present invention, the bioprosthetic valve 202 can comprise a stentless, substantially dehydrated valve. The substantially dehydrated bioprosthetic valve can be treated and preserved with a dry tissue valve procedure, such as the one described in U.S. Pat. No. 6,534,004. Additionally, the substantially dehydrated bioprosthetic valve can be made with one or more pieces of tissue (e.g., pericardial tissue) as described above.

Figure 39:
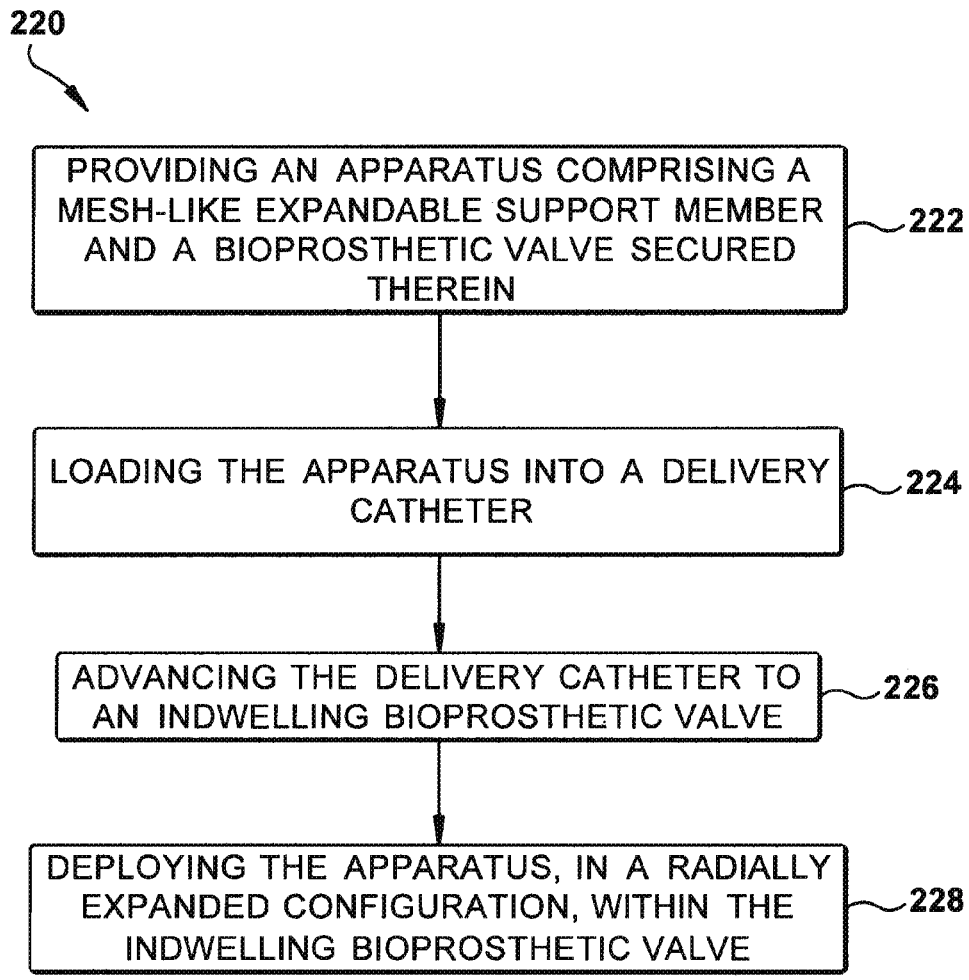
FIG. 39 is a process flow diagram illustrating a method for replacing an indwelling bioprosthetic valve in a subject according to another aspect of the present invention.

FIG. 39 illustrates another aspect of the present invention comprising a method 220 for replacing a previously-implanted or indwelling bioprosthetic valve 200 having at least two commissural portions 206 (e.g., posts) spaced apart by a first distance D1. As noted above, replacement of diseased bioprosthetic valves reduces the morbidity and mortality associated with native valvular disease, but comes at the expense of risking complications unique to the implanted bioprosthetic device. When bioprosthetic valves fail, for example, their removal and replacement can entail a highly complicated and invasive procedure. Advantageously, the method 220 of the present invention can be used to replace a previously-implanted or indwelling bioprosthetic valve 200 that has failed without the need for invasive removal of the failed, which thereby avoids potential surgical complications and hardship on the patient.

Although the method 220 is illustrated using a percutaneous approach to replace an indwelling bioprosthetic mitral valve 200, it will be appreciated that other approaches (such as those listed above) can be used, and that the method can be used to replace other indwelling bioprosthetic valves, such as indwelling bioprosthetic tricuspid and aortic valves. Additionally, it will be appreciated that the method 220 can alternatively be performed in a similar manner as the method 78$_a$ illustrated in FIGS. 26-32, i.e., employing a self-expandable apparatus 10.

Referring again to FIG. 39, one step of the method 220 can include providing an apparatus 10$_b$ comprising an expandable support member 12 and a bioprosthetic valve 202 secured therein (Step 222). The expandable support member 12 of the apparatus 10$_b$ can generally include a first end portion 48, a second end portion 50$_b$, a main body portion 52$_b$ extending between the first and second end portions, an outer circumferential surface 56$_b$, and a plurality of wing members 60' and 60" spaced apart from one another by an expandable region $62_b$. The main body portion $52_b$ can additionally or optionally include at least one expandable ring 218 securely disposed about the outer circumferential surface $56_b$. The second end portion $50_b$ can include at least two flexible arch members 208 spaced apart by a second distance D2 that is about equal to the first distance D1 of the indwelling bioprosthetic valve 200. In one example of the method, the apparatus $10_b$ can be constructed as shown in FIGS. 34A-35B and described above.

Prior to implantation of the apparatus $10_b$, the dimensions of the indwelling bioprosthetic valve 200 can be determined (if not already done so) using one or a combination of known imaging techniques, such as MRI, fluoroscopy, echocardiography, CT, angiography, and/or ultrasound. To enable delivery and deployment of the apparatus $10_b$, the apparatus can then be loaded into a delivery catheter 92 at Step 224. For example, the apparatus $10_b$ can be positioned about an inflatable member 90 (e.g., a balloon) in the radially collapsed configuration (FIG. 40) and then loaded into the delivery catheter 92 in a known manner.

At Step 226, the apparatus $10_b$ can be advanced through the delivery catheter 92 to the indwelling bioprosthetic valve 200. The apparatus $10_b$ can be advanced to the indwelling bioprosthetic valve 200 in a manner similar or identical to the approach illustrated in FIGS. 20-22 and described above. Briefly, for example, a guidewire 94 can be inserted into the vasculature via a femoral or jugular vein and, under image guidance, steered through the vasculature into the inferior vena cava 36 or superior vena cava 34 (respectively). The guidewire 94 can then be passed across the right atrium 24 so that the distal end 96 of the guidewire pierces the interatrial septum 32. The guidewire 94 can be extended across the left atrium 26 and downward through the indwelling bioprosthetic valve 200 so that the distal end 96 of the guidewire is securely positioned in the left ventricle 30. After the guidewire 94 is appropriately positioned, the delivery catheter 92 can be passed over the guidewire and the apparatus $10_b$ loaded thereon. An axial force can then be applied so that the apparatus $10_b$ is passed over the guidewire 94 and positioned at the distal end 98 of the delivery catheter 92.

Figure 40:
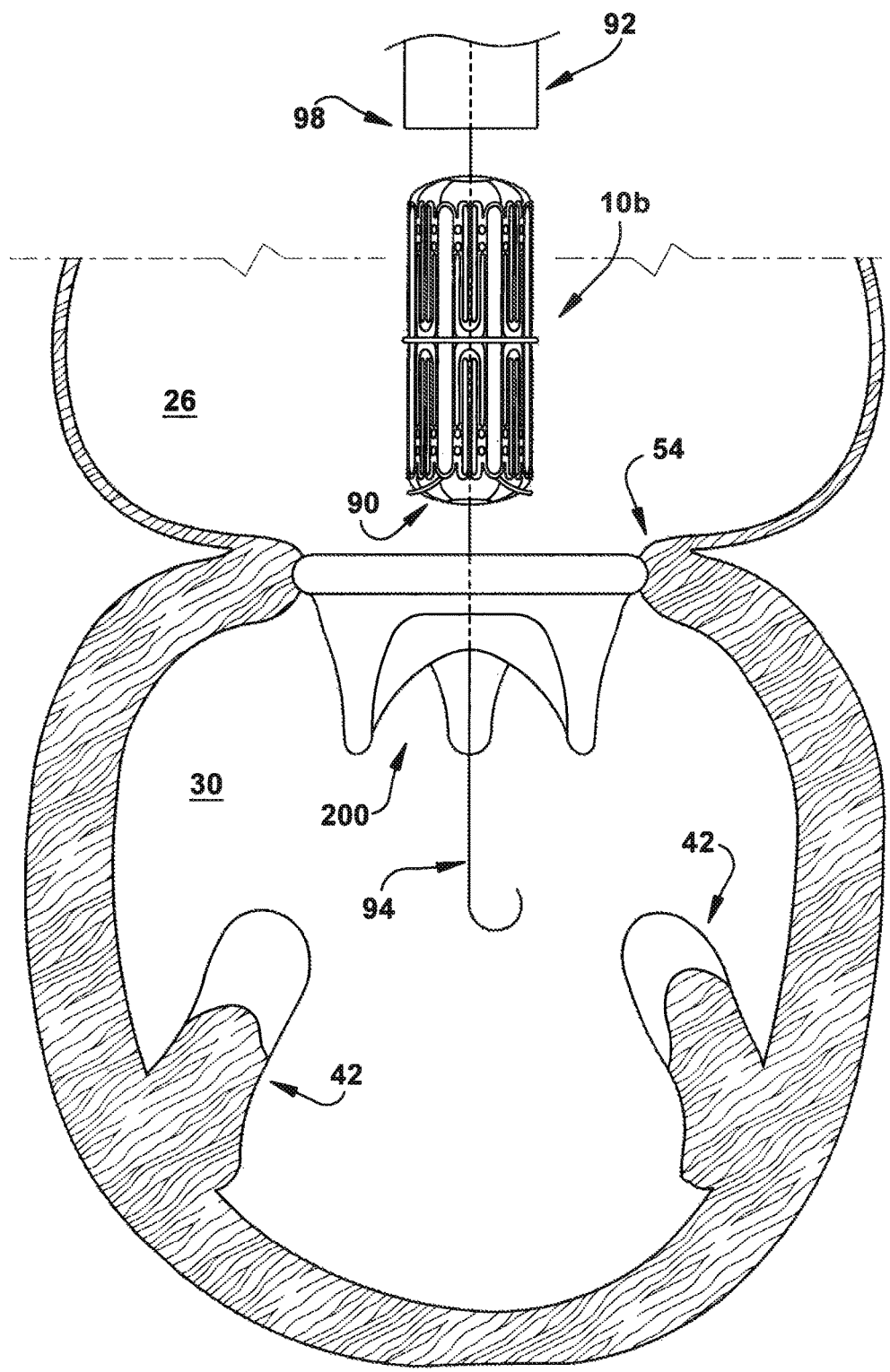
FIG. 40 is a cross-sectional view showing the apparatus of FIGS. 34A-B placed about an inflatable member and being delivered to an indwelling bioprosthetic mitral valve.
Figure 41:
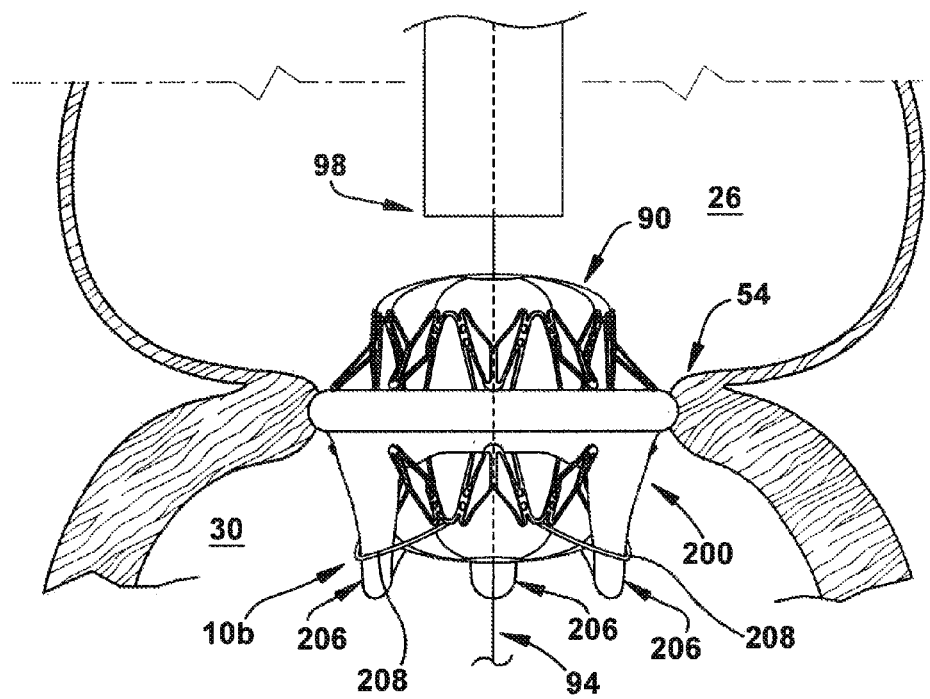
FIG. 41 is a cross-sectional magnified view of the apparatus in FIG. 40 being deployed in the indwelling bioprosthetic mitral valve.

Upon reaching the distal end 98 of the delivery catheter 92, the apparatus $10_b$ can be deployed at Step 228. As shown in FIGS. 40-41, the apparatus $10_b$ can be positioned adjacent the indwelling bioprosthetic valve 200 and then advanced therein. After positioning the apparatus $10_b$ in the indwelling bioprosthetic valve 200, the delivery catheter 92 can be progressively withdrawn to free the apparatus from the delivery catheter. If desired, the position of the apparatus $10_b$ in the indwelling bioprosthetic valve 200 can be monitored, controlled, and/or quality assured by one or more known imaging techniques.

Figure 42:
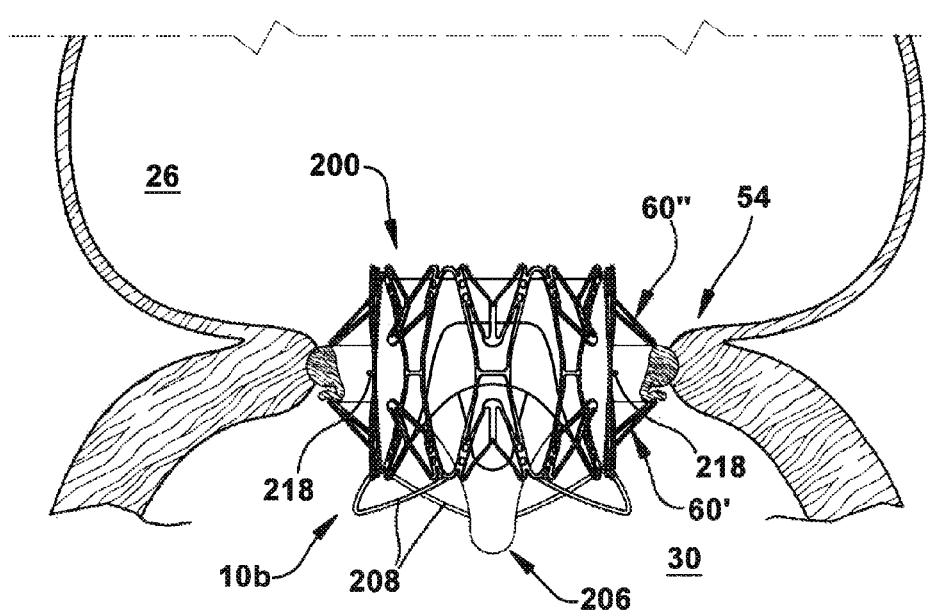
FIG. 42 is a cross-sectional magnified view showing the apparatus in FIG. 41 deployed within the indwelling bioprosthetic mitral valve.

After positioning the apparatus $10_b$ as shown in FIG. 41, the inflatable member 90 can be inflated using a suitable inflation medium, such as air or a saline solution. Inflation of the inflatable member 90 can push the main body portion $52_b$ of the expandable support member 12 radially outward and thereby increase the diameter of the expandable support member. As the main body portion $52_b$ expands, the expandable ring 218 (or rings) can dynamically expand into contact with the frame 204 (or annulus, depending upon the location of the ring or rings) of the indwelling bioprosthetic valve 200. Expansion of the main body portion $52_b$ can simultaneously cause the wing members 60' and 60" and the arch members 208 to radially expand. As shown in FIG. 42, for example, the first end portion 64 of each of the wing members 60' and 60" can move radially outward from the outer circumferential surface $56_b$ into contact with the leaflets of the indwelling bioprosthetic valve 200 to pin the leaflets against the frame 204 of the indwelling bioprosthetic valve. Additionally, each of the arch members 208 can move radially outward into contact with the commissural portions 206 (e.g., posts) of the indwelling bioprosthetic valve 200. For example, each of the arch members 208 can loop around or over each of the commissural portions 206 (e.g., like a lasso).

With the apparatus $10_b$ in the radially expanded configuration, the first and second plurality of wing members 60' and 60", the expandable ring(s) 218, and the arch members 208 can secure the apparatus in place of the indwelling bioprosthetic valve 200. Consequently, blood can now flow through the bioprosthetic valve 202 of the apparatus $10_b$. As blood contacts the bioprosthetic valve 202, the interstices of the bioprosthetic valve can be re-hydrated and cause the bioprosthetic valve to obtain its original (or substantially original) properties and assume normal (or substantially normal) blood flow performance. It should be appreciated that the bioprosthetic valve 202 may not be re-hydrated with blood where the bioprosthetic valve comprises a standard (i.e., non-dehydrated) bioprosthetic valve (e.g., made of porcine tissue). With the apparatus $10_b$ fully deployed, the inflatable member 90 can be deflated, moved out of the mitral valve annulus 54, and the procedure completed.

It will be appreciated that other configurations of the "valve-in-valve" apparatus $10_b$ and method 220 can be used to replace other types of indwelling medical devices, such a previously-implanted or indwelling annuloplasty ring (not shown). For example, the apparatus 10 shown in FIGS. 1A-B can be securely disposed within an annuloplasty ring (not shown) to form an apparatus for replacing failed annuloplasty ring. Using one or a combination of the surgical implantation techniques discussed above, such a "valve-in-ring" apparatus can implanted in place of the failed annuloplasty ring to mitigate or prevent regurgitation of blood therethrough.

Figure 44:
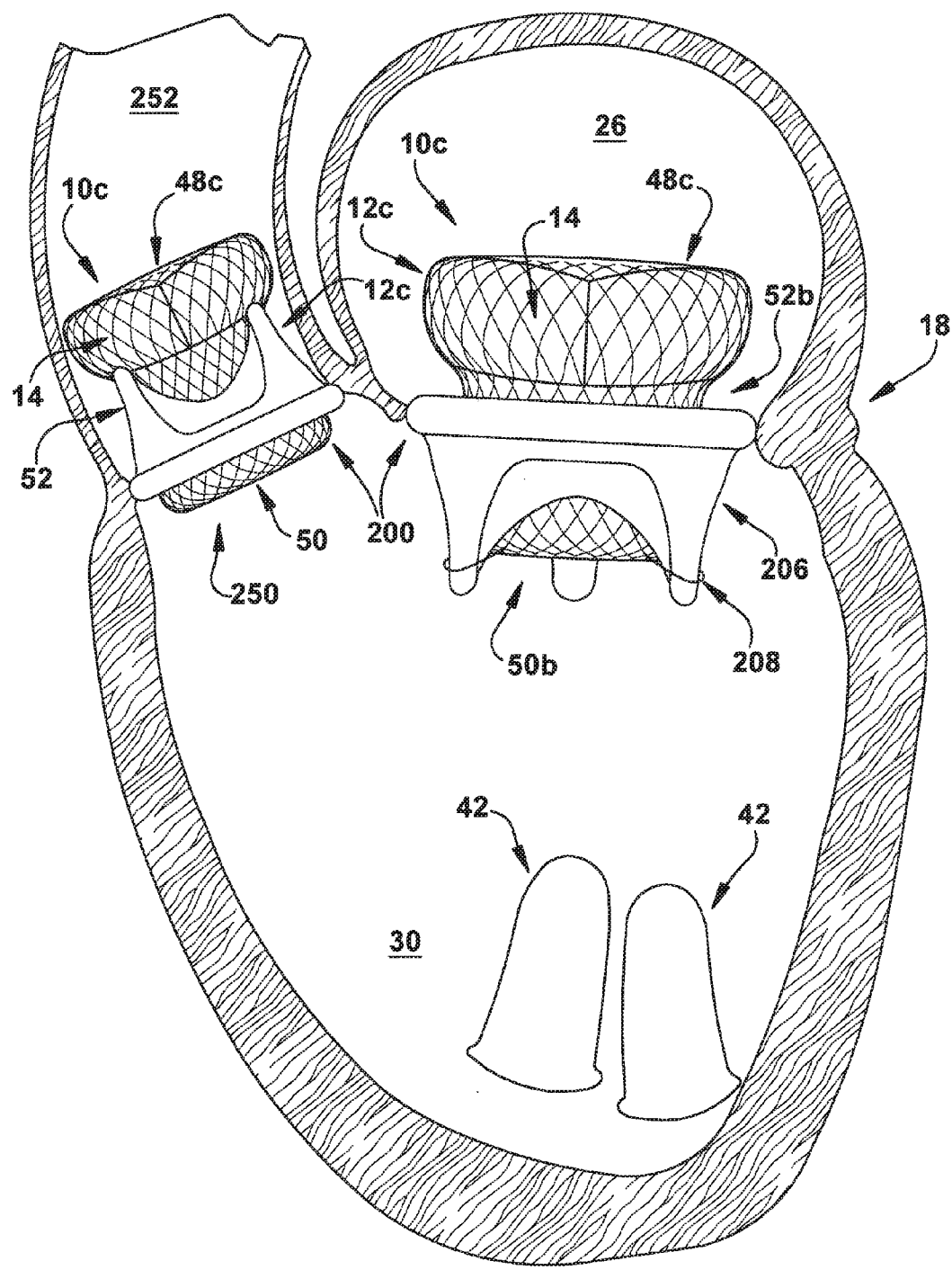
FIG. 44 is a cross-sectional view showing the apparatus in FIG. 43 implanted in an indwelling bioprosthetic aortic valve and an alternative configuration of the apparatus in FIGS. 33A-36B implanted in an indwelling bioprosthetic mitral valve.
Figure 45:
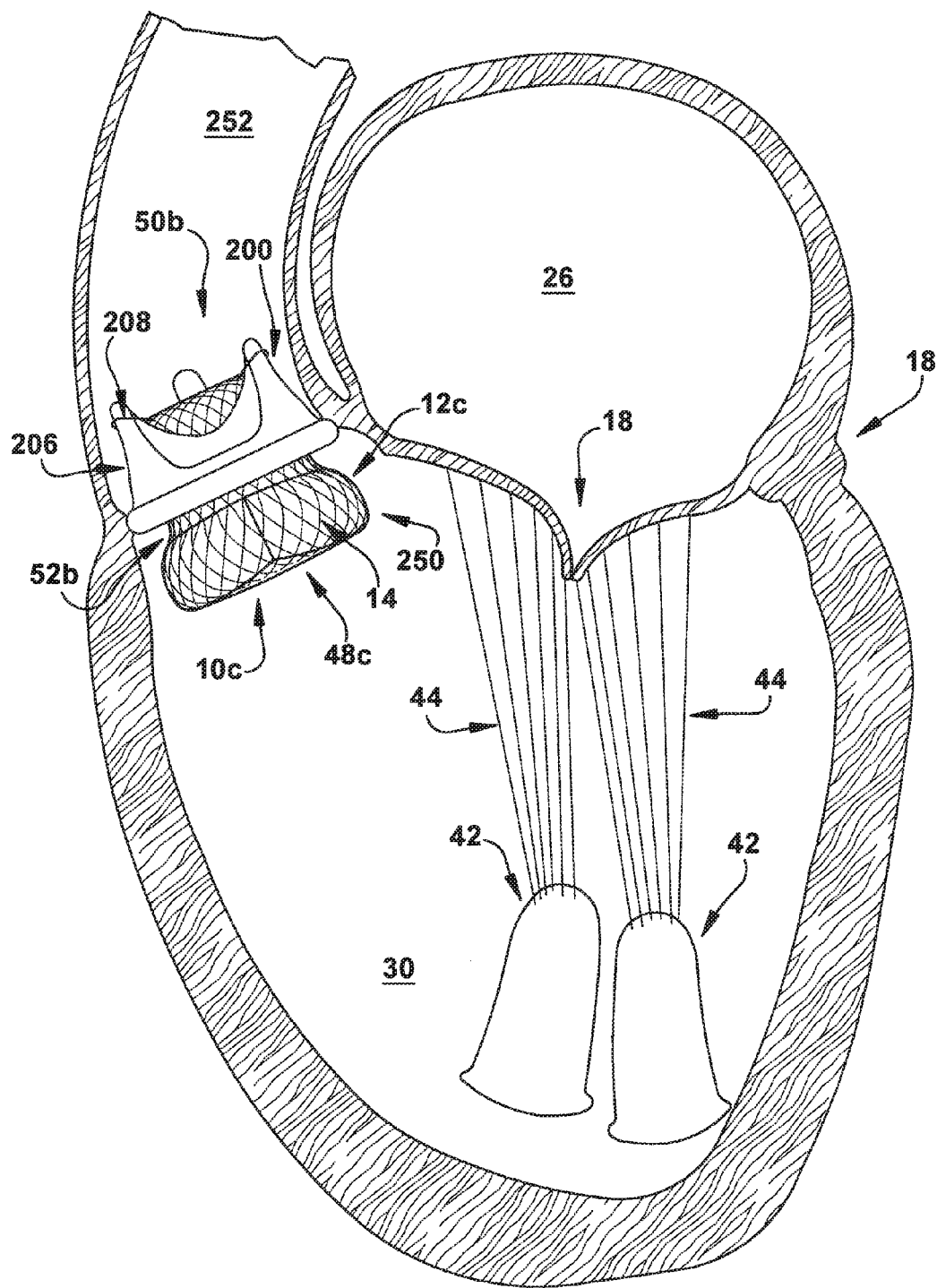
FIG. 45 is a cross-sectional view showing the apparatus in FIG. 44 (implanted in an indwelling bioprosthetic mitral valve) implanted in an indwelling bioprosthetic aortic valve.

Another aspect of the present invention is illustrated in FIGS. 43-45. The apparatus $10_c$, is identically constructed as the apparatus 10 and $10_b$ shown in FIGS. 1A-B and 33A-36B, except where as described below. In FIGS. 43-45, structures that are identical as structures in FIGS. 1A-B and 33A-36B use the same reference numbers, whereas structures that are similar but not identical carry the suffix "c".

Placement of bioprosthetic valves within previously-implanted or indwelling bioprosthetic valves can be difficult or impossible in certain subsets of patients due to the small diameter of such indwelling valves. One such patient subset can include elderly patients, such as those over 80 years of age. In these elderly patients, the annulus of an indwelling bioprosthetic valve can become too constricted over time and thereby prevent "valve-in-valve" or "stent-in-stent" replacement procedures. Additionally, in pediatric patients, the reduced size of the valve annuluses can prevent such "valve-in-valve" or "stent-in-stent" replacement procedures. Advantageously, the apparatus $10_c$ of the present invention has a unique configuration to allow for replacement of failed indwelling bioprosthetic valves (or other devices, such as annuloplasty rings) in elderly and pediatric patients.

As shown in FIG. 43, the apparatus $10_c$, can comprise an expandable support member $12_c$, having a first end portion $48_c$, a second end portion 50, a main body portion 52 extending between the first and second end portions, and a prosthetic valve 14 (such as a bioprosthetic valve 202). The apparatus $10_c$, can be used to replace a failed bioprosthetic valve 200 that was previously implanted in the mitral valve 18 (FIG. 43), the tricuspid valve 20 (not shown implanted), or the aortic valve 250 (FIGS. 44-45). The expandable support member $12_c$, can be cork-shaped such that the first end portion 48, has a flared configuration and the diameter of the first end portion is greater than the diameter of the second end portion 50. The expandable support member $12_c$, can have a 3D, saddle-shaped configuration and be made of one or a combination of expandable materials (described above). Although not shown in detail, the main body portion 52 of the expandable support member $12_c$, can also include a plurality of wing members 60 (as described above).

The apparatus $10_c$, can be implanted in the indwelling bioprosthetic valve 200 using a similar percutaneous technique as described in the method 220 above. It will be appreciated, however, that one or combination of the other surgical implantation techniques discussed above may also be used to implant the apparatus $10_c$. As shown in FIG. 43, the apparatus $10_c$, can be implanted in an indwelling bioprosthetic valve 200 (e.g., mitral valve 18) such that the second end portion 50 and/or the main body portion 52 are securely seated in the bioprosthetic valve, and the first end portion $48_c$, extends into the left ventricle 30. Advantageously, the cork-shaped configuration of the expandable support member $12_c$ allows the apparatus $10_c$ to fit within the narrowed cross-section of the indwelling bioprosthetic valve 200 and thereby mitigate or prevent regurgitation of blood flow therethrough.

Similarly, the apparatus $10_c$, can be implanted in a failed indwelling bioprosthetic valve (e.g., aortic valve 250) as shown in FIG. 45. Using a percutaneous approach, for example, the apparatus $10_c$, can be implanted within the indwelling bioprosthetic valve 200 such that the second end portion 50 and/or the main body portion 52 are securely seated in the bioprosthetic valve, and the first end portion $48_c$, extends into the aorta 252.

Figure 46:
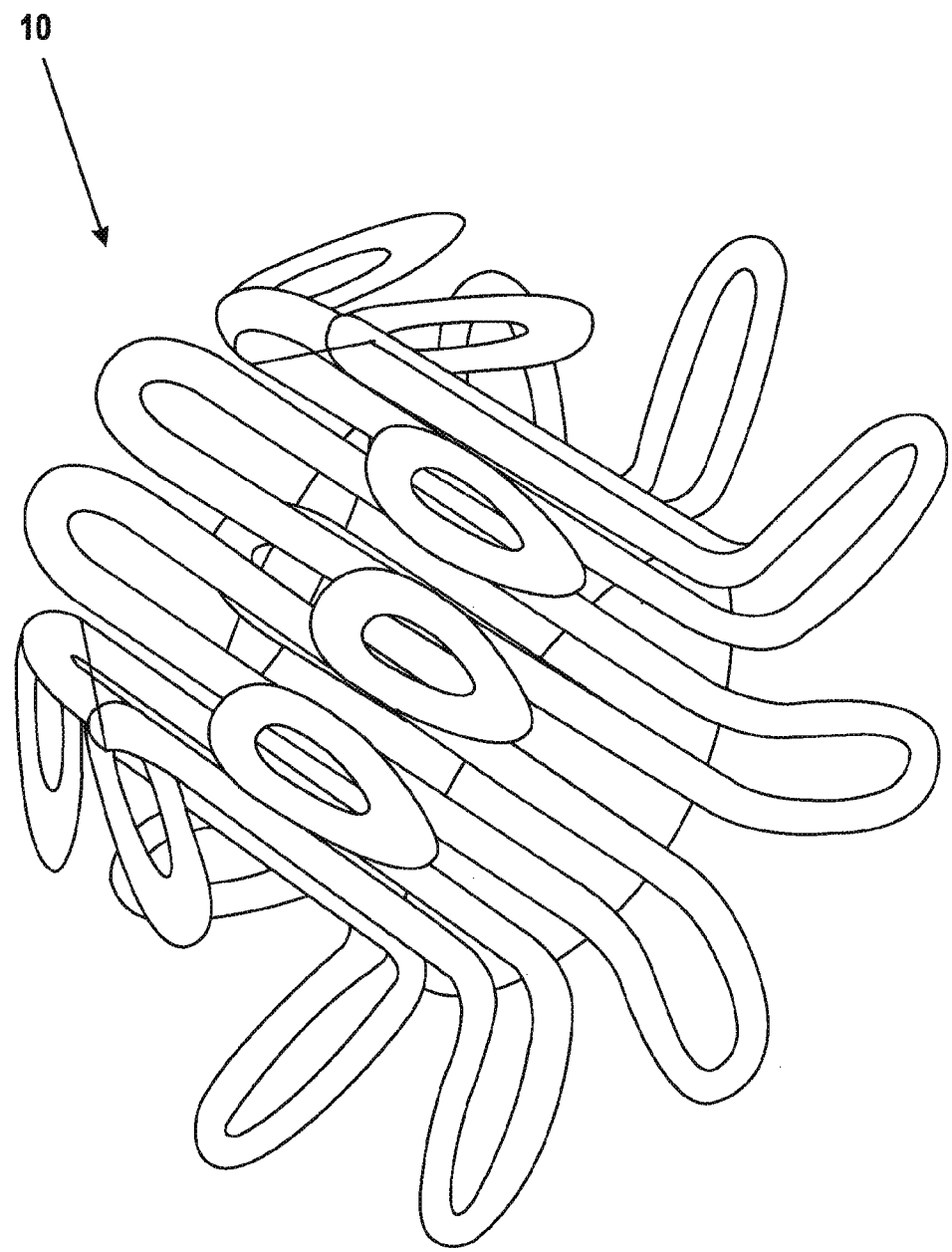
FIG. 46 is a perspective view showing an alternative configuration of the apparatus shown in FIGS. 1A-B.

It will be appreciated that the apparatus $10_c$, can additionally or optionally be constructed in a similar fashion as the apparatus $10_b$ shown in FIGS. 33A-36B. Referring to FIGS. 45-46, for example, the apparatus $10_c$, can comprise an expandable support member $12_c$, having a first end portion $48_c$, a second end portion $50_b$, a main body portion $52_b$ extending between the first and second end portions, and a prosthetic valve 14 (such as a bioprosthetic valve 202). As described above, the expandable support member $12_c$, can be cork-shaped such that the first end portion $48_c$, has a flared configuration and the diameter of the first end portion is greater than the diameter of the second end portion $50_b$. The main body portion $52_b$ can include a plurality of wing members 60 (not shown in detail), and the second end portion $50_b$ can include at least one flexible arch member 208. Additionally or optionally, the second end portion $50_b$ can include at least one secondary flexible arch member 210 (not shown in detail) and/or at least one expandable ring 218.

The apparatus $10_c$, can be implanted in the indwelling bioprosthetic valve 200 using a percutaneous technique, as described in the method 220 above. As shown in FIG. 44, for example, the apparatus $10_c$, can be implanted in an indwelling bioprosthetic valve 200 (e.g., mitral valve 18) such that the second end portion $50_b$ and/or the main body portion $52_b$ are securely seated within the bioprosthetic valve, and the first end portion 48, extends into the left atrium 26. As described above, the at least one flexible arch member 208 can secure the apparatus $10_c$ in the indwelling bioprosthetic valve 200 by engaging at least one commissural portion 206 (e.g., a post) of the indwelling bioprosthetic valve.

Similarly, the apparatus $10_c$ can be implanted in a failed indwelling bioprosthetic valve (e.g., aortic valve 250) as shown in FIG. 45. Using a percutaneous approach, for example, the apparatus $10_c$ can be implanted within the indwelling bioprosthetic valve 200 such that the second end portion $50_b$ and/or the main body portion $52_b$ are securely seated in the bioprosthetic valve, and the first end portion $48_c$ extends into the aorta 252.

Figure 47:
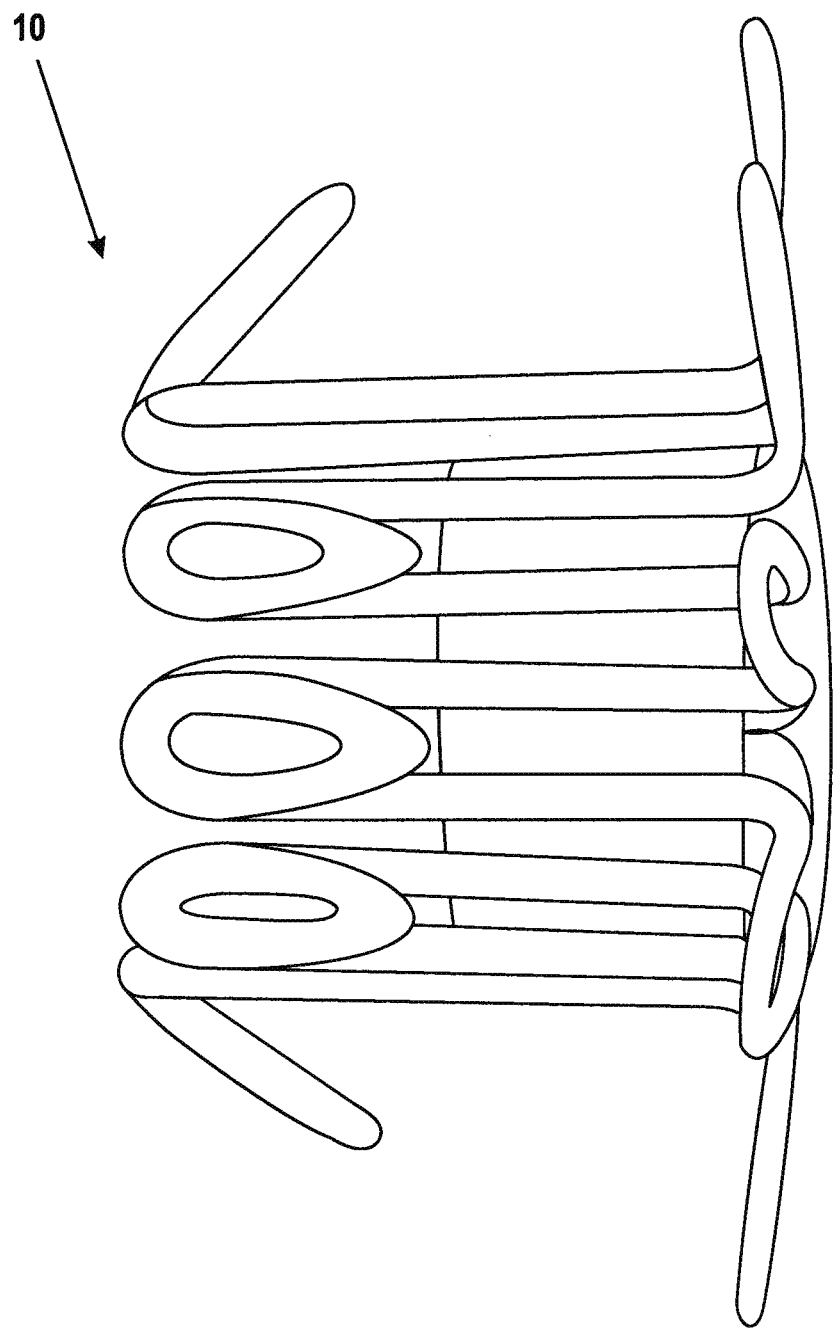
FIG. 47 is a side view of the apparatus shown in FIG. 46.
Figure 48:
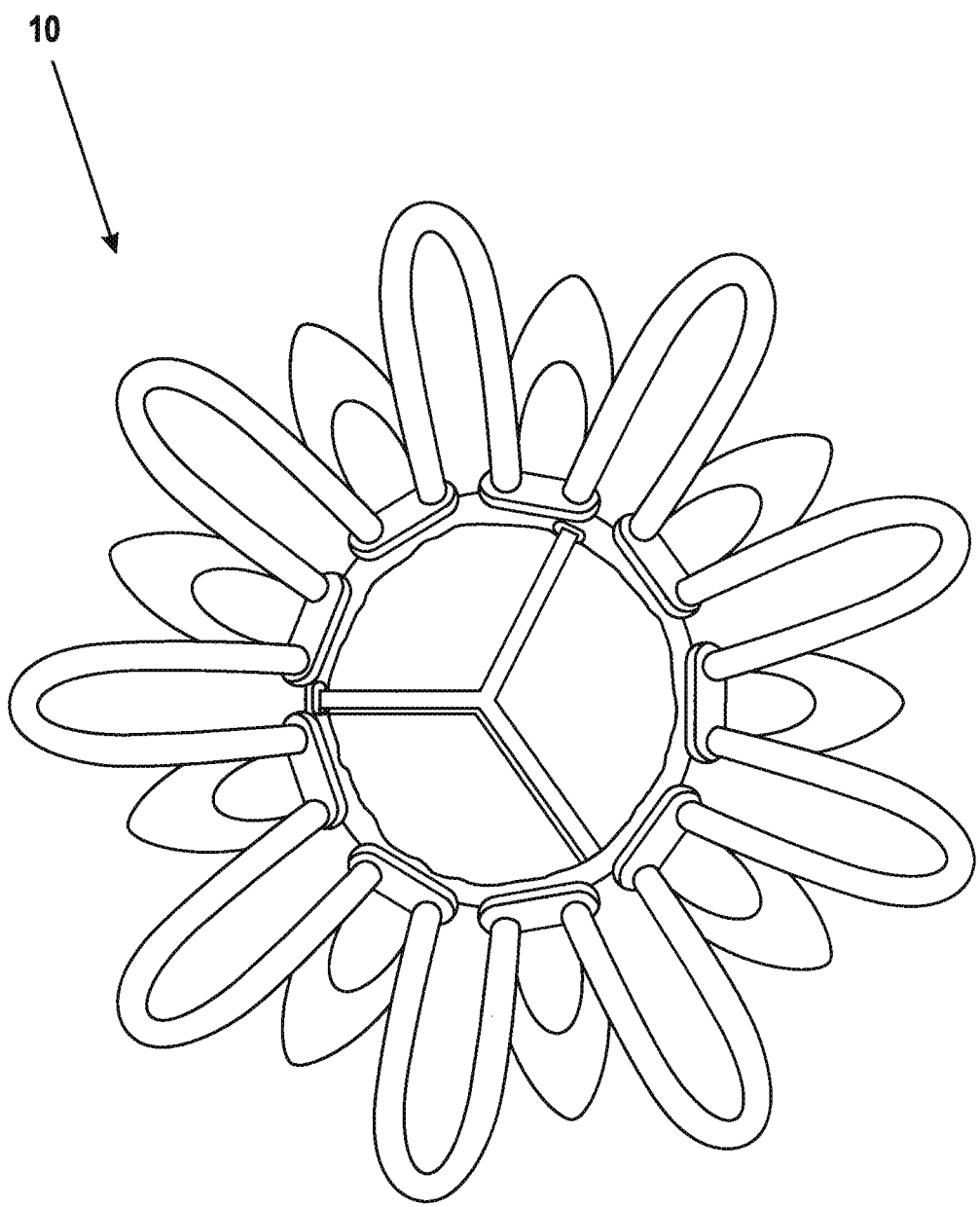
FIG. 48 is a top view of the apparatus shown in FIG. 46.

From the above description of the invention, those skilled in the art will perceive improvements, changes and modifications. For example, the substantially dehydrated bioprosthetic valve 14 and 202 may be exposed to a re-hydrating or rinsing solution while the apparatus 10, $10_b$, and $10_c$, is disposed within the delivery catheter 92 prior to delivery. Alternatively, the substantially dehydrated bioprosthetic valve 14 and 202 may by re-hydrated by blood while the apparatus 10, $10_b$, and $10_c$ is being deployed in the vasculature. Additionally, it will be appreciated that the apparatus 10, $10_b$, and $10_c$ can alternatively be configured as shown in FIGS. 46-48. Such improvements, changes, and modifications are within the skill of the art and are intended to be covered by the appended claims.

Having described the invention, we claim:

1. A method for replacing a diseased cardiac valve, said method comprising the steps of:
    providing an apparatus comprised of a prosthetic valve secured within a main body portion of an expandable support member having a first end portion and a second end portion, the main body portion including an outer circumferential surface, a circumferential axis extending about the circumferential surface, and a first and second plurality of wing members each integrally formed with the main body portion of the expandable support member and spaced apart from one another along the length of the circumferential axis of the main body portion, wherein the second plurality of wing members is circumferentially spaced around an upper portion of the expandable support member and wherein the second end portion of the expandable support member is comprised of at least two flexible arch members;
    maintaining the expandable support member in a radially collapsed configuration;
    loading the apparatus into a delivery catheter;
    advancing the delivery catheter to the diseased cardiac valve; and
    deploying the apparatus to a radially expanded configuration by extending both the first and second plurality wing members substantially radial to, and within the length of the axis of the outer circumferential surface of the main body portion, causing the first and second plurality of wing members to engage opposite sides of an annulus of the diseased native cardiac valve to secure the apparatus in place of the diseased cardiac valve; and moving the at least two flexible arch members from a collapsed configuration to an expanded configuration to offset the at least two flexible arch members from the outer circumferential surface of the main body portion by about 90°.

2. The method of claim 1, wherein said step of advancing the delivery catheter to the diseased cardiac valve further comprises the step of positioning the delivery catheter so that the apparatus is adjacent the valve annulus.

3. The method of claim 1, wherein said step of providing an apparatus further comprises providing a substantially dehydrated bioprosthetic valve.

4. The method of claim 3, wherein blood re-hydrates the substantially dehydrated bioprosthetic valve before the apparatus is deployed.

5. The method of claim 3, wherein blood re-hydrates the substantially dehydrated bioprosthetic valve after the apparatus is deployed.

\* \* \* \* \*